United States Patent
Maxwell et al.

(10) Patent No.: US 12,071,669 B2
(45) Date of Patent: Aug. 27, 2024

(54) METHODS AND SYSTEMS FOR DETECTION OF ABNORMAL KARYOTYPES

(71) Applicant: REGENERON PHARMACEUTICALS, INC., Tarrytown, NY (US)

(72) Inventors: Evan Maxwell, Danbury, CT (US); Lukas Habegger, Stamford, CT (US); Jeffrey Reid, Stamford, CT (US)

(73) Assignee: REGENERON PHARMACEUTICALS, INC., Tarrytown, NY (US)

( * ) Notice: Subject to any disclaimer, the term of this patent is extended or adjusted under 35 U.S.C. 154(b) by 1240 days.

(21) Appl. No.: 15/431,715

(22) Filed: Feb. 13, 2017

(65) Prior Publication Data

US 2017/0233806 A1    Aug. 17, 2017

Related U.S. Application Data

(60) Provisional application No. 62/294,669, filed on Feb. 12, 2016.

(51) Int. Cl.

| | |
|---|---|
| *G01N 33/48* | (2006.01) |
| *C12Q 1/6881* | (2018.01) |
| *G16B 20/00* | (2019.01) |
| *G16B 20/10* | (2019.01) |
| *G16B 20/20* | (2019.01) |
| *G16B 30/00* | (2019.01) |
| *G16B 30/10* | (2019.01) |
| *G16B 40/00* | (2019.01) |
| *G16B 40/20* | (2019.01) |
| *G16B 50/00* | (2019.01) |

(52) U.S. Cl.
CPC ........... *C12Q 1/6881* (2013.01); *G16B 20/00* (2019.02); *G16B 20/10* (2019.02); *G16B 20/20* (2019.02); *G16B 30/00* (2019.02); *G16B 30/10* (2019.02); *G16B 40/00* (2019.02); *G16B 40/20* (2019.02); *G16B 50/00* (2019.02); *C12Q 2600/156* (2013.01)

(58) Field of Classification Search
None
See application file for complete search history.

(56) References Cited

U.S. PATENT DOCUMENTS

| | | |
|---|---|---|
| 5,840,484 A | 11/1998 | Seilhamer et al. |
| 6,434,542 B1 | 8/2002 | Farmen et al. |
| 6,586,251 B2 | 7/2003 | Economides et al. |
| 6,596,541 B2 | 7/2003 | Murphy et al. |
| 6,658,396 B1 | 12/2003 | Tang et al. |
| 6,703,228 B1 | 3/2004 | Landers et al. |
| 6,909,971 B2 | 6/2005 | Toivonen et al. |
| 6,955,883 B2 | 10/2005 | Margus et al. |
| 7,065,451 B2 | 6/2006 | Garner et al. |
| 7,105,348 B2 | 9/2006 | Murphy et al. |
| 7,107,155 B2 | 9/2006 | Frudakis |
| 7,213,009 B2 | 5/2007 | Pestotnik et al. |
| 7,232,656 B2 | 6/2007 | Balasubramanian et al. |
| 7,324,928 B2 | 1/2008 | Kitchen et al. |
| 7,424,371 B2 | 9/2008 | Kamentsky |
| 7,461,006 B2 | 12/2008 | Gogolak |
| 7,529,685 B2 | 5/2009 | Davies et al. |
| 7,622,271 B2 | 11/2009 | Kennedy et al. |
| 7,640,113 B2 | 12/2009 | Frudakis et al. |
| 7,698,117 B2 | 4/2010 | Usuka et al. |
| 7,702,468 B2 | 4/2010 | Chinitz et al. |
| 7,734,656 B2 | 6/2010 | Bessette et al. |
| 7,809,539 B2 | 10/2010 | Brocklebank et al. |
| 7,809,660 B2 | 10/2010 | Friedlander et al. |
| 7,820,378 B2 | 10/2010 | van den Boom et al. |
| 7,840,512 B2 | 11/2010 | Pandya et al. |
| 7,912,650 B2 | 3/2011 | Kato et al. |
| 7,912,674 B2 | 3/2011 | Killoren Clark et al. |
| 7,937,225 B2 | 5/2011 | Mishra et al. |
| 7,957,913 B2 | 6/2011 | Chinitz et al. |
| 7,979,215 B2 | 7/2011 | Sampas |
| 7,996,157 B2 | 8/2011 | Zabeau et al. |
| 8,010,295 B1 | 8/2011 | Magness et al. |
| 8,050,870 B2 | 11/2011 | Heckerman et al. |
| 8,051,033 B2 | 11/2011 | Kenedy et al. |
| 8,078,407 B1 | 12/2011 | Brown |
| 8,095,389 B2 | 1/2012 | Dalton et al. |
| 8,122,073 B2 | 2/2012 | Jung et al. |

(Continued)

FOREIGN PATENT DOCUMENTS

| | | |
|---|---|---|
| WO | WO-2012/006291 A2 | 1/2012 |
| WO | WO-2012/051346 A1 | 4/2012 |

(Continued)

OTHER PUBLICATIONS

"Picard Metrics Definitions" (2014) [retrieved on line Dec. 24, 2021] Retrieved from the Internet <URL: http//broadinstitute.github.io/picard/picardmetric-definitions.html>.*

Illumina, Technical Note: Informatics, Human, W. G. S. "Sequencing Coverage Calculation Methods for Human Whole-Genome Sequencing." (2014).*

Robinson, J.T., "The K-D-B-Tree: A Search Structure for large Multidimensional Dynamic Indexes", ProceedingSIGMOD '81 Proceedings of the 1981 ACM SIGMOD international conference on Management of data pp. 10-18.

(Continued)

*Primary Examiner* — Anna Skibinsky

(74) *Attorney, Agent, or Firm* — Ballard Spahr LLP

(57) ABSTRACT

Methods and systems for detecting abnormal karyotypes are disclosed. An example method can comprise determining read coverage data, allele balance distributions of heterozygous SNPs, and chromosomal segments where heterozygosity is not observed. The methods and systems can then determine one or more metrics which can be indicative of abnormal karyotype(s).

14 Claims, 27 Drawing Sheets

(56) References Cited

U.S. PATENT DOCUMENTS

| | | |
|---|---|---|
| 8,140,270 B2 | 3/2012 | Kingsmore et al. |
| 8,190,373 B2 | 5/2012 | Huang et al. |
| 8,195,415 B2 | 6/2012 | Fan et al. |
| 8,296,116 B2 | 10/2012 | Solomon |
| 8,315,957 B2 | 11/2012 | Heckerman et al. |
| 8,326,648 B2 | 12/2012 | Kenedy et al. |
| 8,335,652 B2 | 12/2012 | Soykan et al. |
| 8,340,950 B2 | 12/2012 | Avey |
| 8,367,333 B2 | 2/2013 | Gudbjartsson et al. |
| 8,372,584 B2 | 2/2013 | Shoemaker et al. |
| 8,380,539 B2 | 2/2013 | Linder et al. |
| 8,428,886 B2 | 4/2013 | Wong et al. |
| 8,429,105 B2 | 4/2013 | Jacobson |
| 8,463,554 B2 | 6/2013 | Hon et al. |
| 8,489,334 B2 | 7/2013 | Chen et al. |
| 8,510,057 B1 | 8/2013 | Avey et al. |
| 8,515,679 B2 | 8/2013 | Rabinowitz et al. |
| 8,554,488 B2 | 10/2013 | Wigler et al. |
| 8,589,175 B2 | 11/2013 | Glauser et al. |
| 8,589,437 B1 | 11/2013 | Khomenko et al. |
| 8,594,944 B2 | 11/2013 | Piper et al. |
| 8,620,594 B2 | 12/2013 | Silver |
| 8,639,446 B1 | 1/2014 | Stupp |
| 8,639,639 B2 | 1/2014 | Jamil et al. |
| 8,655,599 B2 | 2/2014 | Chinitz et al. |
| 8,676,608 B2 | 3/2014 | Oesterheld et al. |
| 8,700,337 B2 | 4/2014 | Dudley et al. |
| 8,706,422 B2 | 4/2014 | Lo et al. |
| 8,718,950 B2 | 5/2014 | Worthey et al. |
| 8,725,418 B2 | 5/2014 | Aerts et al. |
| 8,725,422 B2 | 5/2014 | Halpern et al. |
| 8,731,956 B2 | 5/2014 | Bejjani et al. |
| 8,738,297 B2 | 5/2014 | Sorenson et al. |
| 8,738,300 B2 | 5/2014 | Porreca et al. |
| 8,793,245 B2 | 7/2014 | Kwete |
| 8,795,963 B2 | 8/2014 | Holm et al. |
| 8,796,182 B2 | 8/2014 | Steinthorsdottir et al. |
| 8,812,243 B2 | 8/2014 | Cardonha et al. |
| 8,814,790 B2 | 8/2014 | Eisenhandler et al. |
| 8,818,735 B2 | 8/2014 | Braun et al. |
| 8,828,657 B2 | 9/2014 | Rafnar et al. |
| 8,855,938 B2 | 10/2014 | Friedlander et al. |
| 8,862,410 B2 | 10/2014 | Hatchwell et al. |
| 8,951,735 B2 | 2/2015 | Stacey et al. |
| 8,954,337 B2 | 2/2015 | Tebbs et al. |
| 8,996,318 B2 | 3/2015 | Beatty et al. |
| 9,002,682 B2 | 4/2015 | Kasabov |
| 9,092,391 B2 | 7/2015 | Stephan et al. |
| 9,098,523 B2 | 8/2015 | Bhola et al. |
| 9,111,028 B2 | 8/2015 | Mrazek et al. |
| 9,128,861 B2 | 9/2015 | Bartha et al. |
| 9,141,755 B2 | 9/2015 | Mizuguchi et al. |
| 9,141,913 B2 | 9/2015 | Kupershmidt et al. |
| 9,165,253 B2 | 10/2015 | Cleary et al. |
| 9,177,099 B2 | 11/2015 | Ganeshalingam et al. |
| 9,183,496 B2 | 11/2015 | Harris et al. |
| 9,201,916 B2 | 12/2015 | Doddavula et al. |
| 9,213,944 B1 | 12/2015 | Do et al. |
| 9,215,162 B2 | 12/2015 | Ganeshalingam et al. |
| 9,218,450 B2 | 12/2015 | Chen et al. |
| 9,228,233 B2 | 1/2016 | Kennedy et al. |
| 9,298,804 B2 | 3/2016 | Nizzari et al. |
| 9,309,570 B2 | 4/2016 | Song et al. |
| 9,418,203 B2 | 8/2016 | Pham et al. |
| 9,449,143 B2 | 9/2016 | Vockley et al. |
| 9,483,610 B2 | 11/2016 | McMillen et al. |
| 9,504,428 B1 | 11/2016 | Gelbman et al. |
| 9,547,749 B2 | 1/2017 | OBrien et al. |
| 9,552,458 B2 | 1/2017 | White et al. |
| 9,589,104 B2 | 3/2017 | Heywood et al. |
| 9,600,627 B2 | 3/2017 | Torkamani et al. |
| 9,633,166 B2 | 4/2017 | Kupershmidt et al. |
| 9,652,587 B2 | 5/2017 | Sanborn et al. |
| 9,670,530 B2 | 6/2017 | Kostem et al. |
| 2001/0034023 A1 | 10/2001 | Stanton et al. |
| 2002/0082869 A1 | 6/2002 | Anderson |
| 2002/0133495 A1 | 9/2002 | Rienhoff et al. |
| 2002/0155467 A1 | 10/2002 | Escary |
| 2002/0187496 A1 | 12/2002 | Andersson et al. |
| 2002/0197632 A1 | 12/2002 | Moskowitz |
| 2003/0092040 A1 | 5/2003 | Bader et al. |
| 2003/0101000 A1 | 5/2003 | Bader et al. |
| 2003/0104470 A1 | 6/2003 | Fors et al. |
| 2003/0108938 A1 | 6/2003 | Pickar et al. |
| 2003/0113756 A1 | 6/2003 | Mertz |
| 2003/0138778 A1 | 7/2003 | Garner et al. |
| 2003/0195707 A1 | 10/2003 | Schork et al. |
| 2003/0211504 A1 | 11/2003 | Fechtel et al. |
| 2004/0053251 A1 | 3/2004 | Pericak-Vance et al. |
| 2004/0086888 A1 | 5/2004 | Kornblith et al. |
| 2004/0115701 A1 | 6/2004 | Comings et al. |
| 2004/0142325 A1 | 7/2004 | Mintz et al. |
| 2004/0146870 A1 | 7/2004 | Liao et al. |
| 2004/0161779 A1 | 8/2004 | Gingeras |
| 2004/0175700 A1 | 9/2004 | Geesaman |
| 2004/0219567 A1 | 11/2004 | Califano et al. |
| 2004/0248092 A1 | 12/2004 | Vance et al. |
| 2004/0249677 A1 | 12/2004 | Datta et al. |
| 2004/0267458 A1 | 12/2004 | Judson et al. |
| 2005/0019787 A1 | 1/2005 | Berno et al. |
| 2005/0064408 A1 | 3/2005 | Sevon et al. |
| 2005/0086035 A1 | 4/2005 | Peccoud et al. |
| 2005/0176031 A1 | 8/2005 | Sears et al. |
| 2005/0191731 A1 | 9/2005 | Judson et al. |
| 2005/0214811 A1 | 9/2005 | Margulies et al. |
| 2005/0250098 A1 | 11/2005 | Toivonen et al. |
| 2005/0256649 A1 | 11/2005 | Roses |
| 2005/0272057 A1 | 12/2005 | Abrahamsen et al. |
| 2006/0173663 A1 | 8/2006 | Langheier et al. |
| 2006/0286566 A1 | 12/2006 | Lapidus et al. |
| 2007/0027636 A1 | 2/2007 | Rabinowitz |
| 2007/0042369 A1 | 2/2007 | Reese et al. |
| 2007/0082353 A1 | 4/2007 | Hiraoka et al. |
| 2007/0112585 A1 | 5/2007 | Breiter et al. |
| 2007/0174253 A1 | 7/2007 | Hodnett et al. |
| 2007/0196850 A1 | 8/2007 | Kennedy et al. |
| 2007/0276610 A1 | 11/2007 | Korenberg |
| 2008/0091358 A1 | 4/2008 | Taylor |
| 2008/0281818 A1 | 11/2008 | Tenenbaum et al. |
| 2008/0311574 A1 | 12/2008 | Manne et al. |
| 2009/0011407 A1 | 1/2009 | Liu et al. |
| 2009/0012928 A1 | 1/2009 | Lussier et al. |
| 2009/0035279 A1 | 2/2009 | Thorleifsson et al. |
| 2009/0125246 A1 | 5/2009 | Ruiz Laza |
| 2009/0137402 A1 | 5/2009 | Wang et al. |
| 2009/0181380 A1 | 7/2009 | Belouchi et al. |
| 2009/0198519 A1 | 8/2009 | McNamar |
| 2009/0240441 A1 | 9/2009 | Lapidus |
| 2009/0299645 A1 | 12/2009 | Colby et al. |
| 2010/0114956 A1 | 5/2010 | McElfresh et al. |
| 2010/0130526 A1 | 5/2010 | Glinsky |
| 2010/0143921 A1 | 6/2010 | Sadee et al. |
| 2010/0184037 A1 | 7/2010 | Plass et al. |
| 2010/0216655 A1 | 8/2010 | Sulem |
| 2010/0317726 A1 | 12/2010 | Figg et al. |
| 2011/0004616 A1 | 1/2011 | Miyao |
| 2011/0014607 A1 | 1/2011 | Jirtle et al. |
| 2011/0020320 A1 | 1/2011 | Gudmundsson et al. |
| 2011/0045997 A1 | 2/2011 | Hernandez et al. |
| 2011/0111419 A1 | 5/2011 | Stefansson et al. |
| 2011/0202486 A1 | 8/2011 | Fung et al. |
| 2011/0212855 A1 | 9/2011 | Rafnar et al. |
| 2011/0230366 A1 | 9/2011 | Gudmundsson et al. |
| 2011/0251243 A1 | 10/2011 | Tucker et al. |
| 2011/0257896 A1 | 10/2011 | Dowds et al. |
| 2011/0287946 A1 | 11/2011 | Gudmundsson et al. |
| 2012/0010866 A1 | 1/2012 | Ramnarayan |
| 2012/0016594 A1 | 1/2012 | Christman et al. |
| 2012/0078901 A1 | 3/2012 | Conde |
| 2012/0109615 A1 | 5/2012 | Yun et al. |
| 2012/0110013 A1 | 5/2012 | Conde et al. |
| 2012/0122698 A1 | 5/2012 | Stacey et al. |
| 2012/0143512 A1 | 6/2012 | Reese et al. |
| 2012/0173153 A1 | 7/2012 | Elango et al. |

(56) References Cited

U.S. PATENT DOCUMENTS

| | | |
|---|---|---|
| 2012/0191366 A1 | 7/2012 | Pearson et al. |
| 2012/0215459 A1 | 8/2012 | Stef et al. |
| 2012/0215463 A1 | 8/2012 | Brodzik |
| 2012/0231959 A1 | 9/2012 | Elton et al. |
| 2012/0310539 A1 | 12/2012 | Crockett et al. |
| 2012/0330559 A1 | 12/2012 | Jiang et al. |
| 2013/0035864 A1 | 2/2013 | Stupp et al. |
| 2013/0039548 A1 | 2/2013 | Nielsen et al. |
| 2013/0080365 A1 | 3/2013 | Dewey et al. |
| 2013/0090859 A1 | 4/2013 | Palsson et al. |
| 2013/0184161 A1 | 7/2013 | Kingsmore et al. |
| 2013/0184999 A1 | 7/2013 | Ding |
| 2013/0212125 A1 | 8/2013 | Wierenga et al. |
| 2013/0224739 A1 | 8/2013 | Thorleifsson et al. |
| 2013/0226468 A1 | 8/2013 | Skinner et al. |
| 2013/0226621 A1 | 8/2013 | Van Der Zaag et al. |
| 2013/0245958 A1 | 9/2013 | Forster et al. |
| 2013/0246033 A1 | 9/2013 | Heckerman et al. |
| 2013/0259847 A1 | 10/2013 | Vishnudas et al. |
| 2013/0261984 A1 | 10/2013 | Eberle et al. |
| 2013/0273543 A1 | 10/2013 | Gudmundsson et al. |
| 2013/0296175 A1 | 11/2013 | Rafnar et al. |
| 2013/0296193 A1 | 11/2013 | Choi et al. |
| 2013/0297221 A1 | 11/2013 | Johnson et al. |
| 2013/0309666 A1 | 11/2013 | Deciu et al. |
| 2013/0316915 A1 | 11/2013 | Halpern et al. |
| 2013/0332081 A1 | 12/2013 | Reese et al. |
| 2013/0338012 A1 | 12/2013 | Sulem et al. |
| 2013/0345066 A1 | 12/2013 | Brinza et al. |
| 2014/0024029 A1 | 1/2014 | Mrazek |
| 2014/0040264 A1 | 2/2014 | Varadan et al. |
| 2014/0046696 A1 | 2/2014 | Higgins et al. |
| 2014/0046926 A1 | 2/2014 | Walton |
| 2014/0066317 A1 | 3/2014 | Talasaz |
| 2014/0067355 A1 | 3/2014 | Noto et al. |
| 2014/0087961 A1 | 3/2014 | Sulem et al. |
| 2014/0088942 A1 | 3/2014 | Li et al. |
| 2014/0089009 A1 | 3/2014 | Van Criekinge et al. |
| 2014/0100792 A1 | 4/2014 | Deciu et al. |
| 2014/0114582 A1 | 4/2014 | Mittelman et al. |
| 2014/0114584 A1 | 4/2014 | Bruestle |
| 2014/0115515 A1 | 4/2014 | Adams et al. |
| 2014/0143188 A1 | 5/2014 | Mackey et al. |
| 2014/0153801 A1 | 6/2014 | Sarkozy et al. |
| 2014/0200824 A1 | 7/2014 | Pancoska |
| 2014/0206006 A1 | 7/2014 | Xu et al. |
| 2014/0214331 A1 | 7/2014 | Kowalczyk et al. |
| 2014/0214333 A1 | 7/2014 | Plattner et al. |
| 2014/0214334 A1 | 7/2014 | Plattner et al. |
| 2014/0222349 A1 | 8/2014 | Higgins et al. |
| 2014/0229117 A1 | 8/2014 | Halpern et al. |
| 2014/0229495 A1 | 8/2014 | Makkapati et al. |
| 2014/0235456 A1 | 8/2014 | Garner, Jr. et al. |
| 2014/0244556 A1 | 8/2014 | Saleh et al. |
| 2014/0247184 A1 | 9/2014 | Wendel |
| 2014/0248692 A1 | 9/2014 | Lagace et al. |
| 2014/0249764 A1 | 9/2014 | Kumar et al. |
| 2014/0274745 A1 | 9/2014 | Chen et al. |
| 2014/0278133 A1 | 9/2014 | Chen et al. |
| 2014/0278461 A1 | 9/2014 | Artz |
| 2014/0287934 A1 | 9/2014 | Szelinger et al. |
| 2014/0303901 A1 | 10/2014 | Sadeh |
| 2014/0310215 A1 | 10/2014 | Trakadis |
| 2014/0350954 A1 | 11/2014 | Ellis et al. |
| 2014/0359422 A1 | 12/2014 | Bassett, Jr. et al. |
| 2014/0365243 A1 | 12/2014 | Varadan et al. |
| 2014/0372953 A1 | 12/2014 | Laurance |
| 2015/0024948 A1 | 1/2015 | Dugas et al. |
| 2015/0046191 A1 | 2/2015 | Futscher de Deus et al. |
| 2015/0051116 A1 | 2/2015 | Kim |
| 2015/0056619 A1 | 2/2015 | Li et al. |
| 2015/0066381 A1 | 3/2015 | Kural |
| 2015/0066385 A1 | 3/2015 | Schnall-Levin et al. |
| 2015/0073719 A1 | 3/2015 | Glynias et al. |
| 2015/0073724 A1 | 3/2015 | Ashutosh et al. |
| 2015/0081323 A1 | 3/2015 | Jackson et al. |
| 2015/0095064 A1 | 4/2015 | Schols |
| 2015/0105267 A1 | 4/2015 | Shendure et al. |
| 2015/0105270 A1 | 4/2015 | Floratos |
| 2015/0120322 A1 | 4/2015 | Hoffman et al. |
| 2015/0142331 A1 | 5/2015 | Beim et al. |
| 2015/0169828 A1 | 6/2015 | Spector |
| 2015/0178445 A1 | 6/2015 | Cibulskis et al. |
| 2015/0186596 A1 | 7/2015 | Chakrabarti et al. |
| 2015/0193578 A1 | 7/2015 | Kiel et al. |
| 2015/0197785 A1 | 7/2015 | Carter et al. |
| 2015/0199472 A1 | 7/2015 | Kural |
| 2015/0199473 A1 | 7/2015 | Kural |
| 2015/0199474 A1 | 7/2015 | Kural |
| 2015/0199475 A1 | 7/2015 | Kural |
| 2015/0205914 A1 | 7/2015 | Richards et al. |
| 2015/0220687 A1 | 8/2015 | An |
| 2015/0227697 A1 | 8/2015 | Nelson et al. |
| 2015/0228041 A1 | 8/2015 | Naley et al. |
| 2015/0247184 A1 | 9/2015 | Vermeesch et al. |
| 2015/0248522 A1 | 9/2015 | Guturu et al. |
| 2015/0248525 A1 | 9/2015 | Ury et al. |
| 2015/0254397 A1 | 9/2015 | Rogan et al. |
| 2015/0261913 A1 | 9/2015 | Dewey et al. |
| 2015/0294063 A1 | 10/2015 | Kalalakaran et al. |
| 2015/0310163 A1 | 10/2015 | Kingsmore et al. |
| 2015/0310165 A1 | 10/2015 | Mann |
| 2015/0310228 A1 | 10/2015 | Benz et al. |
| 2015/0315645 A1 | 11/2015 | Gaasterland et al. |
| 2015/0317432 A1 | 11/2015 | Silver et al. |
| 2015/0324519 A1 | 11/2015 | Liu |
| 2015/0347676 A1 | 12/2015 | Zhao et al. |
| 2015/0356243 A1 | 12/2015 | Andreassen et al. |
| 2015/0363549 A1 | 12/2015 | Kimura |
| 2015/0367145 A1 | 12/2015 | Sjolund et al. |
| 2015/0376700 A1 | 12/2015 | Schnall-Levin et al. |
| 2015/0379193 A1 | 12/2015 | Bassett, Jr. et al. |
| 2016/0004814 A1 | 1/2016 | Stamatoyannopoulos |
| 2016/0017412 A1 | 1/2016 | Srinivasan et al. |
| 2016/0024591 A1 | 1/2016 | Xu et al. |
| 2016/0026753 A1 | 1/2016 | Krishnaswami et al. |
| 2016/0026772 A1 | 1/2016 | Plante et al. |
| 2016/0034667 A1 | 2/2016 | Rosenblatt et al. |
| 2016/0040239 A1 | 2/2016 | Sadee et al. |
| 2016/0048608 A1 | 2/2016 | Frieden et al. |
| 2016/0070854 A1 | 3/2016 | Wong et al. |
| 2016/0070855 A1 | 3/2016 | Sanborn et al. |
| 2016/0078094 A1 | 3/2016 | Popescu et al. |
| 2016/0078169 A1 | 3/2016 | Namkung et al. |
| 2016/0092631 A1 | 3/2016 | Yandell et al. |
| 2016/0098519 A1 | 4/2016 | Zwir |
| 2016/0103919 A1 | 4/2016 | Boyce |
| 2016/0140289 A1 | 5/2016 | Gibiansky et al. |
| 2016/0153032 A9 | 6/2016 | Rosenthal et al. |
| 2016/0154928 A1 | 6/2016 | Zeskind et al. |
| 2016/0186253 A1 | 6/2016 | Talasaz et al. |
| 2016/0196382 A1 | 7/2016 | Kim et al. |
| 2016/0201134 A1 | 7/2016 | Liao et al. |
| 2016/0203196 A1 | 7/2016 | Schnall-Levin et al. |
| 2016/0203287 A1 | 7/2016 | Chen et al. |
| 2016/0210401 A1 | 7/2016 | Kim et al. |
| 2016/0224722 A1 | 8/2016 | Reese et al. |
| 2016/0224730 A1 | 8/2016 | Yu et al. |
| 2016/0232291 A1 | 8/2016 | Kyriazopoulou-Panagiotopoulou et al. |
| 2016/0239603 A1 | 8/2016 | Brown |
| 2016/0253452 A1 | 9/2016 | Karbassi et al. |
| 2016/0253770 A1 | 9/2016 | Downs et al. |
| 2016/0259880 A1 | 9/2016 | Semenyuk |
| 2016/0259886 A1 | 9/2016 | Li et al. |
| 2016/0273049 A1 | 9/2016 | Velculescu et al. |
| 2016/0281166 A1 | 9/2016 | Bhattacharjee et al. |
| 2016/0283407 A1 | 9/2016 | Van Rooyen et al. |
| 2016/0283484 A1 | 9/2016 | Chandratillake et al. |
| 2016/0298185 A1 | 10/2016 | Shukla et al. |
| 2016/0300012 A1 | 10/2016 | Barber et al. |
| 2016/0300013 A1 | 10/2016 | Ashutosh et al. |
| 2016/0300921 A1 | 10/2016 | Kural |
| 2016/0314245 A1 | 10/2016 | Silver et al. |

(56) References Cited

U.S. PATENT DOCUMENTS

| | | |
|---|---|---|
| 2016/0319335 A1 | 11/2016 | Deciu et al. |
| 2016/0333411 A1 | 11/2016 | Harper |
| 2016/0340722 A1 | 11/2016 | Platt |
| 2016/0342732 A1 | 11/2016 | Popovic et al. |
| 2016/0342733 A1 | 11/2016 | Reid et al. |
| 2016/0342737 A1 | 11/2016 | Kaye |
| 2016/0370961 A1 | 12/2016 | Merel |
| 2016/0371429 A1 | 12/2016 | Patil et al. |
| 2016/0371431 A1 | 12/2016 | Haque et al. |
| 2016/0374600 A1 | 12/2016 | Short et al. |
| 2017/0004256 A1 | 1/2017 | Miyashita et al. |
| 2017/0017717 A1 | 1/2017 | Kimura |
| 2017/0017752 A1 | 1/2017 | Noto et al. |
| 2017/0032081 A1 | 2/2017 | Agrawal et al. |
| 2017/0061070 A1 | 3/2017 | Kingsmore et al. |
| 2017/0068826 A1 | 3/2017 | Dimitrova et al. |
| 2017/0073755 A1 | 3/2017 | Tiwari et al. |
| 2017/0076046 A1 | 3/2017 | Barnes et al. |
| 2017/0076050 A1 | 3/2017 | Soon-Shiong |
| 2017/0091382 A1 | 3/2017 | Yun et al. |
| 2017/0098053 A1 | 4/2017 | Pandey et al. |
| 2017/0107576 A1 | 4/2017 | Babiarz et al. |
| 2017/0109471 A1 | 4/2017 | Ariyaratne et al. |
| 2017/0116379 A1 | 4/2017 | Scott et al. |
| 2017/0132357 A1 | 5/2017 | Brewerton et al. |
| 2017/0132362 A1 | 5/2017 | Skinner et al. |
| 2017/0154154 A1 | 6/2017 | Daly et al. |
| 2017/0169160 A1 | 6/2017 | Hu et al. |
| 2017/0169163 A1 | 6/2017 | Shomron et al. |
| 2017/0175206 A1 | 6/2017 | Xu et al. |
| 2017/0198348 A1 | 7/2017 | Namkung |
| 2017/0199960 A1 | 7/2017 | Ghose et al. |
| 2017/0202519 A1 | 7/2017 | Kuo |
| 2017/0211205 A1 | 7/2017 | Murray |
| 2017/0213011 A1 | 7/2017 | Hoffman et al. |
| 2017/0213127 A1 | 7/2017 | Duncan |
| 2017/0286594 A1 | 10/2017 | Reid et al. |

FOREIGN PATENT DOCUMENTS

| | | |
|---|---|---|
| WO | WO-2013/102441 A1 | 7/2013 |
| WO | WO-2014/121128 A1 | 8/2014 |
| WO | WO-2014/145234 A2 | 9/2014 |
| WO | WO-2014/145503 A2 | 9/2014 |
| WO | WO-2015/013191 A1 | 1/2015 |
| WO | WO-2015/051163 A2 | 4/2015 |
| WO | WO-2015/148776 A1 | 10/2015 |
| WO | WO-2015/173435 A1 | 11/2015 |
| WO | WO-2015/191562 A1 | 12/2015 |
| WO | WO-2015184404 A1 | 12/2015 |
| WO | WO-2016/038220 A1 | 3/2016 |
| WO | WO-2016/055971 A2 | 4/2016 |
| WO | WO-2016/061570 A1 | 4/2016 |
| WO | WO-2016/062713 A1 | 4/2016 |
| WO | WO-2016/064995 A1 | 4/2016 |
| WO | WO-2016/083949 A1 | 6/2016 |
| WO | WO-2016/122318 A1 | 8/2016 |
| WO | WO-2016/124600 A1 | 8/2016 |
| WO | WO-2016/139534 A2 | 9/2016 |
| WO | WO-2016/141127 A1 | 9/2016 |
| WO | WO-2016/141214 A1 | 9/2016 |
| WO | WO-2016/154254 A1 | 9/2016 |
| WO | WO-2016/154584 A1 | 9/2016 |
| WO | WO-2016/172801 A1 | 11/2016 |
| WO | WO-2016/179049 A1 | 11/2016 |
| WO | WO-2016/183659 A1 | 11/2016 |
| WO | WO-2016/187051 A1 | 11/2016 |
| WO | WO-2016/201564 A1 | 12/2016 |
| WO | WO-2016/203457 A1 | 12/2016 |
| WO | WO-2017/009372 A2 | 1/2017 |
| WO | WO-2017/024138 A1 | 2/2017 |
| WO | WO-2017/042831 A2 | 3/2017 |
| WO | WO-2017/049214 A1 | 3/2017 |
| WO | WO-2017/064142 A1 | 4/2017 |
| WO | WO-2017/065959 A2 | 4/2017 |
| WO | WO-2017/100794 A1 | 6/2017 |
| WO | WO-2017/116123 A1 | 7/2017 |
| WO | WO-2017/120556 A1 | 7/2017 |
| WO | WO-2017/139801 A1 | 8/2017 |

OTHER PUBLICATIONS

Mahmud et al., "Fast MCMC sampling for hidden markov models to determine copy number variations" BMC Bioinformatics 2011 12:428.

Kd-trees CMSC 420 (2014) [retrieved on Jan. 19, 2018] Retrieved from the internet <URL: https://www.cs.cmu.edu/-ckingsf/u bioinfo-lectures/kdtrees.pdf>.

K-d tree, Wikipedia (2018) [retrieved on Apr. 25, 2018] Retrieved from the internet <URL: https://en.wikipedia.org/wiki/K-d_tree>.

Response to Non Final was mailed on Oct. 23, 2017 to the USPTO for U.S. Appl. No. 14/714,949, filed May 18, 2015, and published as US 2016-0342733 A1 on Nov. 24, 2016 (Applicant-Jeffrey Reid ) (30 pages).

Final Rejection was issued on Jan. 25, 2018 by the USPTO for U.S. Appl. No. 14/714,949, filed May 18, 2015, and published as US 2016-0342733 A1 on Nov. 24, 2016 (Applicant—Jeffrey Reid ) (10 pages).

U.S. Appl. No. 14/714,949 (2016/0342733), filed May 18, 2015 (Nov. 24, 2016), Jeffrey Reid et al. (Regeneron Pharmaceuticals, Inc.).

U.S. Appl. No. 62/294,669, filed Feb. 12, 2016, Evan Maxwell et al. (Regeneron Pharmaceuticals, Inc.).

U.S. Appl. No. 62/314,684, filed Mar. 29, 2016, Jeffrey Reid et al. (Regeneron Pharmaceuticals, Inc.).

U.S. Appl. No. 62/362,660, filed Jul. 15, 2016, Jeffrey Reid et al. (Regeneron Pharmaceuticals, Inc.).

U.S. Appl. No. 62/4404,912, filed Oct. 6, 2016, Jeffrey Reid et al. (Regeneron Pharmaceuticals, Inc.)

U.S. Appl. No. 62/467,547, filed Mar. 6, 2017, Jeffrey Reid et al. (Regeneron.

U.S. Appl. No. 15/473,302 (2017/0286594), filed Mar. 29, 2017 (Oct. 5, 2017), Jeffrey Reid et al. (Regeneron Pharmaceuticals, Inc.).

PCT, PCT/US2016/032484 (WO 2016/187051), May 13, 2016 (Nov. 24, 2016,), Jeffrey Reid et al. (Regeneron Pharmaceuticals, Inc.).

PCT, PCT/US2017/017734 (WO 2017/139801), Feb. 13, 2017 (Aug. 17, 2017), Evan Maxwell et al. (Regeneron Pharmaceuticals, Inc.).

PCT, PCT/US2017/024810 (WO 2017/172958), Mar. 29, 2017 (Oct. 5, 2017), Jeffrey Reid et al. (Regeneron Pharmaceuticals, Inc.).

International Search Report and Written Opinion mailed on Jul. 21, 2017 by the International Searching Authority for International Patent Application No. PCT/US2017/017734, which was filed on Feb. 13, 2017 and published as WO 2017/139801 on Aug. 17, 2017 (Inventor—Maxwell et al.; Applicant—Regeneron Pharmaceuticals, Inc.; (13 pages).

Office Action was issued on Nov. 26, 2019 by the Japanese Patent Office for JP Application No. 2018-542281, filed on Feb. 13, 2017 and published as JP 2019-512122 on May 9, 2019 (Applicant—Regeneron Pharmaceuticals, Inc.) (Original—3 Pages //Translation—3 Pages).

Office Action was issued on Jan. 21, 2020 by the Japanese Patent Office for JP Application No. 2017-559843, filed on May 13, 2016 and published as JP 2018-523198 on Aug. 16, 2018 (Applicant—Regeneron Pharmaceuticals, Inc.) (Original—4 Pages //Translation—3 Pages).

Office Action was issued on Feb. 3, 2020 by the Russian Patent Office for RU Application No. 2017143983, filed on May 13, 2016 (Applicant—Regeneron Pharmaceuticals, Inc.) (4 Pages).

Office Action was issued on Sep. 24, 2020 by the New Zealand Patent Office for NZ Application No. 745249, filed on Feb. 13, 2017 (Applicant—Regeneron Pharmaceuticals, Inc.) (5 pages).

Van Steenhouse, "Identifying Chromosomal Abnormalities Using Infinium SNP BeadChips," p. 1-21, Sep. 2010.

(56) References Cited

OTHER PUBLICATIONS

Weissbein et al. "Analysis of chromosomal aberrations and recombination by allelic bias in RNA-Seq," Nature Communications, 7:121444, p. 1-8, Jul. 7, 2016.
Office Action was issued on May 31, 2020 by the Israeli Patent Office for IL Application No. 261216, filed on Feb. 13, 2017 (Applicant—Regeneron Pharmaceuticals, Inc.) (Original—3 Pages //Translation—3 Pages).
Office Action was issued on Feb. 5, 2021 by the Canadian Patent Office for CA Application No. 3018186, filed on Mar. 29, 2017 (Applicant—Regeneron Pharmaceuticals, Inc.) (4 pages).
Backenroth et al. (2014) CANOES: detecting rare copy number variants from whole exome sequencing data. Nucleic Acids Res. 42(12): e97 (9 pages).
Baigent, S. et al., Efficacy and Safety of Cholesterol-Lowering Treatment: Prospective Meta-Analysis of Data from 90,056 Participants in 14 Randomised Trials of Statins. Lancet. 2005; 366(9493): 1267-78.
Benjamini, Yuval, and Speed, Terence P. (2012) Summarizing and correcting the GC content bias in high-throughput sequencing, Nucleic Acids Res, 40 (10): e72 (14 pages).
Benn, M. et al., PCSK9 R46L, Low-Density Lipoprotein Cholesterol Levels, and Risk of Ischemic Heart Disease. J Am Coll Cardiol. 2010; 55:2833-42.
Berg, J.S. et al., An Informatics Approach to Analyzing the Incidentalome. Genet Med. 2013; 15(1):36-44.
Blekhman, R. et al., Natural Selection on Genes that Underline Human Disease Susceptibility. Curr Biol. 2008; 18(12):883-9.
Boettger, L.M. et al., Recurring Exon Deletions in the HP (haptoglobin) Gene Contribute to Lower Blood Cholesterol Levels. Nat Genet. 2016; 48:359-66.
Brand, H. et al., Paired-Duplication Signatures Mark Cryptic Inversions and Other Complex Structural Variation. Am J Hum Genet. 2015; 97(1):170-6.
Brundert, M. et al., Scavenger Receptor CD36 Mediates Uptake of High Density Lipoproteins in Mice and by Cultured Cells. J Lipid Res. 2011; 52(4):745-58.
Carey et al., The Geisinger MyCode Community Health Initiative: an Electronic Health Record-Linked Biobank for Precision Medicine Research. Genes in Medicine. 2016; 18(9):906-13.
Carvalho et al., Inverted Genomic Segments and Complex Triplication Rearrangements are mediated by Inverted Repeats in the Human Genome. Nat Genet. 2011; 43(11):1074-81.
Chance, P.F. et al., DNA Deletion Associated with Hereditary Neuropathy with Liability to Pressure Palsies. Cell. 1993; 72(1):143-51.
Chance, P.F. et al., Two Autosomal Dominant Neuropathies Result from Reciprocal DNA Duplication/Deletion of a Region on Chromosome 17. Hum Mol Genet. 1994; 3:223-8.
Chang, C.C. et al., Second-Generation PLINK: Rising to the Challenge of Larger and Richer Datasets. Gigascience. 2015; 4:7 (16 pages).
Choi, M. et al., Genetic Diagnosis by Whole Exome Capture and Massively Parallel DNA Sequencing. Proc Natl Acad Sci USA. 2009; 106(45):19096-101.
Chong, J.X. et al., The Genetic Basis of Mandelian Phenotypes: Discoveries, Challenges, and Opportunities. Am J Hum Genet. 2015; 97(2):199-215.
Chou, J.Y et al., Type I Glycogen Storage Diseases: Disorders of the Glucose-6-Phosphatase Complex. Curr Mol Med. 2002; 2(2):121-43.
Cingolani, P. et al., A Program for Annotating and Predicting the Effects of Single Nucleotide Polymorphisms, SnpEff. Fly (Austin). 2012; 6(2):80-92.
Coe et al. (2014) Refining analyses of copy number variation identities specific genes associated with developmental delay. Nat Genet, 46 (10): 1063-71.
Cohen, J.C. et al., Sequence Variations in PCCK9, Low LDL, and Protection Against Coronary Heart Disease. N Engl J Med. 2006; 354(12): 1264-72.

Conrad, D.F. et al., Origins and Functional Impact of Copy Number variation in the Human Genome. Nature. 2010; 464(7289):704-12.
Coram, M.A., Genome-wide Characterization of Shared and Distant Genetic Components that Influence Blood Lipid Levels in Ethnically Diverse Human Populations. Am J Hum Genet. 2013; 92:904.
De Cid, R. et al., Deletion of the Late Cornified Envelope (LCE) 3B and 3C Genes as a Susceptibility Factor for Psoriasis. Nat Genet. 2009; 41(2):211-5.
Denny, J.C. et al., Systematic Comparison of Phenome-wide Association Study of Electronic Medical Record Data and Genome-wide Association Study Data. Nature Biotechnol. 2013; 31(12):1102-11.
DiVincenzo, C. et al., The Allelic Spectrum of Charcot-Marie-Tooth Disease in Over 17,000 Individuals with Neuropathy. Mol Genet Genomic Med. 2014; 2(6):522-9.
Do, R. et al., Exome Sequencing Identifies Rare LDLR and APOA5 Alleles Conferring Risk for Myocardial Infarction. Nature. 2015; 518(7537):102-6.
Elbers, C.C. et al., Gene-Centric Meta-Analysis of Lipid Traits in African, East Asian and Hispanic Populations. PLoS One. 2012; 7(12):e50198 (14 pages).
Ferreira, M.A. and S.M. Purcell, The Multivariate Test of Association. Bioinformatics. 2009; 25(1):132-3.
Fromer et al., (2012) "Discovery and statistical genotyping of copy-number variation from whole-exome sequencing depth," Am J Hum Genet 91 (4), 597-607.
Georgi, B. et al., From Mouse to Human: Evolutionary Genomics Analysis of Human Orthologs of Essential Genes. PLoS Genet. 2013; 9(5):e1003484 (10 pages).
Girirajan, S. et al., A Recurrent 16p12.1 Microdeletion Supports a Two-Hit Model for Severe Developmental Delay. Nat Genet. 2010; 42:203-9.
Gottesman, O. et al., Can Genetic Pleiotropy Replicate Common Clinical Constellations of Cardiovascular Disease and Risk? PLoS One. 2012; 7(9):e46419 (9 pages).
Green, R.C. et al., ACMG Recommendations for Reporting of Incidental Findings in Clinical Exome and Genome Sequencing. Genet Med. 2013; 15(7):565-74.
Gudbjartsson, D.F. et al., Large-Scale Whole-Genome Sequencing of the Icelandic Population. Nat Genet. 2015; 47(5):435-44.
Handsaker et al. (2015) Large multiallelic copy No. variations in humans. Nat Genet, 47 (3), 296-303.
Heinzen, E.L. et al., Rare Deletions at 16p13.11 Predispose to a Diverse Spectrum of Sporadic Epilepsy Syndromes. Am J Hum Genet. 2010; 86(5):707-18.
Hirayasu, K. and H. Arase, Functional and Genetic Diversity of Leukocyte Immunoglobulin-like Receptor and Implication for Disease Associations. J Hum Genet. 2015; 60(11):703-8.
Holm, H. et al., A Rare Variant in MYH6 is Associated with High Risk of Sick Sinus Syndrome. Nat Genet. 2011; 43:316-20.
Hoogendijk, J.E. et al., De-novo Mutation in Hereditary Motor and Sensory Neuropathy Type I. Lancet. 1992; 339(8801):1081-2.
Huff, C.D. et al., Maximum-likelihood Estimation of Recent Shared Ancestry (ERSA). Genome Res. 2011; 21(5):768-74.
Hughes, A.E. et al., A Common CFH Haplotype, with Deletion of CFHR1 and CFHR3, is Associated with Lower Risk of Age-Related Macular Degeneration. Nat Genet. 2006; 38(10):1173.
Kathiresan, S., A PCSK9 Missense Variant Associated with a Reduced Risk of Early-Onset Myocardial Infarction. N Engl J Med. 2008; 358(21):2299-300.
Kloosterman, W.P. et al., Characteristics of De Novo Structural Changes in the Human Genome. Genome Res. 2015; 25:792-801.
Korbel, J.O. et al., Paired-End Mapping Reveals Extensive Structural Variation in the Human Genome. Science. 2007; 318(5849):420-6.
Krumm et al. (2012) Copy number variation detection and genotyping from exome sequence data. Genome Res, 22 (8), 1525-32.
Landrum, M.J. et al., ClinVar: Public Archive of Relationships Among Sequence Variation and Human Phenotype. Nucleic Acids Res. 2014; 42:D980-5.
Lange, L.A. et al., Whole-exome Sequencing Identifies Rare and Low-Frequency Coding Variants Associated with LDL Cholesterol. Am J Hum Genet. 2014; 94(2):233-45.

(56) References Cited

OTHER PUBLICATIONS

Layer, R.M. et al., LUMPY: A Probabilistic Framework for Structural Variant Discovery. Genome Biol. 2014; 15:R84 (19 pages).
Lee, S. et al., Rare-Variant Association Analysis: Study Designs and Statistical Tests. Am J Hum Genet. 2014; 95(1):5-23.
Leigh, S.E. et al., Update and Analysis of the University College London Low Density Lipoprotein Receptor Familial Hypercholesterolemia Database. Ann Hum Genet. 2008; 72(4):485-98.
Lek, M. et al., Analysis of Protein-Coding Genetics Variation in 60,706 Humans. Nature. 2016; 536:285-91.
Li, A.H. et al., Analysis of Loss-of-Function Variants and 20 Risk Factor Phenotypes in 8,554 Individuals Identifies Loci Influencing chronic Disease. Nat Genet. 2015; 47(6):640-2.
Li, B. and S.M. Leal, Methods for Detecting Associations with Rare Variants for Common Diseases: Application to Analysis of Sequence Data. Am J Hum Genet. 2008; 83(3):311-21.
Li, H. and R. Durbin, Fast and Accurate Short Read Alignment with Burrows-Wheeler Transform. Bioinformatics. 2009; 25(14):1754-60.
Li, H. et al., The Sequence Alignment/Map Format and SAMtools. Bioinformatics. 2009; 25(16):2078-9.
Lim, E.T. et al., Distribution and Medical Impact of Loss-of-function Variants in the Finnish Founder Population. PLoS Genet. 2014; 10(7):e1004494 (12 pages).
Liu, P. et al., Mechanisms for Recurrent and Complex Human Genomic Rearrangements. Curr Opin Genet Dev. 2012; 22(3):211-20.
Loh, P.R. et al., Efficient Bayesian Mixed Model Analysis Increases Association Power in Large Cohorts. Nat Genet. 2015; 47(3):284-90.
Lupski, J.R. et al., DNA Duplication Associated with Charcot-Marie-Tooth Disease Type 1A. Cell. 1991; 66(2):219-32.
Lupski, J.R., Structural Variation Mutagenesis of the Human Genome: Impact on Disease and Evolution. Environ Mol Mutagen. 2015; 56(5):419-36.
MacArthur, D.G. et al., A Systematic Survey of Loss-Function Variants in Human Protein-Coding Genes. Science. 2012; 335(6070):823-8.
MacDonald, J.R. et al., The Database of Genomic Variants: a Curated Collection of Structural Variation in the Human Genome. Nucleic Acids Res. 2013; 42(Database Issue):D986-92.
Mahmud, P. et al., Fast MCMC Sampling for Hidden Markov Models to Determine Copy Number Variations. BMC Bioinformatics. 2011; 12(1):428 (17 pages).
McCarthy, S.E. et al., Microduplications of 16p11.2 are Associated with Schizophrenia. Nat Genet. 2009; 41(11):1223-7.
McKenna, A. et al., The Genome Analysis Toolkit: A MapReduce Framework for Analyzing Next-Generation DNA Sequencing Data. Genome Res. 2010; 20(9):1297-303.
Mefford, H.C. et al., Recurrent Rearrangements of Chromosome 1q21.1 and Variable Pediatric Phenotypes. N Engl J Med. 2008; 359:1685-99.
Meretoja, P. et al., Epidemiology of Hereditary Neuropathy with Liability to Pressure Palsies (HNPP) in South Western Finland. Neuromuscul Disord. 1997; 7(8):529-32.
Mills, R.E. et al., Mapping Copy Number Variation by Population-Scale Genome Sequencing. Nature. 2011; 470: 59-65.
Myocardial Infarction Genetics Consortium Investigators, Inactivating Mutations in NPC1L1 and Protection from Coronary Heart Disease. N Engl J Med. 2014; 371:2072.
Newman, S. et al., Next-Generation Sequencing of Duplication CNVs reseals that Most Are Tandem and Some Create Fusion Genes in Breakpoints. Am J Hum Genet. 2015; 96(2):208.
O'Dushlaine, C.T. et al., Population Structure and Genome-Wide Patterns of Variation in Ireland and Britain. Eur J Hum Genet. 2010; 18(11):1248-54.
Ordóñez, D. et al., Multiple Sclerosis Associates with *LILRA3* Deletion in Spanish Patients. Genes and Immunity. 2009; 10:579.

Pabinger, S. et al.; A Survey of Tools for Variant Analysis of Next-Generation Genome Sequencing Data. Briefings Bioinformatics. 2013; 15(2):256-78.
Packer, J.S. et al., CLAMMS: A Scalable Algorithm for Calling Common and Rare Copy Number Variants from Exome Sequencing Data. Bioinformatics. 2016; 32(1):133-5.
Packer, J.S. et al., Supplementary Materials for CLAMMS: A Scalable Algorithm for Calling Common and Rare Copy Number Variants from Exome Sequencing Data. Bioinformatics Advance Access. 2015 (24 pages).
Peloso, G.M. et al., Association of Low-Frequency and Rare Coding-Sequence Variants with Blood Lipids and Coronary Heart Disease in 56,000 Whites and Blacks. Am J Hum Genet. 2014; 94(2):223.
Pinto, D. et al., Comprehensive Assessment of Array-Based Platforms and Calling Algorithms for Detection of Copy Number Variants. Nature Biotechnol. 2011; 29(6):512-20.
Plagnol et al. (2012) A robust model for read count data in exome sequencing experiments and implications for copy number variant calling. Bioinformatics, 28 (21), 2747-54.
Pollin, T.I. et al., A Null Mutation in Human APOC3 Confers a Favorable Plasma Lipid Profile and Apparent Cardioprotection. Science. 2008; 322(5908):1702-5.
Psaty, B.M. et al., Cohorts for Heart and Aging Research in Genomic Epidemiology (CHARGE) Consortium. Circulation: Cardiovascular Genetics. 2009; 2(1): 73-80.
Raal, F.J., Mipomersen, an Apolipoprotein B Synthesis Inhibitor, for Lowering of LDL Cholesterol Concentrations in Patients with Homozygous Familial Hypercholesterolaemia: A Randomised, Double-Blind, Placebo-Controlled Trial. Lancet. 2010; 375(9719): 998-1006.
Rahman, N., Realizing the Promise of Cancer Predisposition Genes. Nature. 2014; 505(7483): 302-8.
Reid, J.G. et al., Launching Genomics into the Cloud: Deployment of Mercury, a Next Generation Sequence Analysis Pipeline. BMC Bioinformatics. 2014; 15:30 (11 pages).
Richards, S. et al., Standards and Guidelines for the Interpretation of Sequence Variants: A Joint Consensus Recommendation of the American College of Medical Genetics and Genomics and the Association for Molecular Pathology. Genet Med. 2015; 17(5):405-24.
Sham, P.C. and Purcell, S.M., Statistical Power and Significance Testing in Large-Scale Genetic Studies. Nature Rev Genet. 2014; 15(5):335-46.
Skre, H., Genetic and Clinical Aspects of Charcot-Marie-Tooth's Disease. Clin Genet. 1974; 6(2): 98-118.
Staples, J. et al., PRIMUS: Rapid Reconstruction of Pedigrees from Genome-wide Estimates of Identity by Descent. Am J Hum Genet. 2014; 95(5): 553-64.
Steinberg, S. et al., Loss-of-Function Variants in ABCA7 Confer Risk of Alzheimer's Disease. Nat Genet. 2015; 47(5):445-7.
Stenson et al. (2012) The Human Gene Mutation Database (HGMD) and its exploitation in the fields of personalized genomics and molecular evolution. Curr Protoc Bioinformatics. doi: 10.1002/0471250953.bi0113s39.
Sudmant, P.H. et al., An Integrated Map of Structural Variation in 2,504 Human Genomes. Nature. 2015; 526(7571):75-81.
Sulem, P. et al., Identification of a Large Set of Rare Complete Human Knockouts. Nat Genet. 2015; 47(5):448-52.
Surakka et al., The Impact of Low-Frequency and Rare Variants on Lipid Levels. Nat Genet. 2015; 47(6):589-97.
Szigeto, K. and J.R. Lupski, Charcot-Marie-Tooth Disease. Eur J Hum Genet. 2009; 17(6):703-10.
Tennessen, J.A. et al., Evolution and Functional Impact of Rare Coding Variation from Deep Sequencing of Human Exomes. Science. 2012; 337(6090):64-9.
Teslovich, T.M. et al., Biological, Clinical and Population Relevance of 95 Loci for Blood Lipids. Nature. 2010; 466(7307): 707-13.
The 1000 Genomes Project Consortium et al., An Integrated Map of Genetic Variation from 1,092 Human Genomes. Nature. 2012; 491(7422):56-65.

(56) References Cited

OTHER PUBLICATIONS

The 1000 Genomes Project Consortium, A Map of Human Genome Variation from Population-Scale Sequencing. Nature. 2010; 467(7319):1061-73.
The UK10K Consortium, The UK10K Project Identifies Rare Variants in Health and Disease. Nature. 2015; 526(7571):82-90.
Thomas, G.S. et al., Mipomersen, an Apolipoprotein B Synthesis Inhibitor, Reduces Atherogenic Lipoproteins in Patients with Severe Hypercholesterolemia at High Cardiovascular Risk. J Am Coll Cardiol. 2013; 62(23): 2178-84.
Turner, D.J. et al., Gremline Rates of de Novo Meiotic Deletions and Duplications Causing Several Genomic Disorders. Nat Genet. 2008; 40(1): 90-5.
Valenzuela et al., High-throughput Engineering of the Mouse Genome Coupled with High-resolution Expression Analysis. Nat Biotechnol. 2003; 21(6): 652-9.
van bon, B.W. et al., Further Delineation of the 15q13 Microdeletion and Duplication Syndromes: a Clinical Spectrum Varying from Non-Pathogenic to a Severe Outcome. J Med Genet. 2009; 46(8):511-23.
van der Sluis, S. et al., TATES: Efficient Multivariate Genotype-Phenotype Analysis for Genome-Wide Association Studies. PLoS Genetics. 2013; 9(1):e1003235 (9 pages).
Visscher, P.M. et al., Five Years of GWAS Discovery. Am J Hum Genet. 2012; 90(1): 7-24.
Wang et al., Copy Number Variation Detection Using Next Generation Sequencing Read Counts, BMC Bioinformatics, 15: 109 (2014).
Wang, K. et al., PennCNV: An Integrated Hidden Markov Model Designed for High-Resolution Copy Number Variation Detection in Whole-Genome SNP Genotyping Data. Genome Res. 2007; 17(11): 1665-74.
Wellcome Trust Case Control Consortium, Genome-Wide Association Study of 14,000 Cases of Seven Common Diseases and 3,000 Shared Controls. Nature. 2007; 447(7145): 661-78.
Wellcome Trust Case Control Consortium, Genome-Wide Association Study of CNVs in 16,000 Cases of Eight Common Diseases and 3,000 Shared Controls. Nature. 2010; 464: 713-20.
Welty, F.K., Hypobetalipoproteinemia and Abetalipoproteinemia. Curr Opin Lipidol. 2014; 25(3): 161-8.
Wishart, D.S. et al., DrugBank: A Comprehensive Resource for in Silico Drug Discovery and Exploration. Nucleic Acids Res. 2006; 34(Database Issue): D668-72.
Wu, M.C. et al., Rare-Variant Association Testing for Sequencing data with the Sequence Kernet Association Test. Am J Hum Genet. 2011; 89(1): 82-93.
Yang, J. et al., GCTA: A Tool for Genome-wide Complex Trait Analysis. Am J Hum Genet. 2011; 88(1): 76-82.
Yang, Y. et al., Molecular Findings Among Patients Referred for Clinical Whole-Exome Sequencing. JAMA. 2014; 312:1870.
Ye, K. et al., Pindel: A Pattern Growth Approach to Detect Break Points of Large Deletions and Medium Sized Insertions from Paired-end Short Reads. Bioinformatics. 2009; 25(21): 2865-71.
Zhang, F. et al., Copy Number Variation in Human Health, Disease, and Evolution. Annu Rev Genomics Hum Genet. 2009; 10: 451-81.
Zhao, M. et al., Computational Tools for Copy Number Variation (CNV) Detection Using Next-Generation Sequencing Data: Features and Perspectives. BMC Bioinformatics. 2013; 14(Suppl 11): 1-16.
International Search Report and Written Opinion mailed on Aug. 17, 2016 by the International Searching Authority for Patent Application No. PCT/2016/032484, which was filed on May 13, 2016 and published as WO 2016/187051 (Inventor—Reid et al.; Applicant—Regeneron Pharmaceuticals, Inc .; (8 pages).
Non-Final Office Action issued on Jun. 22, 2017 by the U.S. Patent and Trademark Office for U.S. Appl. No. 14/714,949, which was filed on May 18, 2015 and published as US 2016/0342733 on Nov. 24, 2016 (Inventor—Reid et al.; Applicant—Regeneron Pharmaceuticals, Inc.; (9 pages).
International Search Report and Written Opinion mailed on Sep. 4, 2017 for Patent Application No. PCT/US2017/024810, which was filed on Mar. 29, 2017 and published as WO 2017/172958 on Oct. 5, 2017 (Inventor—Reid et al.; Applicant—Regeneron Pharmaceuticals, Inc.; (18 pages).

\* cited by examiner

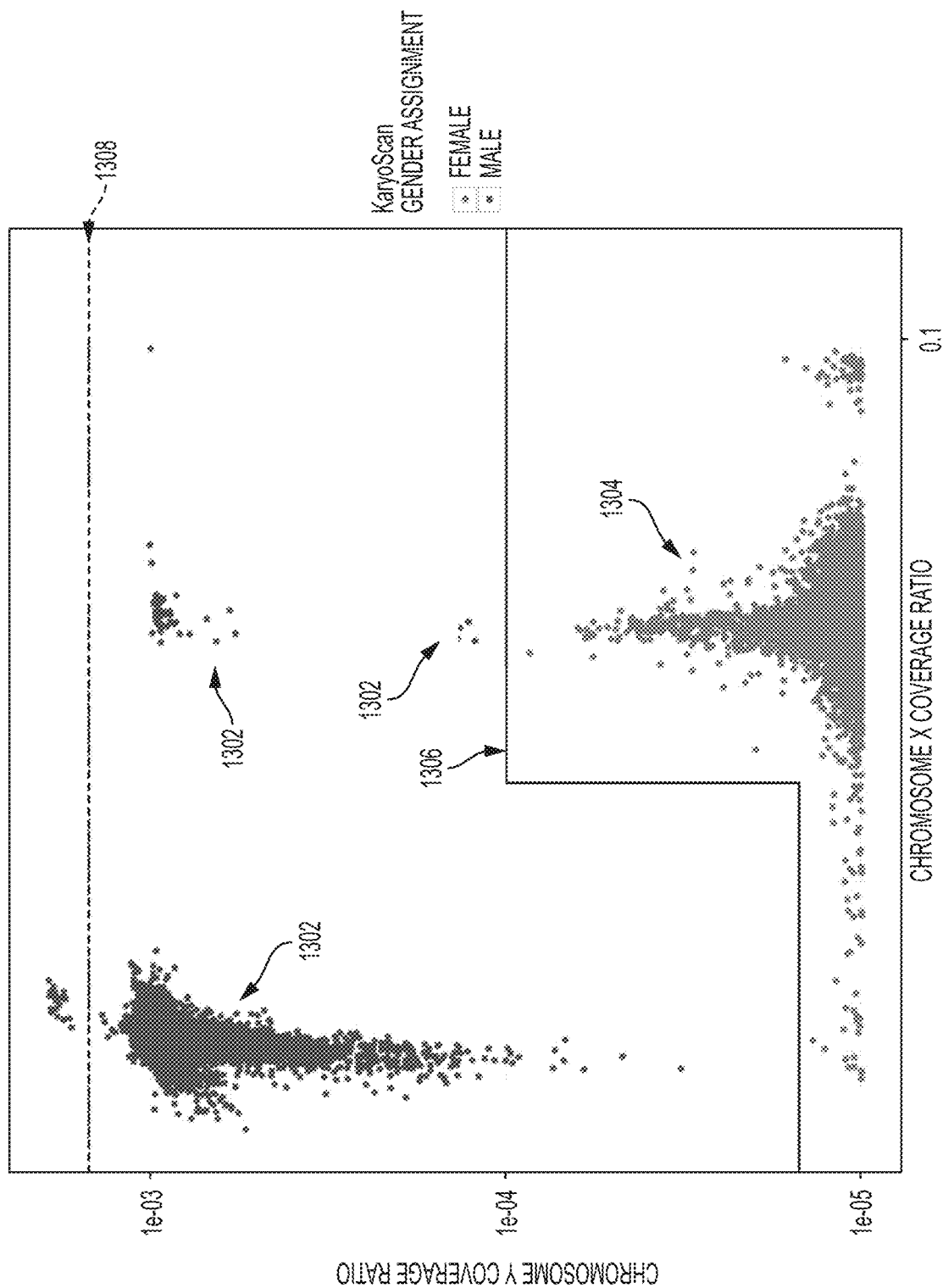

METHODS AND SYSTEMS FOR DETECTION OF ABNORMAL KARYOTYPES

CROSS REFERENCE TO RELATED PATENT APPLICATION

This application claims priority to U.S. Provisional Application No. 62/294,669 filed Feb. 12, 2016, herein incorporated by reference in its entirety.

BACKGROUND

Accurate medical interpretation of human genomic samples requires knowledge of the underlying karyotype. Methods for identifying aberrant karyotypes, such as copy number variants (CNVs), include using DNA microarrays in comparative genomic hybridization (CGH), e.g., using fluorescence in situ hybridization (FISH), clone and PCR-product assays, oligonucleotide arrays, genotyping arrays (Carter N P, Nature Genetics 2007; 39 S16-21)). However, a disadvantage of array technologies is that it can be difficult to define (call) a putative CNV.

Methods for detecting chromosomal abnormalities from next-generation sequencing data are sparse. Certain next-generation sequencing whole-genome copy number variant methods have been utilized, such as read-pair, split-read, read-depth and assembly based methods (Pirooznia, et al., Front. Genet. 2015; 6; 138). However, existing applications have focused on the analysis of very light-skim whole-genome sequencing (WGS) data from maternal plasma samples to detect fractions of aneuploid cell-free fetal DNA for non-invasive prenatal testing (NIPT). Next-generation sequencing has been explored to some extent in cancer genomics, but these analyses generally are based on SNP arrays given the depth of coverage necessary to accurately measure the degree of clonal mosaicism in somatic chromosomal abnormalities.

No existing method has been developed for the purpose of detecting abnormal karyotypes from population-scale whole-exome sequencing (WES) data. These and other shortcomings are addressed in the present disclosure.

SUMMARY

It is to be understood that both the following general description and the following detailed description are exemplary and explanatory only and are not restrictive. Methods and systems for detecting abnormal karyotypes are disclosed. An example method can comprise determining read coverage data, allele balance distributions of heterozygous SNPs, and chromosomal segments where heterozygosity is not observed, for each chromosome in a plurality of samples, wherein each chromosome comprises a plurality of genomic regions, determining expected read coverage data for each chromosome in the plurality of samples, determining a deviation between the read coverage data and the expected read coverage data for at least one chromosome in the plurality of samples, determining a deviation in the allele balance distribution from an expected ratio of 1:1 for a plurality of bi-allelic SNPs for at least one chromosome in a plurality of samples, determining whether the deviation occurs over the entire chromosome or only a portion of the identified chromosome, using the read coverage and allele balance data in complement to further refine and validate identified deviations for at least one chromosome in a plurality of samples, and identifying the at least one chromosome as an abnormal karyotype.

Additional advantages will be set forth in part in the description which follows or may be learned by practice. The advantages will be realized and attained by means of the elements and combinations particularly pointed out in the appended claims.

BRIEF DESCRIPTION OF THE DRAWINGS

The accompanying drawings, which are incorporated in and constitute a part of this specification, illustrate embodiments and together with the description, serve to explain the principles of the methods and systems:

FIG. 13A is a plot of chromosome X versus chromosome Y coverage ratios for all samples and a threshold for determining male (1302) and female (1304) samples indicated by the solid line 1306. Additionally, male samples having chromosome Y duplications can be identified using a chromosome Y coverage ratio threshold (dashed line 1308);

DETAILED DESCRIPTION

Figure 1:
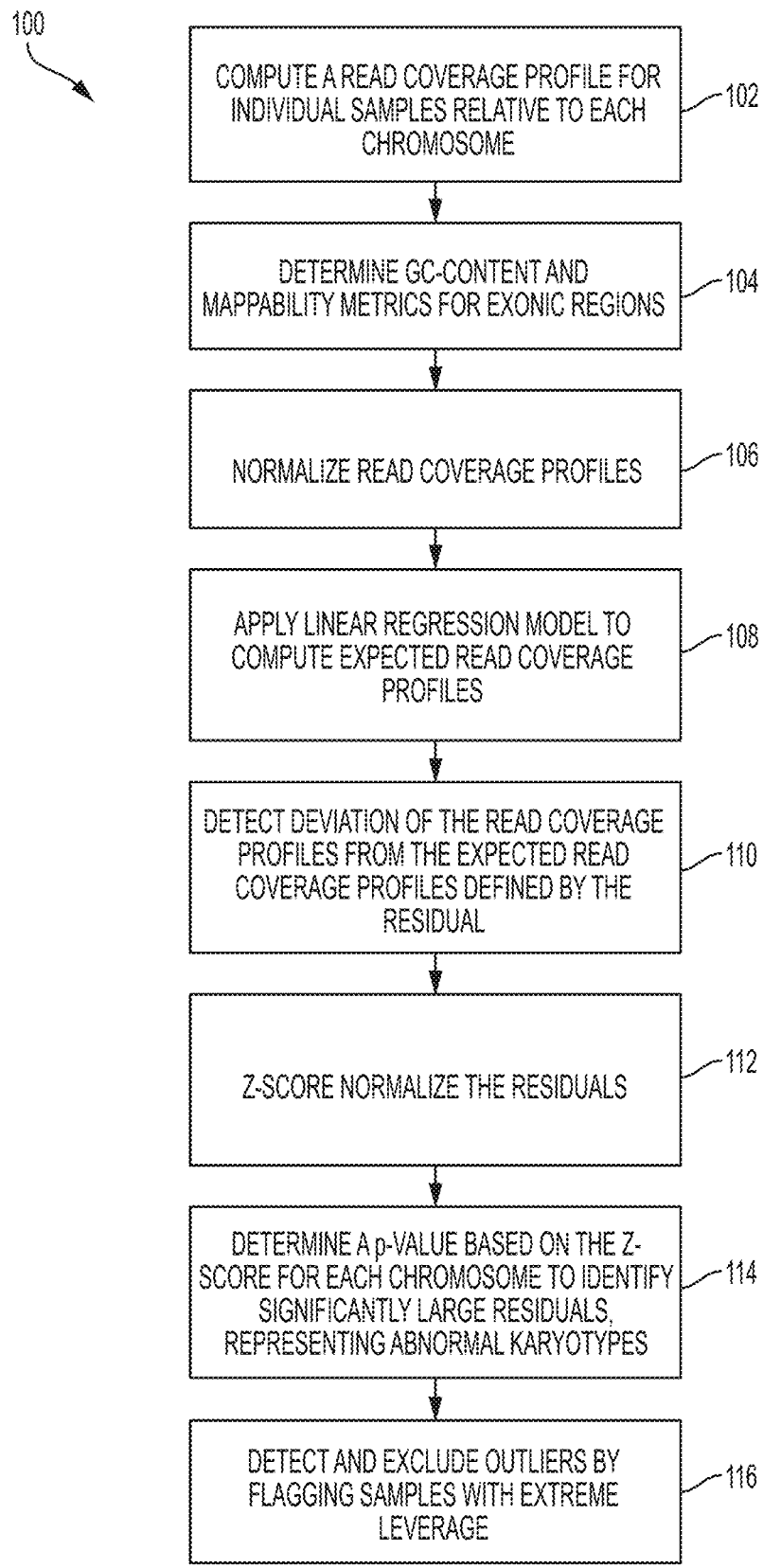
FIG. 1 is flowchart illustrating an example abnormal karyotype detection method.

Before the present methods and systems are disclosed and described, it is to be understood that the methods and systems are not limited to specific methods, specific components, or to particular implementations. It is also to be understood that the terminology used herein is for the purpose of describing particular embodiments only and is not intended to be limiting.

As used in the specification and the appended claims, the singular forms "a," "an" and "the" include plural referents unless the context clearly dictates otherwise. Ranges may be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint.

"Optional" or "optionally" means that the subsequently described event or circumstance may or may not occur, and that the description includes instances where said event or circumstance occurs and instances where it does not.

Throughout the description and claims of this specification, the word "comprise" and variations of the word, such as "comprising" and "comprises," means "including but not limited to," and is not intended to exclude, for example, other components, integers or steps. "Exemplary" means "an example of" and is not intended to convey an indication of a preferred or ideal embodiment. "Such as" is not used in a restrictive sense, but for explanatory purposes.

It is understood that the disclosed method and compositions are not limited to the particular methodology, protocols, and reagents described as these may vary. It is also to be understood that the terminology used herein is for the purpose of describing particular embodiments only, and is not intended to limit the scope of the present methods and system which will be limited only by the appended claims.

Unless defined otherwise, all technical and scientific terms used herein have the same meanings as commonly understood by one of skill in the art to which the disclosed method and compositions belong. Although any methods and materials similar or equivalent to those described herein can be used in the practice or testing of the present method and compositions, the particularly useful methods, devices, and materials are as described. Publications cited herein and the material for which they are cited are hereby specifically incorporated by reference. Nothing herein is to be construed as an admission that the present invention is not entitled to antedate such disclosure by virtue of prior invention. No admission is made that any reference constitutes prior art. The discussion of references states what their authors assert, and applicant reserves the right to challenge the accuracy and pertinency of the cited documents. It will be clearly understood that, although a number of publications are referred to herein, such reference does not constitute an admission that any of these documents forms part of the common general knowledge in the art.

Disclosed are components that can be used to perform the disclosed methods and systems. These and other components are disclosed herein, and it is understood that when combinations, subsets, interactions, groups, etc. of these components are disclosed that while specific reference of each various individual and collective combinations and permutation of these may not be explicitly disclosed, each is specifically contemplated and described herein, for all methods and systems. This applies to all aspects of this application including, but not limited to, steps in disclosed methods. Thus, if there are a variety of additional steps that can be performed it is understood that each of these additional steps can be performed with any specific embodiment or combination of embodiments of the disclosed methods.

The present methods and systems may be understood more readily by reference to the following detailed description of preferred embodiments and the examples included therein and to the Figures and their previous and following description.

As will be appreciated by one skilled in the art, the methods and systems may take the form of an entirely hardware embodiment, an entirely software embodiment, or an embodiment combining software and hardware aspects. Furthermore, the methods and systems may take the form of a computer program product on a computer-readable storage medium having computer-readable program instructions (e.g., computer software) embodied in the storage medium. More particularly, the present methods and systems may take the form of web-implemented computer software. Any suitable computer-readable storage medium may be utilized including hard disks, CD-ROMs, optical storage devices, or magnetic storage devices.

Embodiments of the methods and systems are described below with reference to block diagrams and flowchart illustrations of methods, systems, apparatuses and computer program products. It will be understood that each block of the block diagrams and flowchart illustrations, and combinations of blocks in the block diagrams and flowchart illustrations, respectively, can be implemented by computer program instructions. These computer program instructions may be loaded onto a general purpose computer, special purpose computer, or other programmable data processing apparatus to produce a machine, such that the instructions which execute on the computer or other programmable data processing apparatus create a means for implementing the functions specified in the flowchart block or blocks.

These computer program instructions may also be stored in a computer-readable memory that can direct a computer or other programmable data processing apparatus to function in a particular manner, such that the instructions stored in the computer-readable memory produce an article of manufacture including computer-readable instructions for implementing the function specified in the flowchart block or blocks. The computer program instructions may also be loaded onto a computer or other programmable data processing apparatus to cause a series of operational steps to be performed on the computer or other programmable apparatus to produce a computer-implemented process such that the instructions that execute on the computer or other programmable apparatus provide steps for implementing the functions specified in the flowchart block or blocks.

Accordingly, blocks of the block diagrams and flowchart illustrations support combinations of means for performing the specified functions, combinations of steps for performing the specified functions and program instruction means for performing the specified functions. It will also be understood that each block of the block diagrams and flowchart illustrations, and combinations of blocks in the block diagrams and flowchart illustrations, can be implemented by special purpose hardware-based computer systems that perform the specified functions or steps, or combinations of special purpose hardware and computer instructions.

In an aspect, disclosed are methods for detecting samples with abnormal karyotypes from population-scale whole-exome sequencing data, also referred to as KaryoScan. Abnormal karyotypes can be detected through read depth distributions over chromosomes, but multiple factors confound the ability to distinguish true chromosomal anomalies from noise. PCR amplification is biased by GC content and experimental conditions, often resulting in non-uniform amplification of DNA fragments across the genome. Additionally, exome capture techniques do not yield uniform target coverage. Thus, the expected coverage of any particular chromosome or chromosomal region is dependent on multiple factors, some of which are measurable and some of which are not.

The disclosed methods, example method 100 illustrated in FIG. 1, can compute a read coverage profile for individual samples relative to each chromosome at 102. To reduce bias in read coverage representative GC-content and mappability metrics can be determined for exonic regions at 104, as variation is smallest in regions with GC content close to 50% and high mappability. A robust read coverage profile $r_i$ can be determined for each chromosome i as the sum of read depths over exomic regions with GC content within a range (e.g., 45-55%) and having mappability over a threshold. This metric, as opposed to median chromosomal tag density, allows for sub-chromosomal resolution.

Chromosomal read coverage profiles can then be normalized at 106 to represent an exome-wide ratio of read coverage for each chromosome relative to other autosomes. The exome-wide coverage ratio $\gamma_i$ of chromosome i can be expressed as:

$$\gamma_i = \frac{r_i}{\sum_{\forall j \in (A-i)} r_j} \quad (1)$$

where (A-i) is the set of autosomes excluding chromosome i, and $\gamma_i$ is determined for all autosomes and chromosome X (chromosome Y can be considered independently). The coverage ratio of chromosome i is therefore the ratio of reads on chromosome i compared to all other autosomes.

Figure 2:
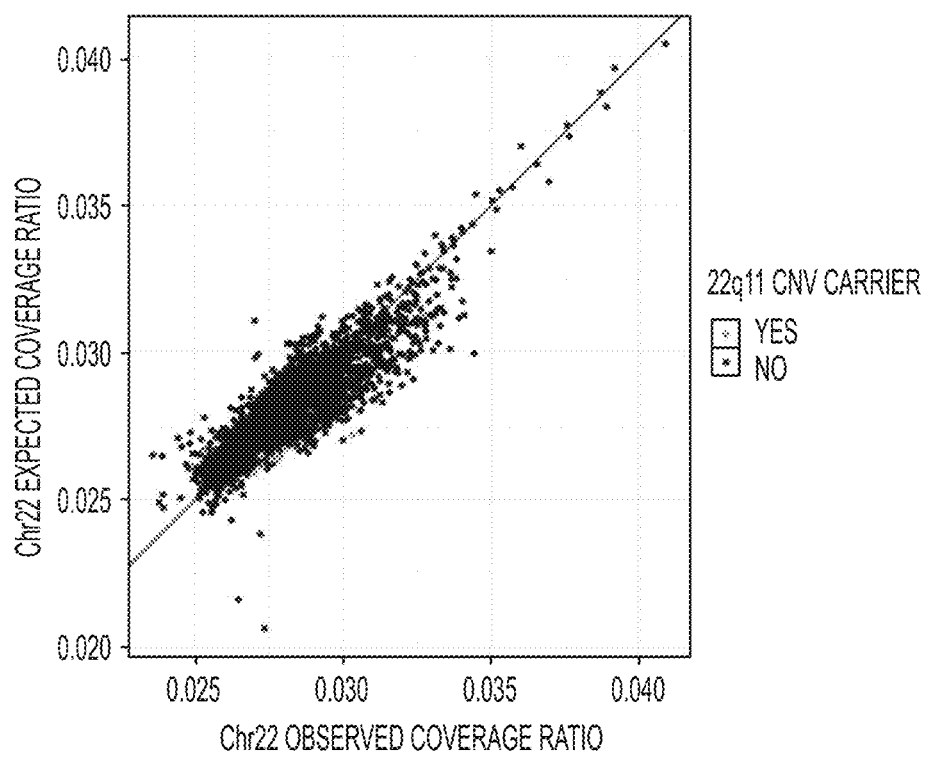
FIG. 2 is a graph illustrating an example linear regression model.

Chromosomal abnormalities manifest in deviations of $\gamma_i$ from expectation. However, the expected value of $\gamma_i$ is not constant even between samples of normal (diploid) karyotype and is dependent upon experimental conditions. A linear regression model can be used to predict the expected value $\hat{\gamma}_i$ of $\gamma_i$ for every individual on every chromosome at 108. An example of the observed ($\gamma_i$) and expected ($\hat{\gamma}_i$) values for chromosome 22 after fitting a linear regression are shown in FIG. 2. Sequencing quality control (QC) metrics from Picard that are correlated with variations in read depth can be used as covariates in this model. The QC metrics can comprise, for example, one or more of, GCDROPOUT, ATDROPOUT, MEANINSERTSIZE, ONBAITVSSELECTED, PCTPFUQREADS, PCTTARGETBASES10×, PCTTARGETBASES50×, and/or the like.

While these QC metrics can describe a substantial portion of the variation observed in read coverage, additional biases that are not measurable can be reflected in results obtained using previously known methods. These biases are correlated between chromosomes with similar exomic GC content distributions, and including $\gamma_i$ values of similar chromosomes as additional co-variates can reduce variance to acceptable levels. In one aspect, while this is beneficial for model specificity, one drawback is that these other chromosomes themselves might be karyotypically abnormal, which could result in false positive calls on the target chromosome. An advantage provided by the method of the invention herein is that false positive calls on the target chromosome are minimized by restricting the number of covariates from other chromosomes. For example, the number of covariates from other chromosomes can be restricted to two.

Thus, a linear model can be regressed for each chromosome over the full n sample set, with:

$$\hat{\gamma}_i = f(\text{QC metrics}, \gamma_j, \gamma_k) \quad (2)$$

where chromosomes j,k are defined as the two autosomes with minimal D statistics relative to the GC content distribution of chromosome i. In some aspects, gender (as defined by a chromosome Y coverage threshold) can be used as an additional covariate for chromosome X.

Detection of abnormal karyotypes can be based on detection of deviations of $\gamma_i$ from expectation for a particular sample ($\hat{\gamma}_i$) at 110, defined by the residual. However, estimates for samples that fall on the extremes of QC metric space inherently can produce mean estimates with higher variance, such that the interpretation of raw residuals cannot be assumed uniform over all samples. At 112, the disclosed methods can Z-score normalize the residuals relative to the standard error of the mean estimate, $S(\hat{\gamma}_i)$, for an individual sample with covariates x (See FIG. 6):

$$S(\hat{\gamma}_i) = S_e \sqrt{\frac{1}{n} + \frac{(x - \bar{x})^2}{\sum_{j=1 \ldots n} (x_j - \bar{x})^2}} \quad (3)$$

where $S_e$ is the residual standard error, n is the number of samples used to fit the model, and:

$$Z_i = \frac{(\gamma_i - \hat{\gamma}_i)}{S(\hat{\gamma}_i)\sqrt{n}} \quad (4)$$

Figure 3:
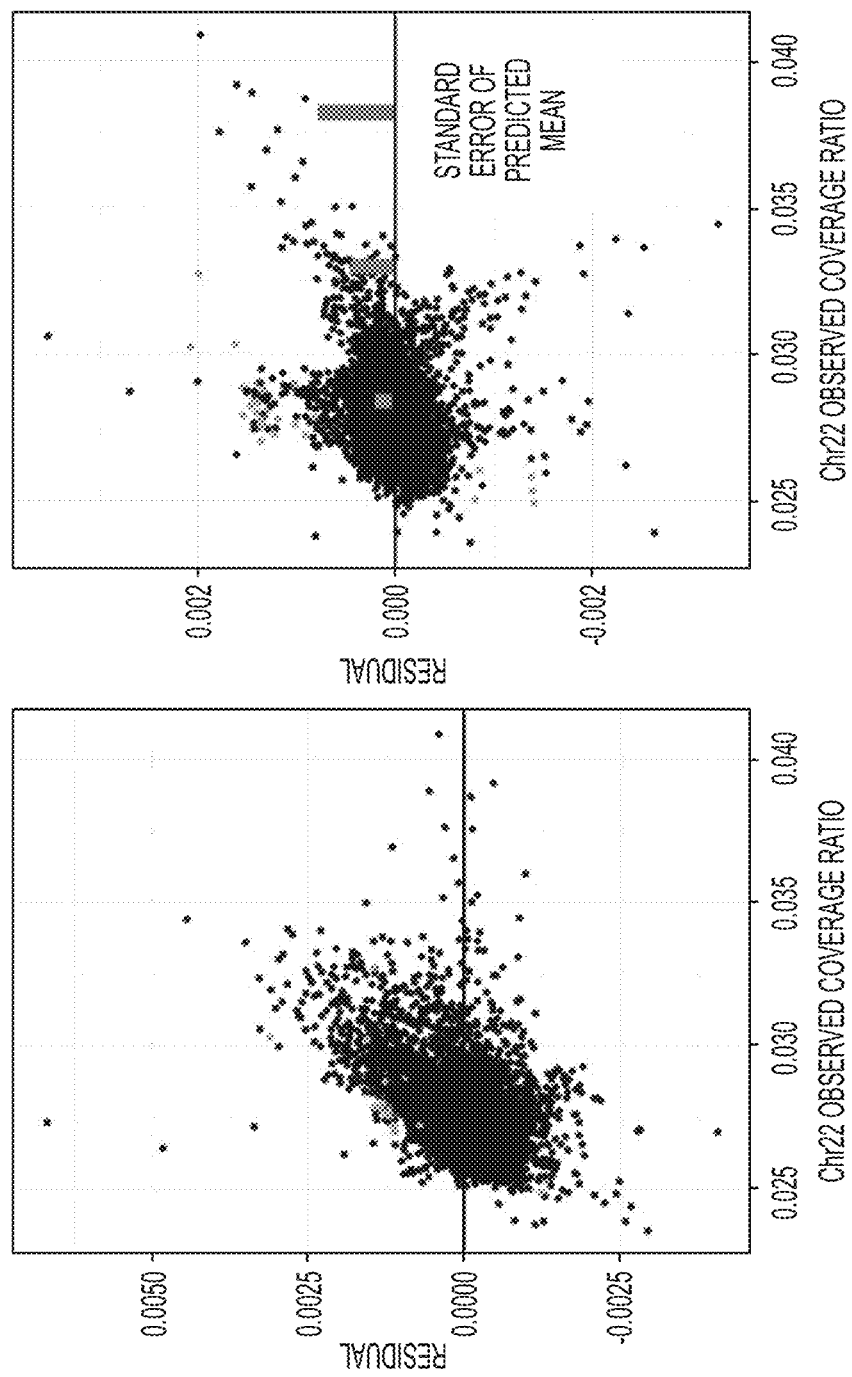
FIG. 3 is a graph illustrating abnormal karyotypes exhibiting large residuals.

A p-value based on the Z-score can be determined for each chromosome to identify significantly large residuals at 114, representing abnormal karyotypes for chromosome i. In an aspect, p-value cutoff for p<0.05 and q<0.05 (FDR-adjusted p) can be used to identify significantly large residuals. See FIG. 3, in which the observed ($\gamma_i$) and expected ($\hat{\gamma}_i$)

values after fitting a linear regression are shown. In another aspect, a p-value of up to 0.1 can be used.

Large residuals can be a result of both true abnormal karyotypes for the chromosome of interest as well as abnormal covariate values (due to either outliers in QC metric space or an abnormal karyotype on one of the covariate chromosomes). At 116 outliers can be detected due to unusual covariates by flagging samples with extreme leverage (often denoted $h_i$, where $1/n < h_i < 1$) on the linear model for each chromosome. Leverage quantifies how much a sample's x-values (covariates) influence the model. Leverage can be used to flag outliers not representing true abnormal karyotypes on chromosomes of interest. Leverage and standard error are correlated, so high-leverage values should have high (insignificant) p-values. Leverage can be reported as a function of n and p:

$$h_i(n, p) = \left[\frac{1}{n} + \frac{(x - \bar{x})^2}{\sum_{j=1 \ldots n} (x_j - \bar{x})^2}\right] \cdot \frac{n}{p+1} \quad (5)$$

where p is the number of covariates in the model. In an aspect, samples can be flagged that having $h_i$ (n,p) values greater than a threshold. For example, the threshold can be from about 3 to about 5. This can be generally applied to ensure an optimal fit. A more conservative threshold can be used to flag the most extreme values, for example, values corresponding to the 99.5th and 99.9th percentiles (~10 and ~26). In some cases, it is useful to remove high leverage samples and refit the model, thereby reducing standard error for samples not having high leverage and improving (reducing) p-value estimates.

Figure 4:
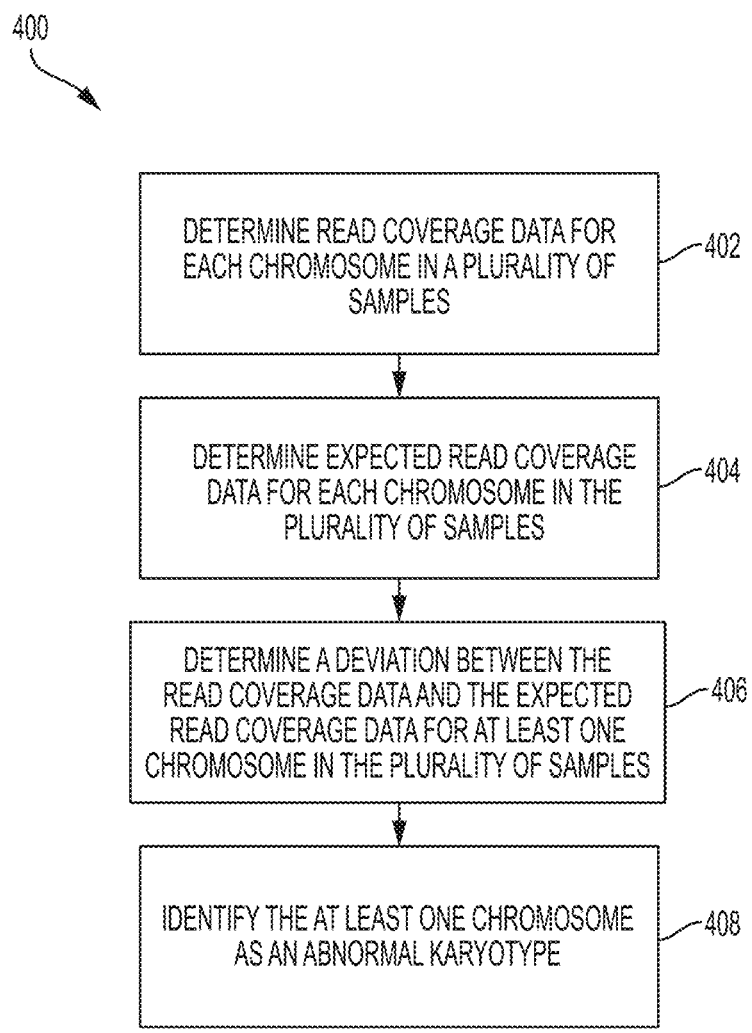
FIG. 4 is another flowchart illustrating an example abnormal karyotype detection method.

FIG. 4 is a flowchart illustrating an example method 400 for detecting abnormal karyotypes. At step 402, read coverage data for each chromosome in a plurality of samples can be determined. In an aspect, each chromosome can comprise a plurality of genomic regions. Determining read coverage data for each chromosome in a plurality of samples can comprise determining a sum of read depths over exomic regions with GC content within a range and a mappability score above a threshold.

The method 400 can further comprise filtering the read coverage data. Filtering the read coverage data can comprise filtering the read coverage data based on a level of guanine-cytosine (GC) content in one or more genomic regions of the plurality of genomic regions. Filtering the read coverage data based on a level of guanine-cytosine (GC) content in one or more genomic regions of the plurality of genomic regions can comprise determining a level of GC content for each of the plurality of genomic regions and excluding one or more genomic regions of the plurality of genomic regions having a level of GC content outside a range.

Figure 5:
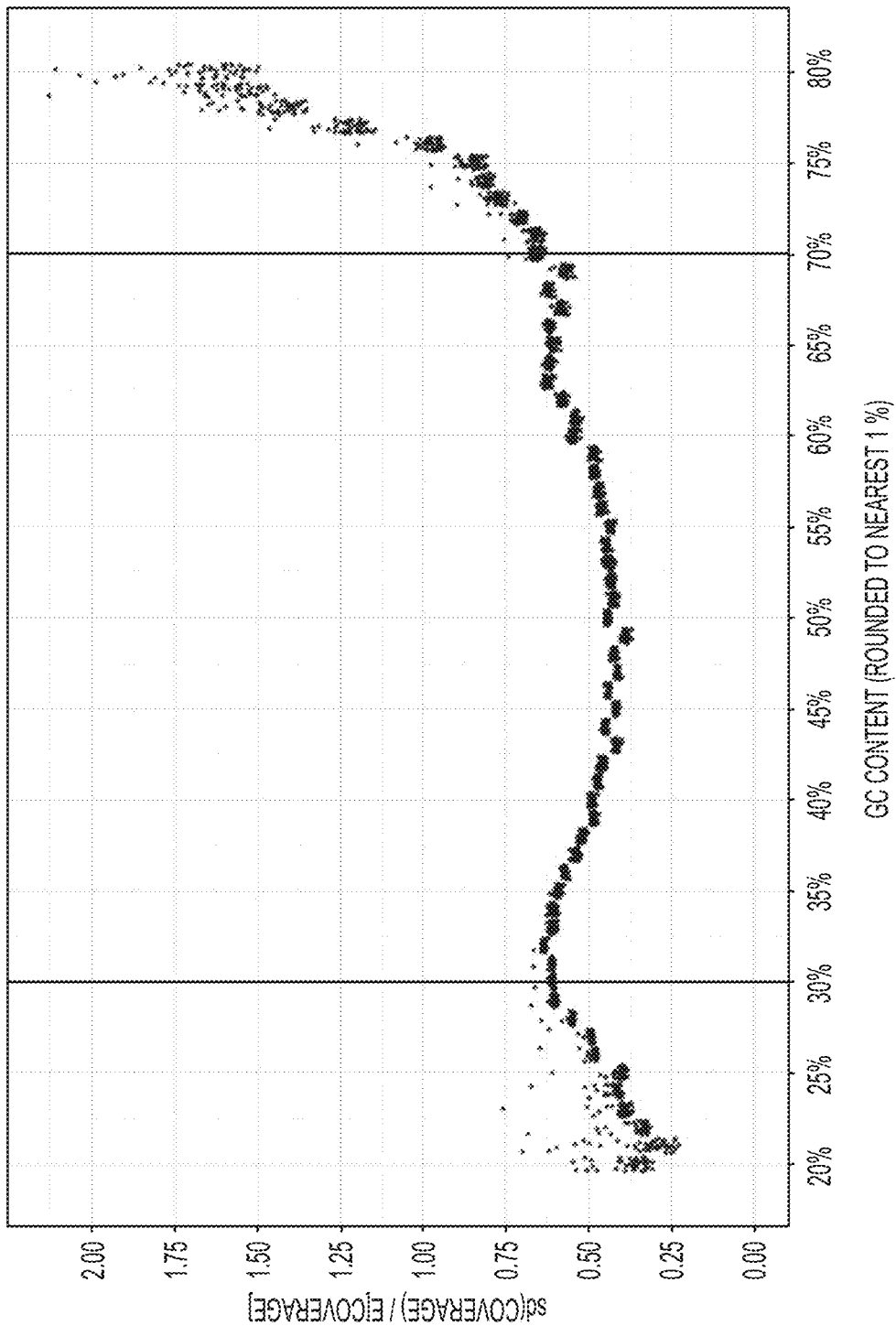
FIG. 5 shows a graph illustrating the relationship of GC content and coverage.

In an aspect, the present methods can filter one or more genomic regions with extreme GC content. GC-amplification bias can be corrected when the bias is mostly consistent for any particular level of GC content. At very low or high GC content, however, the stochastic coverage volatility may increase dramatically, making it difficult to normalize effectively. Accordingly, the present methods can filter one or more genomic regions where the GC-fraction is outside of a configurable (e.g., or predefined) range or threshold. As an illustration, the configurable range can comprise [0.3, 0.7], as shown in FIG. 5. It should be appreciated, however, that other ranges (e.g., thresholds) can be utilized as appropriate. FIG. 5 shows a graph illustrating the relationship of GC content and coverage. For example, the coefficient of variation (e.g., standard deviation divided by mean) of coverage is shown on the y-axis and GC content is shown in the x-axis. The graph shows 50 samples (e.g., points jittered for visibility). Above a default upper-limit (e.g., GC=0.7) of the configurable range, coverage variance can be very high relative to the mean. Below a default lower-limit (e.g., GC content=0.3) of the configurable range, additional problems arise. For example, the variance of coverage itself can be highly variable between samples. This variance makes it difficult to accurately estimate the expected variance of coverage for a particular sample at a particular window, as each reference panel sample's coverage value is an observation from a different distribution.

Filtering the read coverage data in the method 400 can comprise filtering one or more genomic regions of the plurality of genomic regions based on a mappability score of the one or more genomic regions of the plurality of genomic regions. Filtering one or more genomic regions of the plurality of genomic regions based on a mappability score of the one or more genomic regions of the plurality of genomic regions can comprise determining a mappability score for each genomic region of the plurality of genomic regions and excluding one or more genomic regions of the plurality of genomic if the mappability score of the one or more genomic regions of the plurality of genomic regions is below a predetermined threshold.

For example, the present methods and systems can filter the one or more genomic regions of the plurality of genomic regions where the mean mappability score for k-mers starting at each base in a window (default k=75) is less than 0.75. Determining a mappability score for each genomic region of the plurality of genomic regions can comprise determining an average of an inverse reference-genome frequency of k-mers whose first base overlaps the genomic region of the plurality of genomic regions.

In an aspect, the method 400 can further comprise normalizing the read coverage data. Normalizing the read coverage data can comprise determining an exome-wide ratio of read coverage for each chromosome relative to other autosomes. The exome-wide ratio (γ) can be determined for each chromosome (i) by:

$$\gamma_i = \frac{r_i}{\sum_{\forall j \in (A-i)} r_j}$$

wherein A is the set of autosomes and r is read coverage.

At step 404, expected read coverage data for each chromosome in the plurality of samples can be determined. Determining expected read coverage data for each chromosome in the plurality of samples can comprise applying a linear regression model to determine an expected exome-wide ratio for each chromosome, wherein a plurality of metrics are used as covariates. The plurality of metrics can comprise sequencing quality control metrics (QC metrics). Systematic coverage biases that arise due to variability in sequencing conditions are commonly referred to as "batch effects." In an aspect, the present methods and systems can be configured to correct for batch effects. For example, instead of comparing read coverage data based on the read coverage profiles—a high-dimensional space—the present methods and systems can be configured to consider a low-dimensional metric space based on sequencing quality control (QC) metrics. For example, the sequencing QC metrics can comprise seven sequencing QC metrics. The sequencing QC metrics can comprise sequencing QC metrics from a sequencing tool, such as Picard. Working in this low-dimensional space allows for improved scalability. For example, samples can be indexed ahead-of-time (e.g., using any appropriate indexing and/or search algorithm).

In an aspect, the expected exome-wide ratio ($\hat{\gamma}$) can be determined for each chromosome (i) by:

$$\hat{\gamma}_i = f(QC \text{ metrics}, \gamma_j, \gamma_k)$$

wherein chromosomes j,k are defined as two autosomes with minimal D statistics relative to a GC content distribution of chromosome i and $\varepsilon_i$ is a random component of a linear relationship between $\hat{\gamma}$ and $\gamma_j, \gamma_k$.

At step 406, a deviation between the read coverage data and the expected read coverage data for at least one chromosome in the plurality of samples can be determined. Determining a deviation between the read coverage data and the expected read coverage data for at least one chromosome in the plurality of samples can comprise determining, for each chromosome in the plurality of samples, a difference between the read coverage data and the expected read coverage data to generate a plurality of residuals and Z-score normalizing the plurality of residuals relative to a standard error of the mean estimate, $S(\hat{\gamma}_i)$, for an individual sample of the plurality of samples with covariates x:

$$S(\hat{\gamma}_i) = S_e \sqrt{\frac{1}{n} + \frac{(x - \bar{x})^2}{\sum_{j=1 \ldots n}(x_j - \bar{x})^2}}$$

where $S_e$ is the residual standard error, and:

$$Z_i = \frac{(\gamma_i - \hat{\gamma}_i)}{S(\hat{\gamma}_i)\sqrt{n}}.$$

Figure 6:
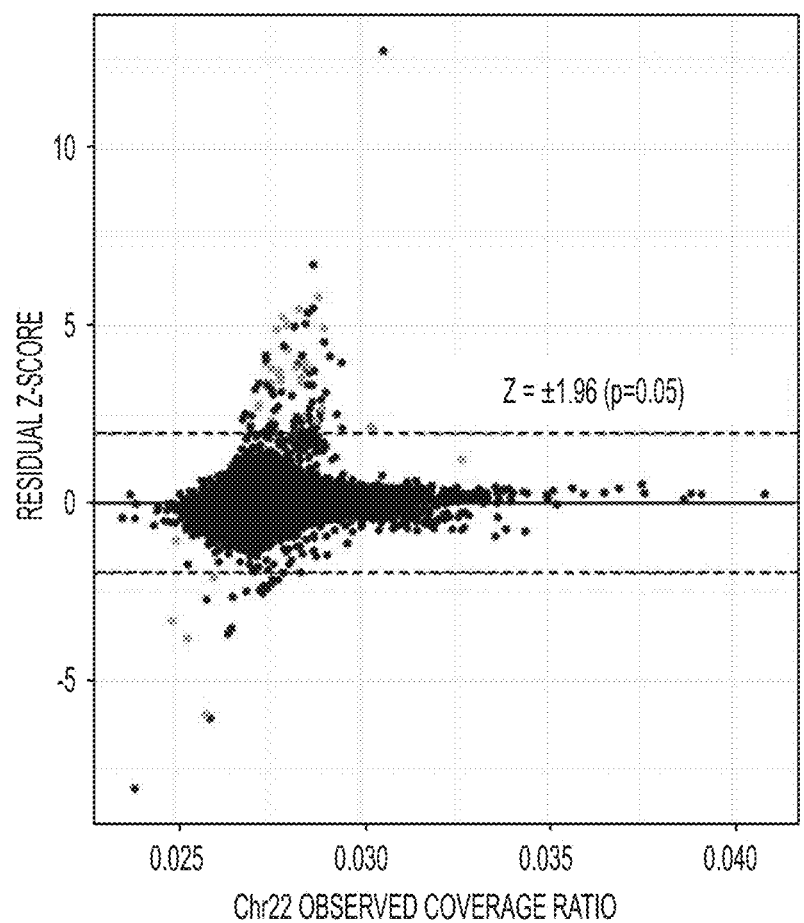
FIG. 6 is a graph illustrating identified abnormal karyotypes and outliers.
Figure 7A:
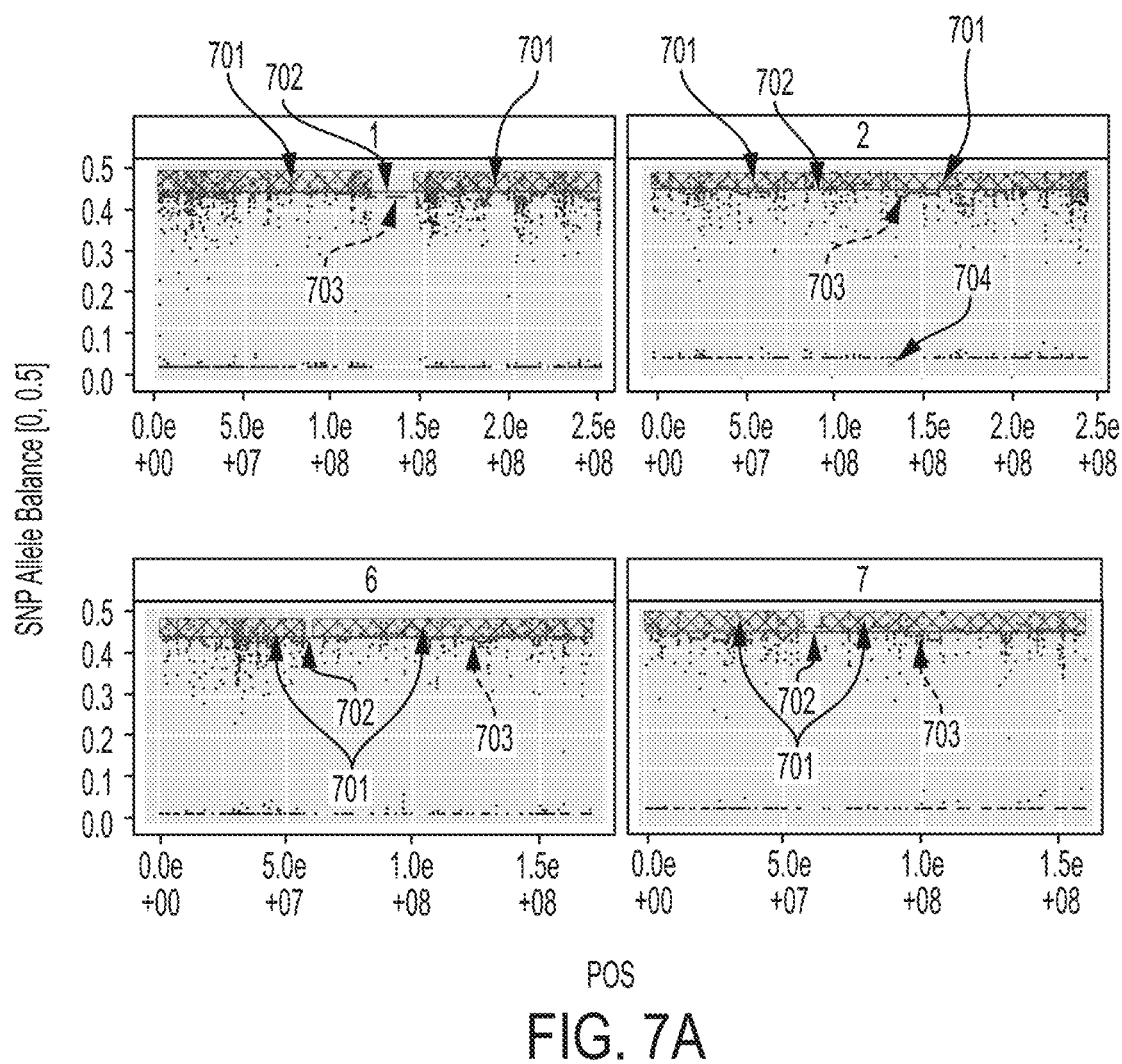
FIGS. 7A, 7B, 7C, 7D, 7E, and 7F are allele balance plots showing anomalies on chromosomes 9, 13 and 20 for a sample. The subplot number is the chromosome number. The shaded bar (701) denotes the normal range of variability expected for a heterozygous SNP allele balance of 0.5. The solid line (702) denotes the whole chromosome median allele balance. The dashed line (703) denotes the local median allele balance in an approximately 20 SNP rolling window. The line (704) denotes runs-of-homozygosity.
Figure 7B:
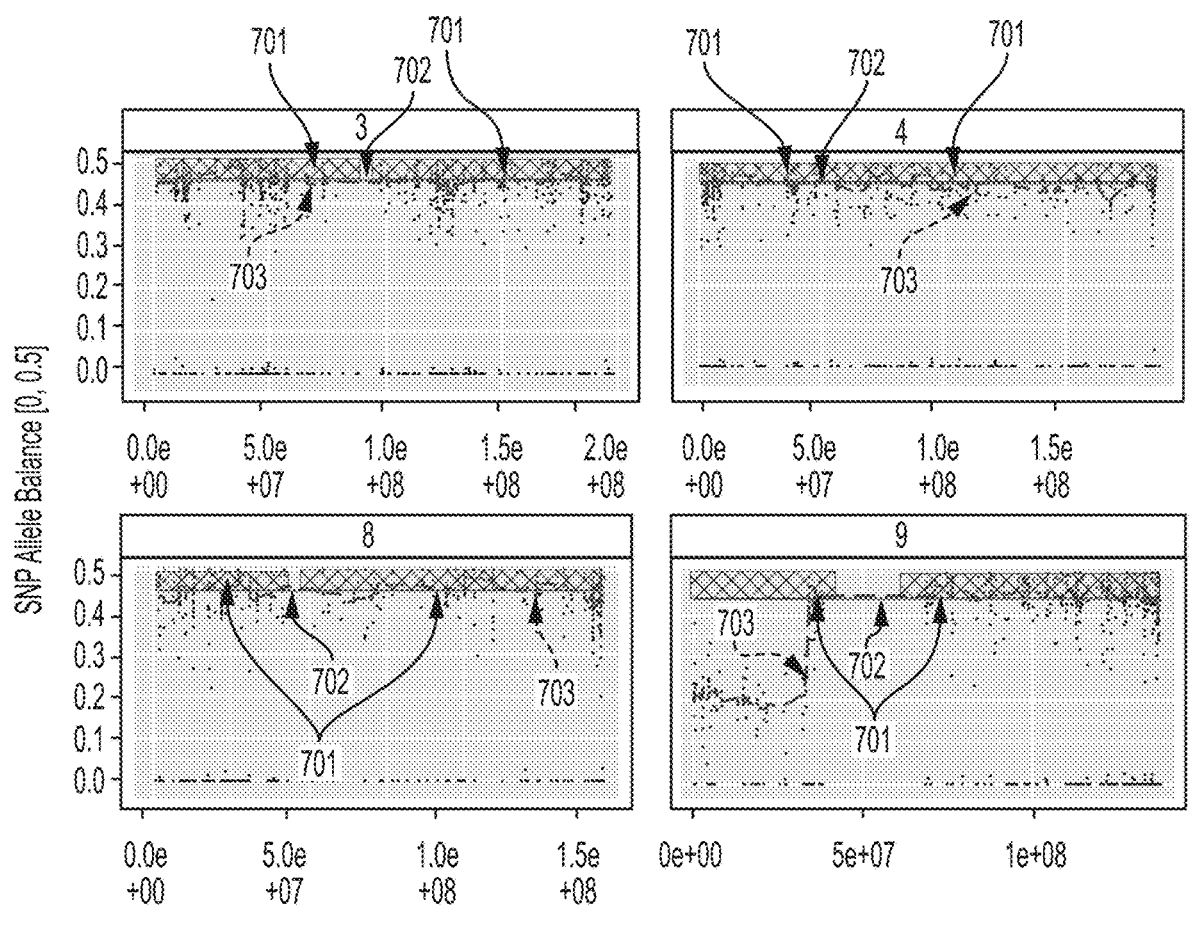
Figure 7C:
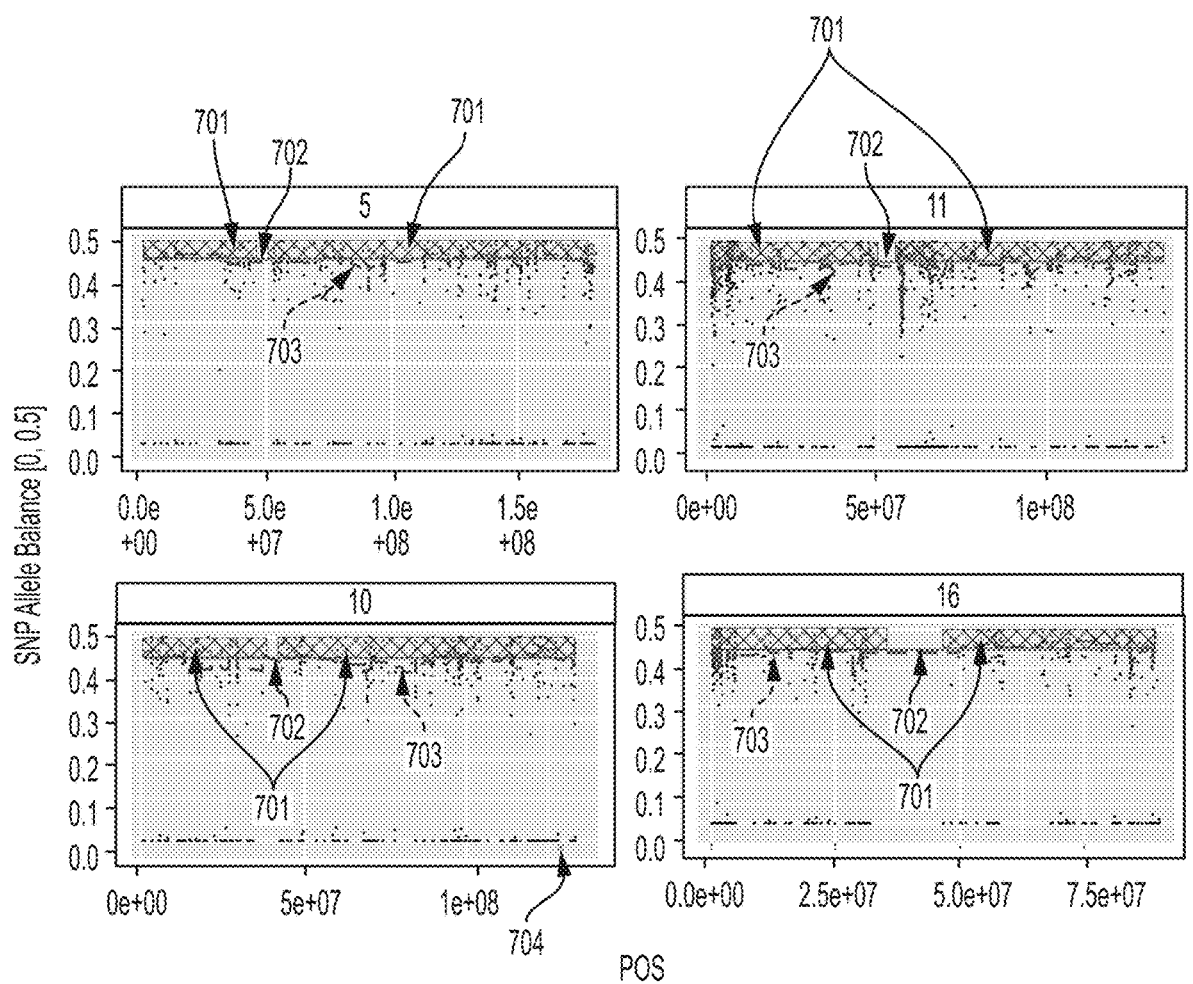
Figure 7D:
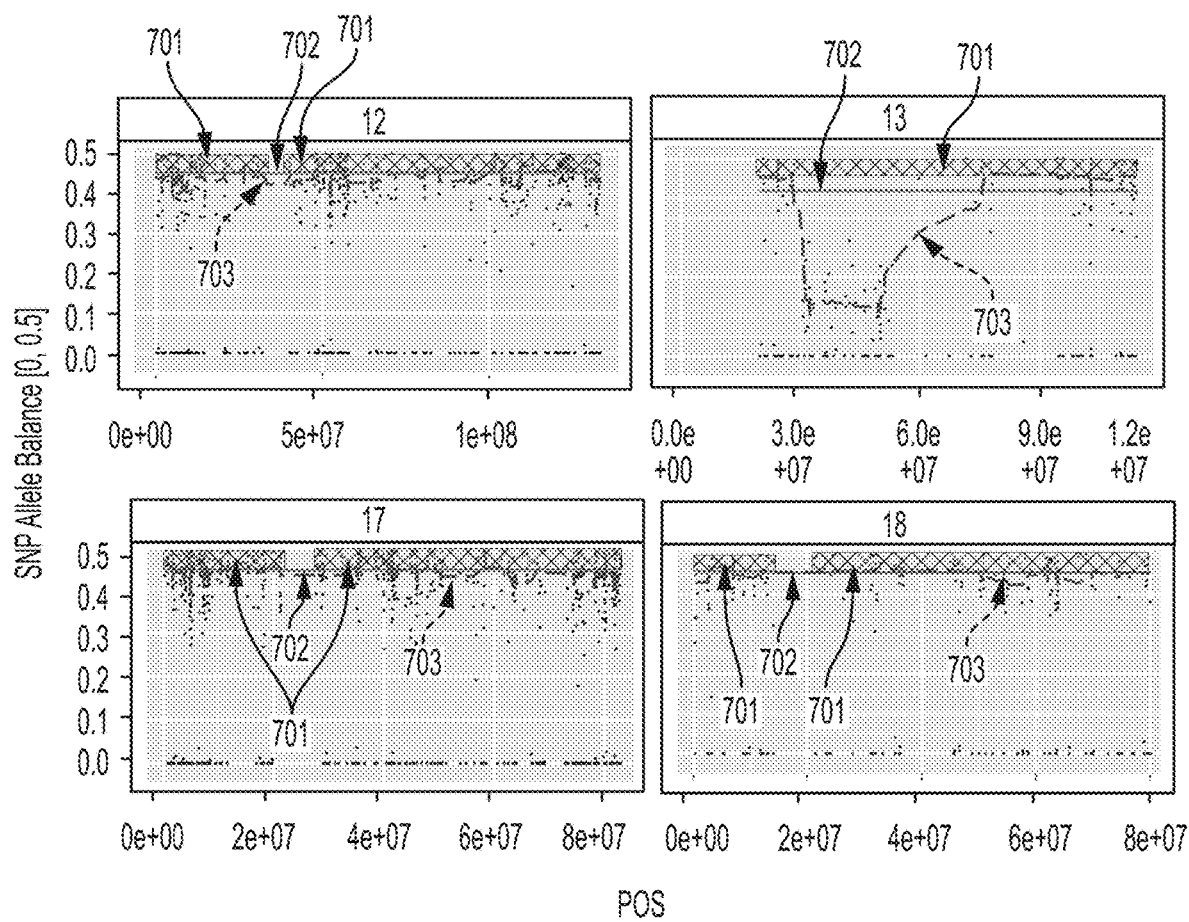
Figure 7E:
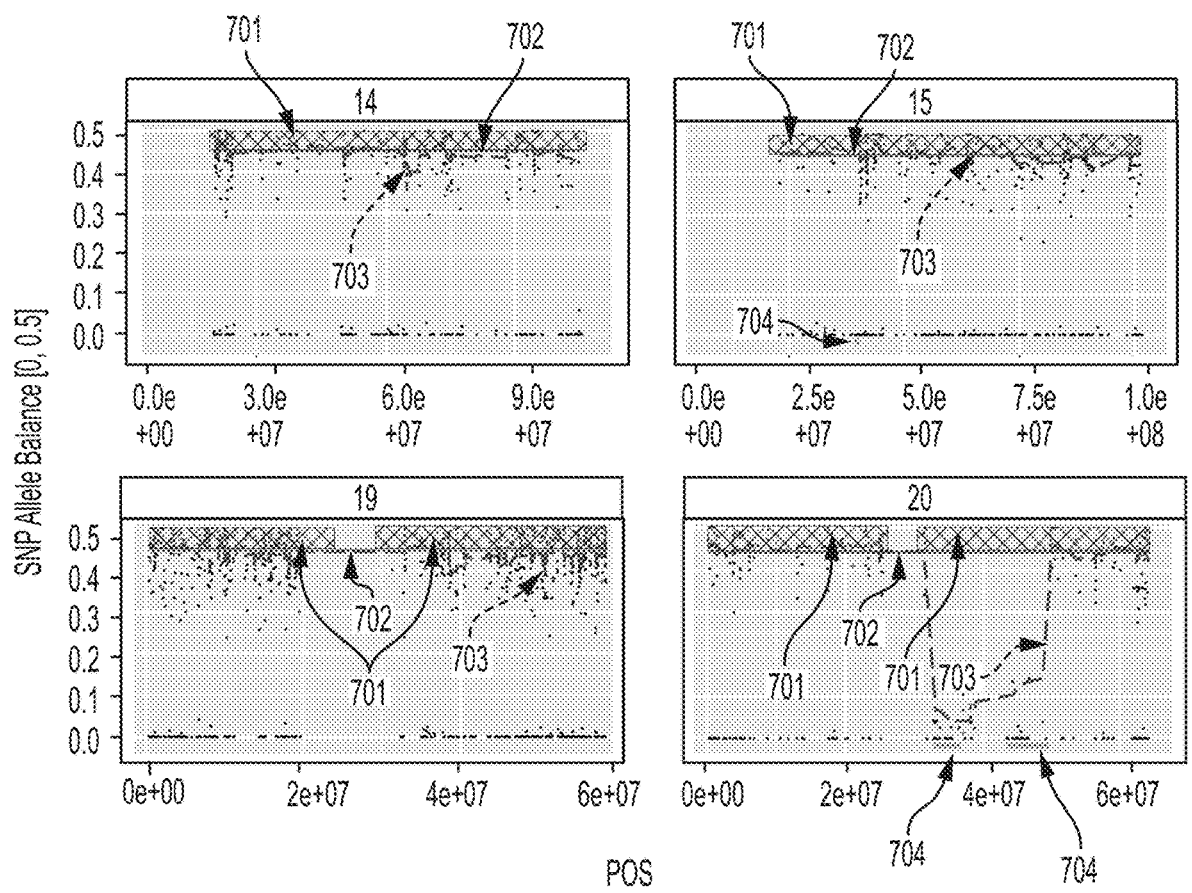
Figure 7F:
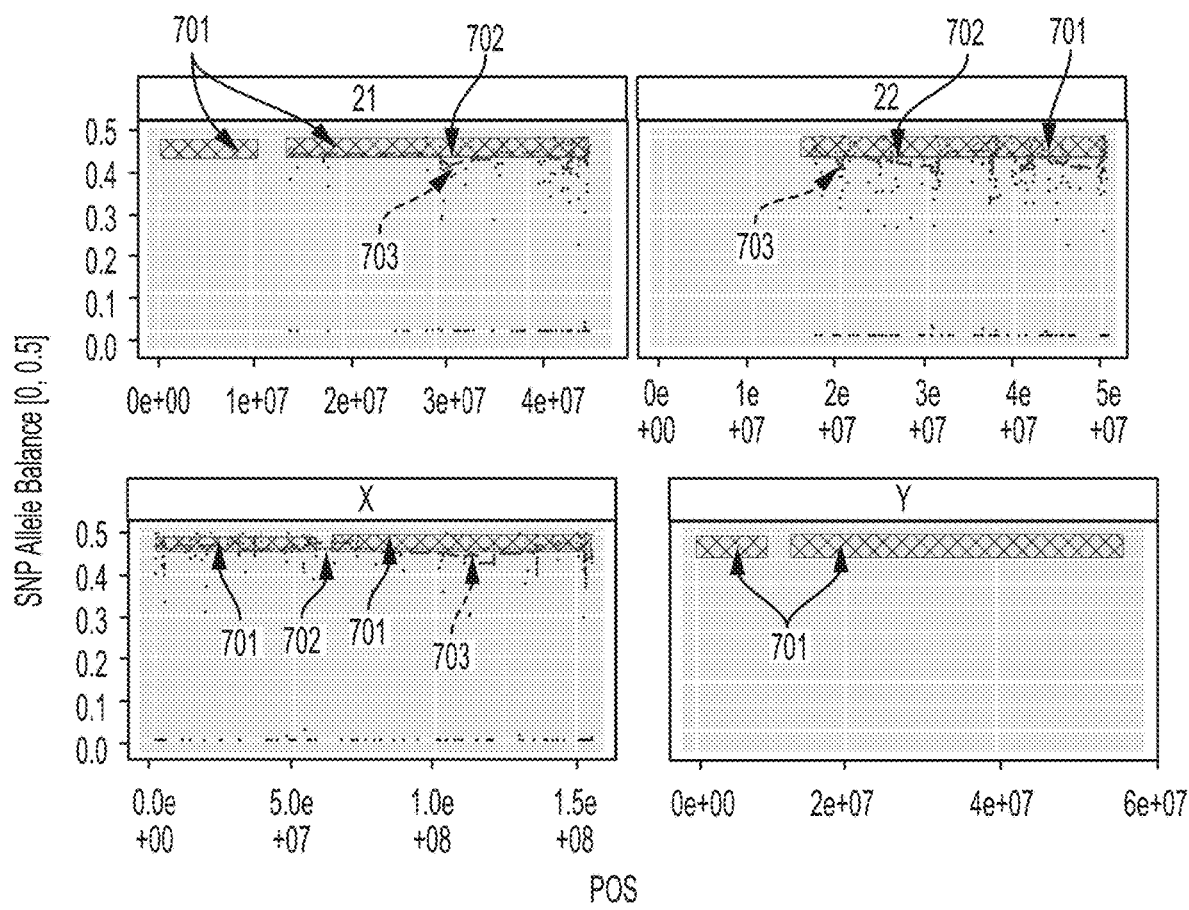

See FIG. 6, which depicts the results obtained using a linear regression model, in which the covariates included QC metrics and chromosomes, and in which the observed ($\gamma_i$) and expected ($\hat{\gamma}_i$) values after fitting the linear regression are shown 6. In another aspect, a different standard error estimator can be used, for example the raw residual standard error (one value for the entire model) or using heteroskedasticity-consistent standard errors.

The method 400 can further comprise determining a p-value based on the Z-score for each chromosome to identify significantly large residuals, representing abnormal karyotypes for chromosome i. Significantly large residuals can comprise residuals having a p-value less than 0.05. See FIG. 6.

At step 408, the at least one chromosome can be identified as an abnormal karyotype. The identified abnormal karyotype(s) can be output. For example, the identified abnormal karyotype(s) can be output to a user (e.g., via a user interface). The identified abnormal karyotype(s) can be transmitted via a network to remote location. The identified abnormal karyotype(s) can be provided as input to another executable program. The identified abnormal karyotype(s) can be stored in a storage location, such as a database, or other file format. Example output is shown in FIGS. 7-10.

Figure 8:
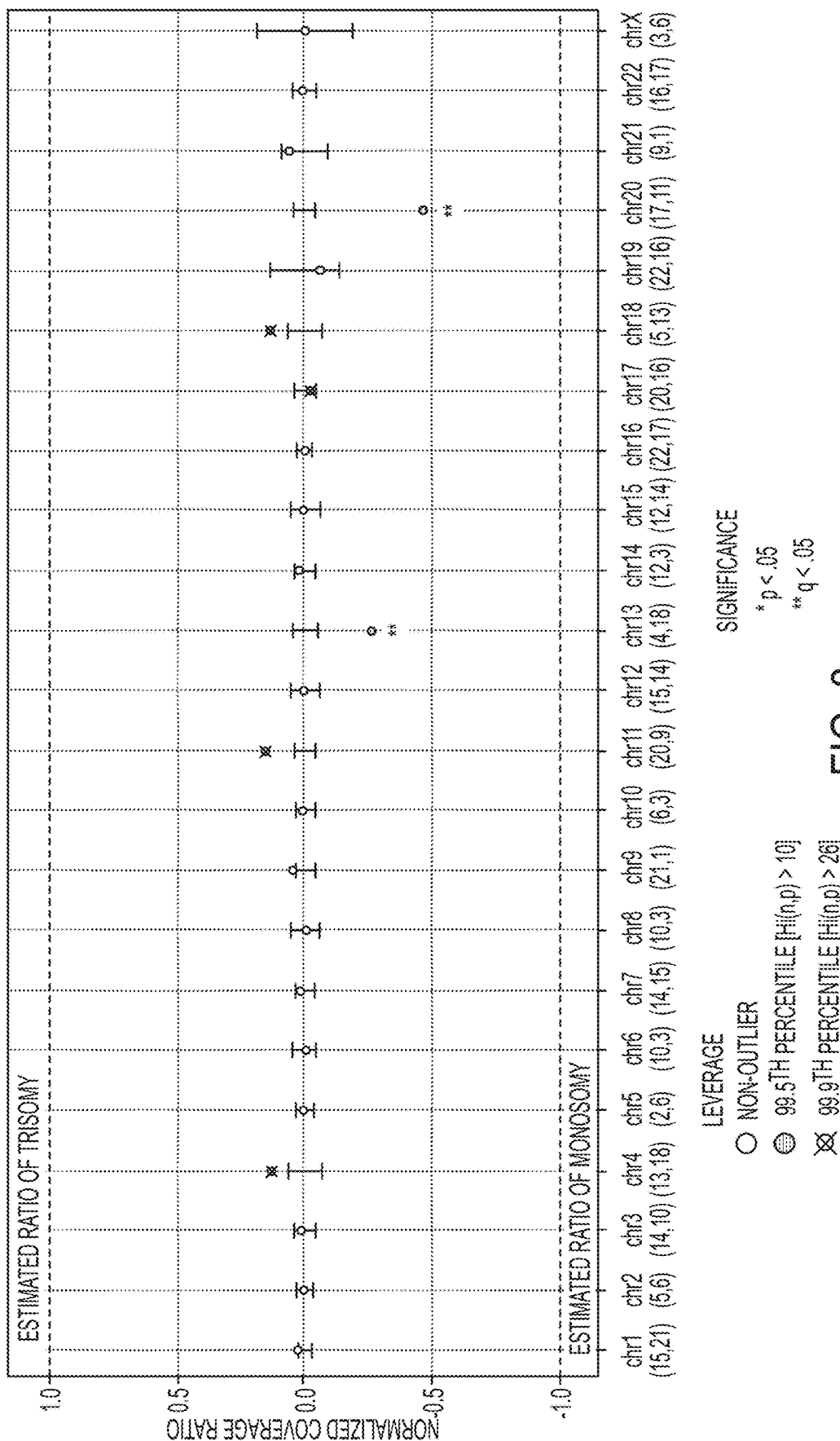
FIG. 8 is a read coverage plot for the same sample as in FIGS. 7A-F.
Figure 9A:
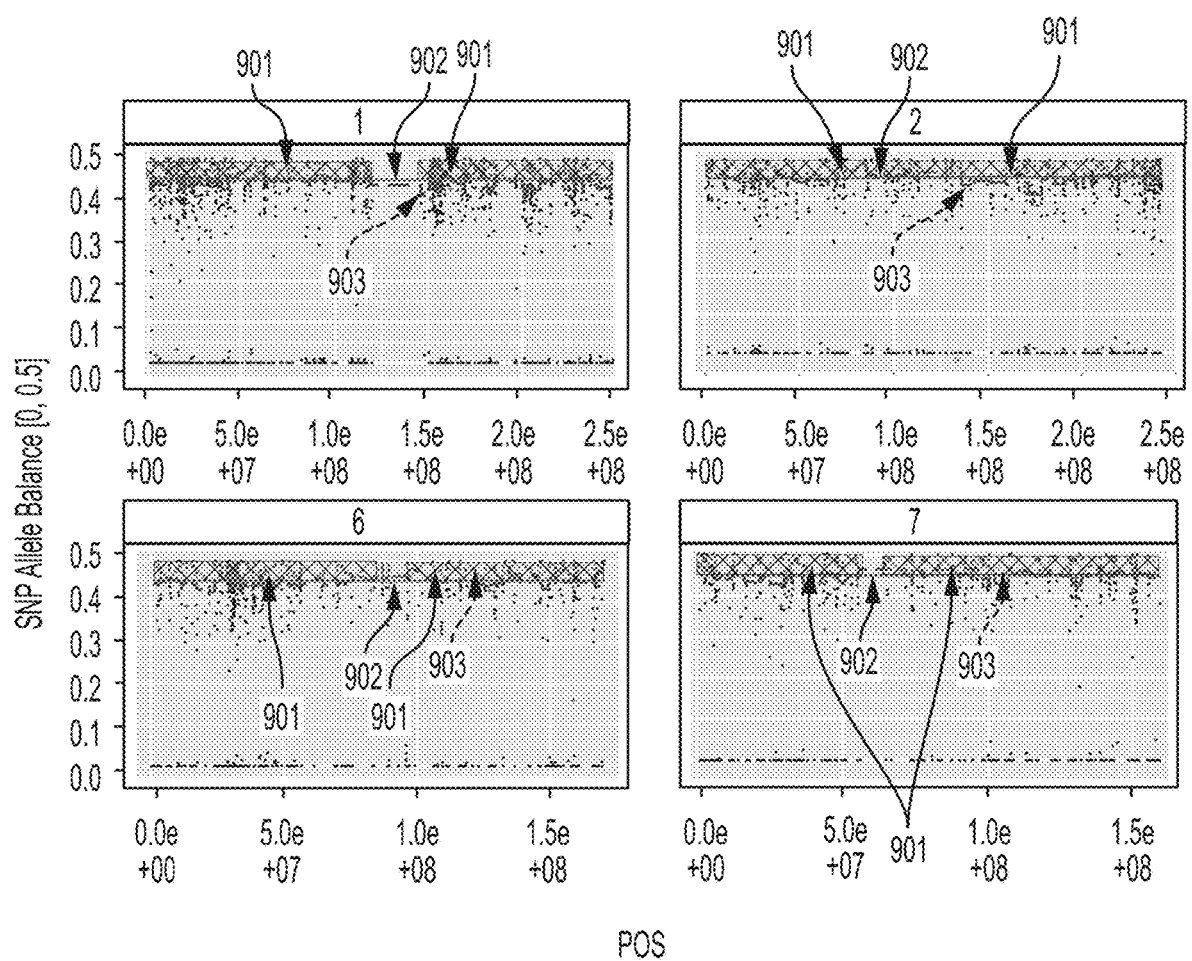
FIGS. 9A, 9B, 9C, 9D, 9E, and 9F are allele balance plots showing an anomaly on chromosome 21 in a sample and a run-of-homozygosity encompassing all of chromosome X, implying a karyotypically normal male sample having only one X chromosome. The shaded bar (901) denotes the normal range of variability expected for a heterozygous SNP allele balance of 0.5. The solid line (902) denotes the whole chromosome median allele balance. The dashed line (903) denotes the local median allele balance in an approximately 20 SNP rolling window. The line (904) denotes runs-of-homozygosity.
Figure 9B:
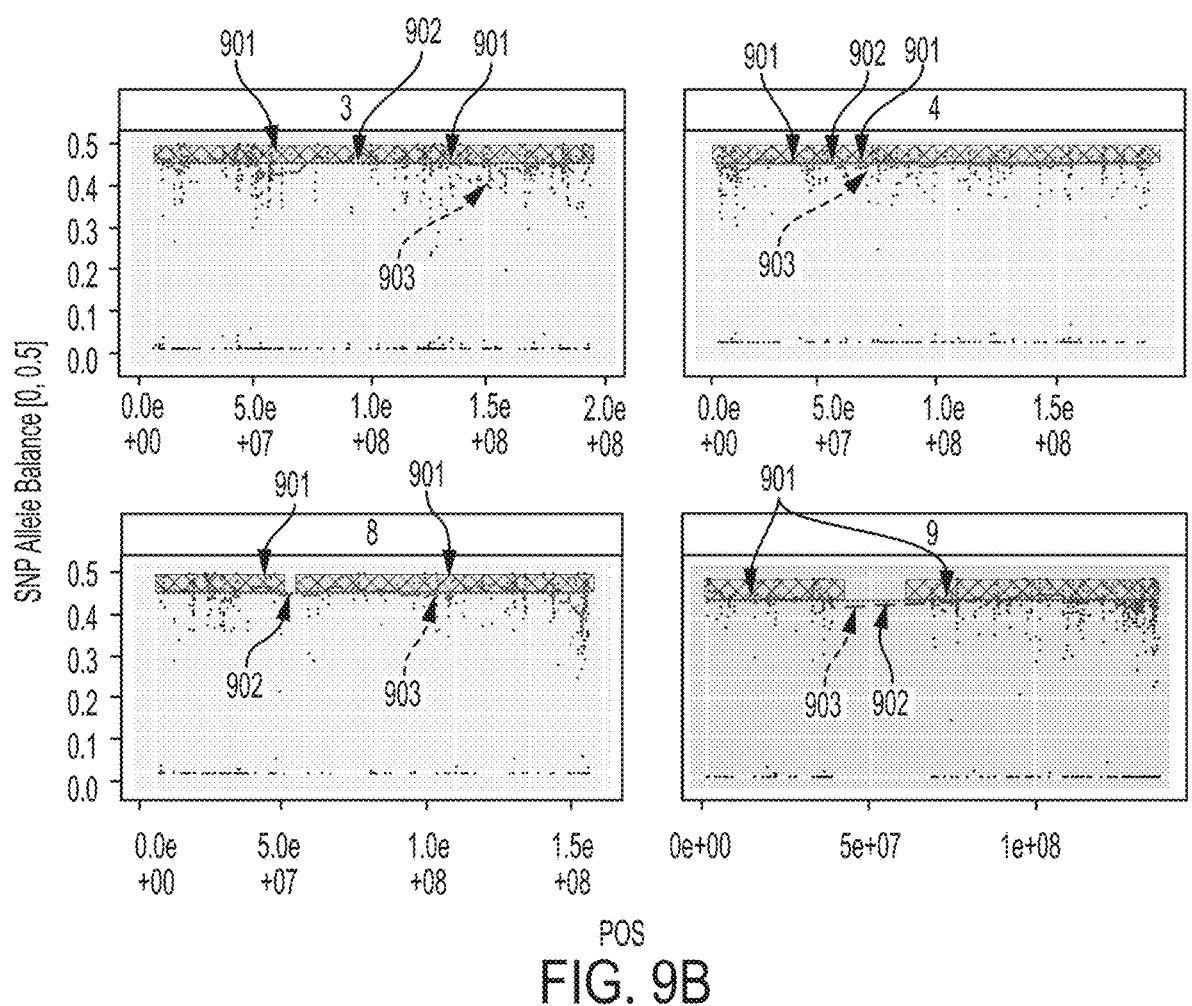
Figure 9C:
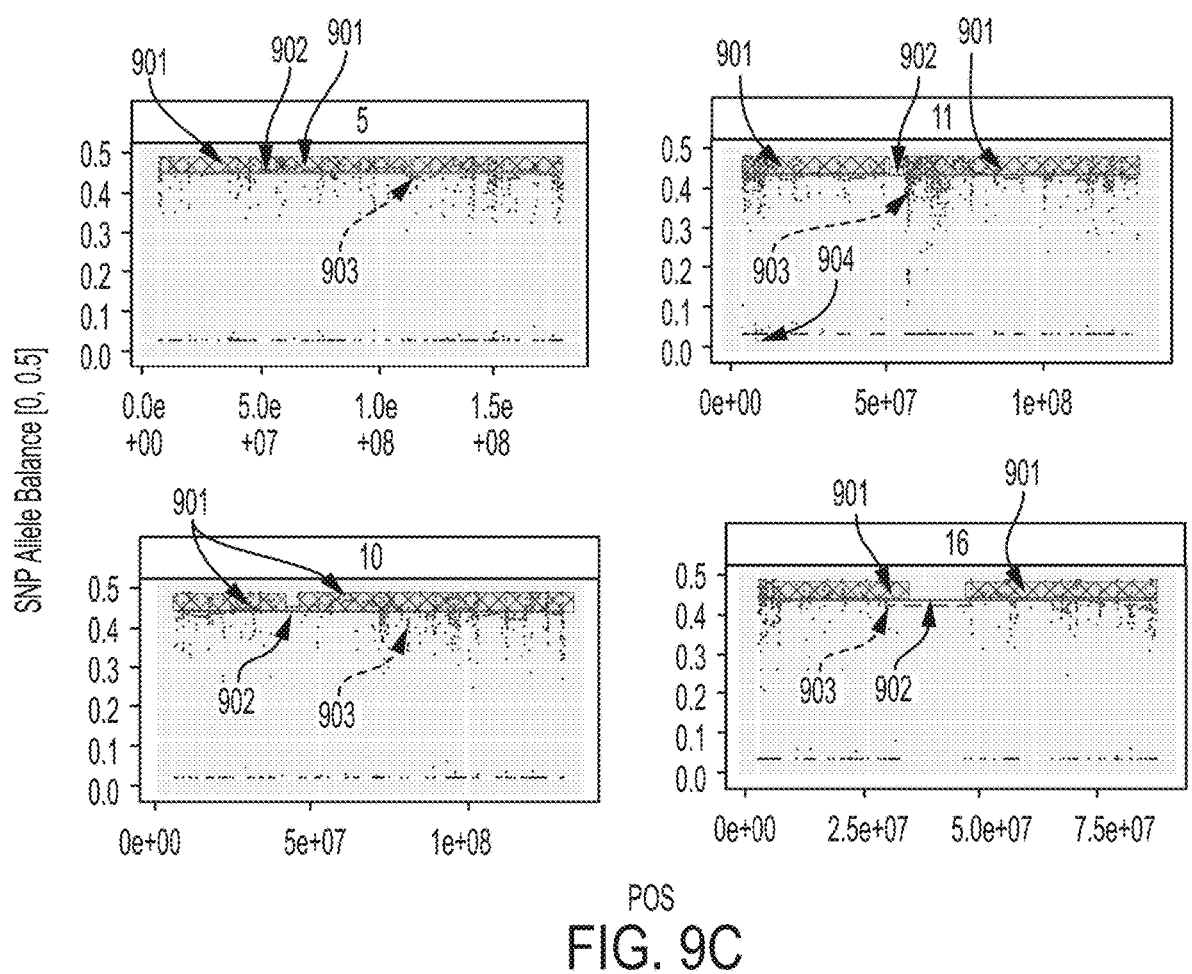
Figure 9D:
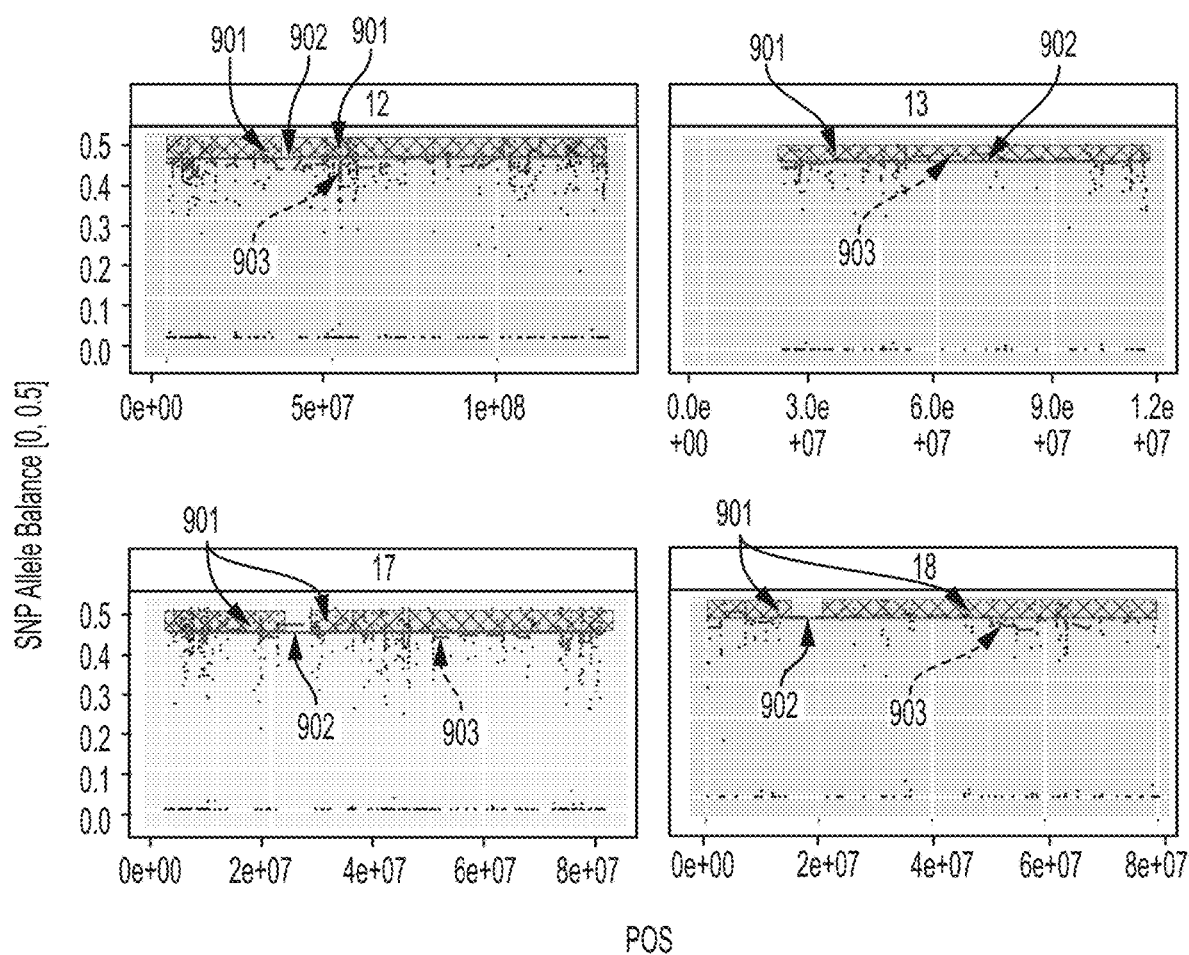
Figure 9E:
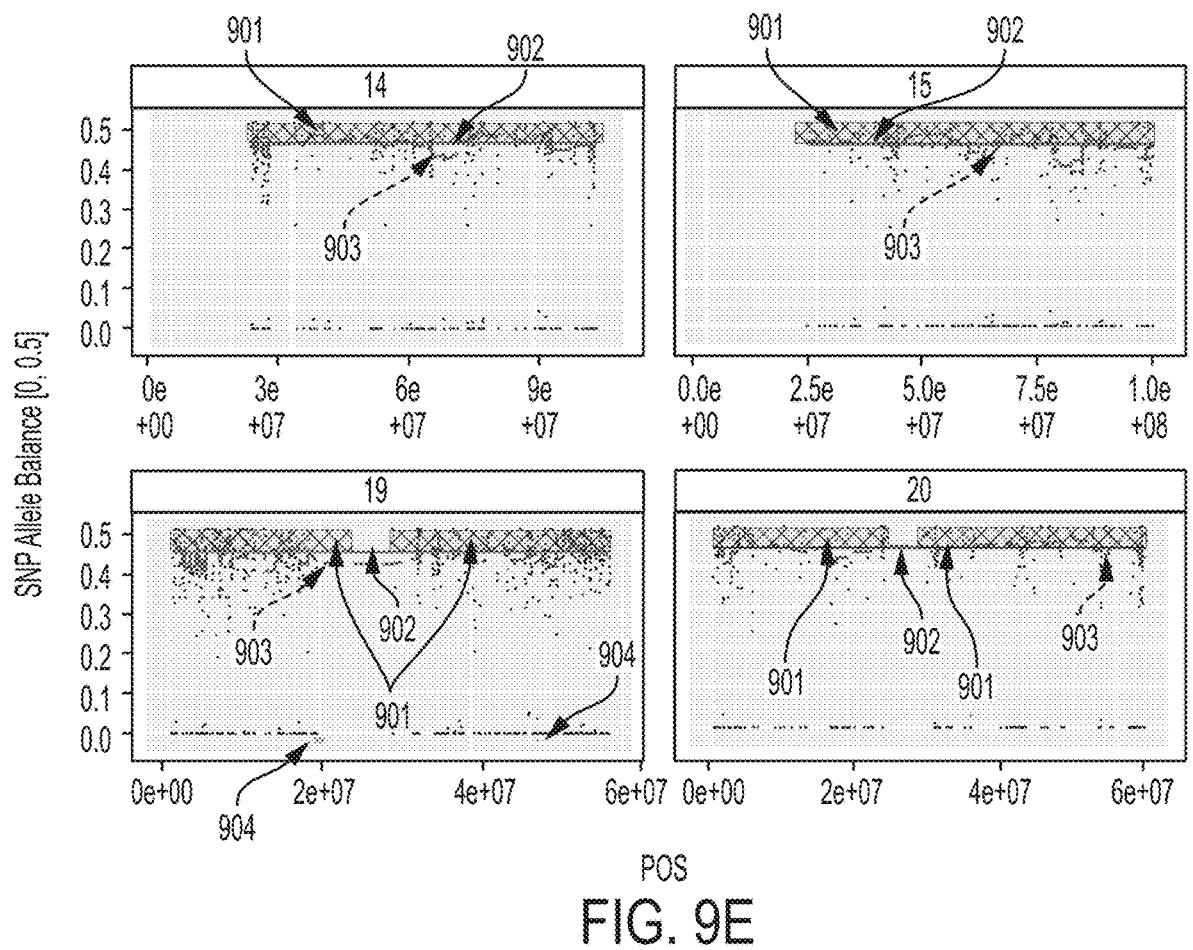
Figure 9F:
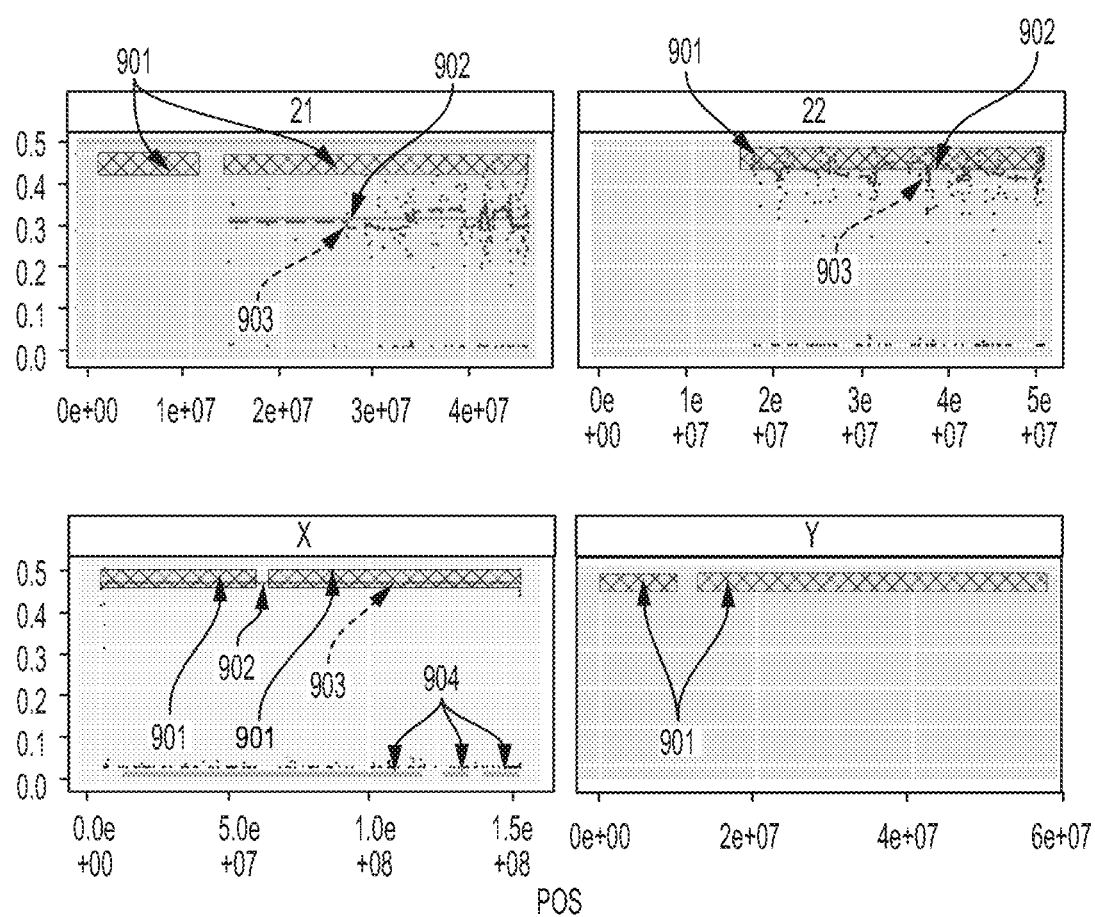

FIG. 7A-F are allele balance plots showing partial chromosome allele balance events for chromosomes 9, 13, and 20. The subplot number is the chromosome number. The shaded bar 701 denotes the normal range of variability expected for a heterozygous SNP allele balance of 0.5. The line 702 denotes the whole chromosome median allele balance. The dashed line 703 denotes the local median allele balance in an approximately 20 SNP rolling window. The line 704 denotes runs-of-homozygosity. FIG. 8 is a read coverage plot that shows a significant underrepresentation of reads for chromosomes 13 and 20 for the same sample.

Figure 10:
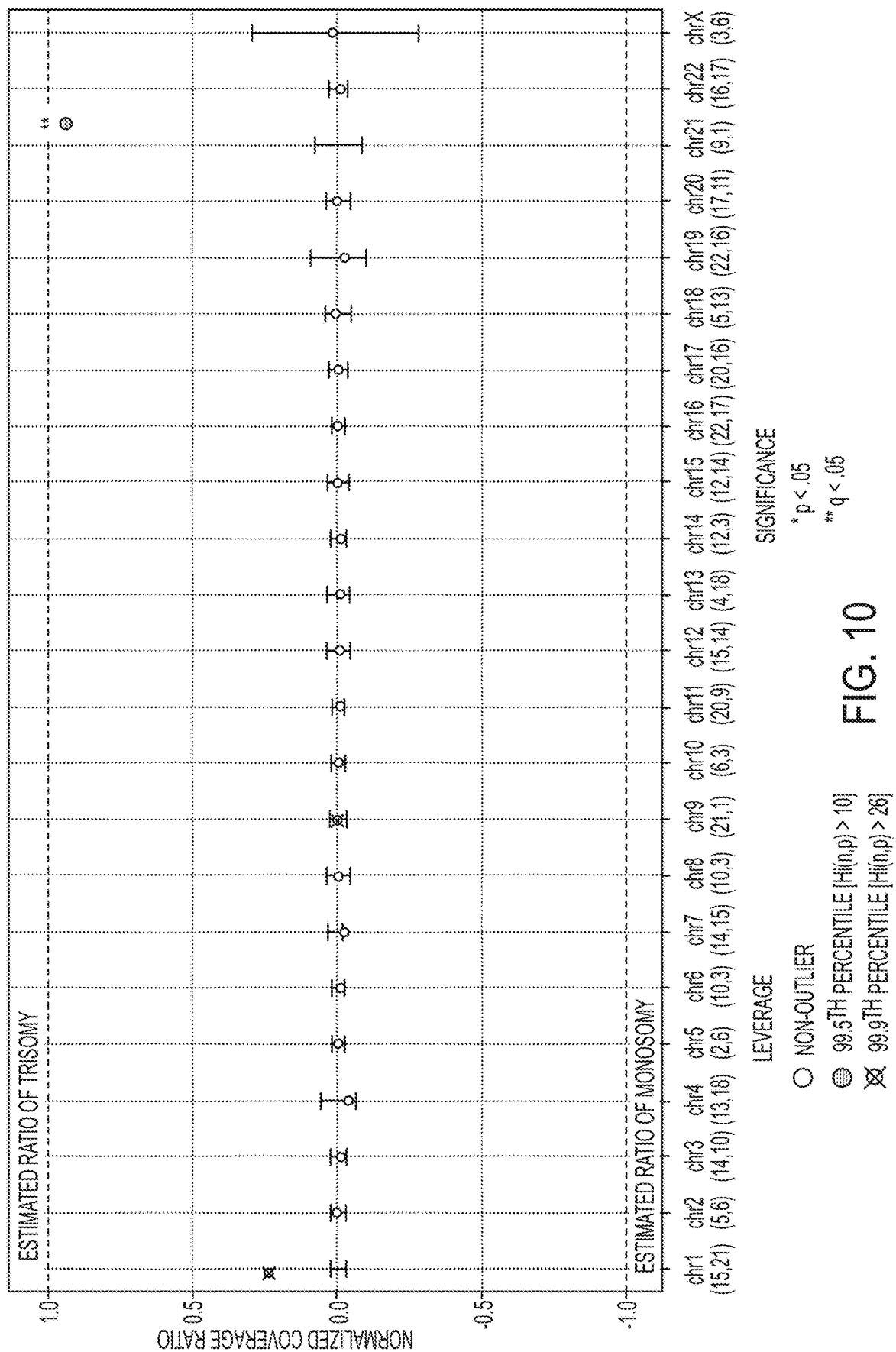
FIG. 10 is a read coverage plot for the same sample as in FIGS. 9A-F.

FIG. 9A-F are allele balance plots of a trisomy 21 sample (Down Syndrome). The allele balance plots show an anomaly on chromosome 21 in a sample and a run-of-homozygosity encompassing all of chromosome X, implying a karyotypically normal male sample having only one X chromosome. The shaded bar (901) denotes the normal range of variability expected for a heterozygous SNP allele balance of 0.5. The solid line (902) denotes the whole chromosome median allele balance. The dashed line (903) denotes the local median allele balance in an approximately 20 SNP rolling window. The line (904) denotes runs-of-homozygosity. FIG. 10 is a read coverage plot for the same sample.

Information obtained using the methods disclosed herein can be reported by a clinician to a patient, for example, in order to provide further clinical insight into an existing diagnosis, such as autism or an autism-spectrum condition.

Information obtained using the methods disclosed herein can also be used by a clinician to provide a patient with clarity about known or unknown fertility issues, for example, in a patient with a sex chromosome abnormality.

The methods disclosed herein can also be used to monitor cancer detection and development.

The methods disclosed herein can also be used to determine whether or not a DNA sample contains DNA from two individuals, which can occur, for example, if a DNA sample from one individual is contaminated with DNA from another individual. DNA can also come from two individuals when a twin demise/human chimera event occurs, i.e., a multiple gestation pregnancy in which not every fetus survives and a deceased twin's DNA becomes incorporated into a surviving fetus's DNA. In such situations, the result would be a skewed, multimodal allele balance for all regions of the genome in which the twins' DNAs are not identical, which is ~75% of the genome for dizygotic twins. DNA can also come from two individuals when blood or tissue from one individual is transplanted into another individual. DNA can also come from two individuals when maternal-fetal DNA is mixed when a non-invasive prenatal test sample is obtained.

Returning to FIG. 4, the method 400 can further comprise detecting one or more outliers and removing the one or more outliers from consideration for identification as an abnormal karyotype. Detecting one or more outliers can comprise flagging one or more of the plurality of samples having leverage ($h_i$, where $1/n < h_i < 1$) above a threshold on the linear regression model for each chromosome, wherein leverage is determined as a function of n and p:

$$h_i(n, p) = \left[\frac{1}{n} + \frac{(x - \bar{x})^2}{\sum_{j=1 \ldots n}(x_j - \bar{x})^2}\right] \cdot \frac{n}{p+1}$$

where p is the number of covariates in the model, $x_i$ represents a vector of covariates for sample i, and $\bar{x}$ is the vector of covariate means across the sample population. The threshold can be from about 3 to about 5.

Read coverage data can be computed from genome-aligned sequence reads that are generated prior to the KaryoScan method herein, for the purpose of detecting single nucleotide polymorphisms (SNPs), insertions and deletions (indels) for individual samples. SNPs having only two observed alleles (or one observed homozygous allele that differs from a second allele defined by the reference genome that is unobserved in the sequence reads of this particular sample) are termed bi-allelic SNPs. By focusing on bi-allelic SNPs, one can calculate the allele balance of a particular site in the genome.

In a further aspect, allele balance analysis can be used to identify one or more karyotypes. Allele balance is a measure of how many sequence reads support each allele. For example, if a heterozygous SNP is covered by 100 sequence reads, and the sample is diploid in this genomic region, 50 reads of one allele and 50 reads of the other allele can be expected, yielding an allele balance of 0.5/0.5. Because the allele balance of both alleles sums to 1 and is symmetric about 0.5, the focus is on the minor allele balance (e.g., the allele with fewer reads, or a randomly selected allele if the two alleles are exactly equal in coverage). In practice, the observed allele balance is rarely exactly 50%, but will follow a probability distribution that reflects how many reads of each allele occur over a sample of size N (N=number of aligned sequence reads) given a true proportion, p. Ideally, a heterozygous SNP in a diploid sample has p=0.5, and the allele balance could be modeled with a binomial distribution with an expected value of 0.5.

In a sample with a non-diploid region (trisomy 21, for example), bi-allelic heterozygous SNPs in the non-diploid region will not have an expected allele balance of 0.5. If one chromosome is duplicated, such as for trisomy 21, ⅔ chromosome 21 copies will have one allele, and ⅓ chromosome 21 copies will have the other, yielding an expected allele balance ~0.333. Therefore, by modeling the allele balance distribution over the entire chromosome with a measure of central tendency, one can validate a trisomy 21 call from the read depth model by ensuring that the corresponding allele balance converges to roughly 0.333. Metrics such as a median allele balance estimate across the chromosome can be used. Similarly, for a monosomy chromosome, only one allele can be present and no heterozygous SNPs will be identified. Therefore, allele balance will be 0 or entirely unobserved, and only homozygous SNPs (hemizygous) can be identified. These regions can be identified via runs-of-homozygosity.

Both of these examples assume a whole-chromosome duplication or deletion. However, partial chromosome duplications and deletions can also be observed in allele balance distributions. To distinguish partial chromosome events, one can use a local estimate of central tendency and identify deviations in this local estimate from the remainder of the chromosome. In practice, variance in allele balance is proportional to the number of reads covering the SNP, and the local estimate must be smoothed over a large enough number of sites to reduce the total variance contributed by individual sites. To achieve this smoothing, one can compute a rolling median over a window of 20 heterozygous bi-allelic SNPs. This window size can be increased or decreased depending on sequencing depth, as deeper sequencing has lower variance at each particular site due to an increased sample size. Similarly, runs-of-homozygosity can be identified that span only portions of the chromosome.

In addition to partial chromosome events, mosaic events (whole or partial chromosome) will also be reflected in allele balance distribution deviations. Mosaic events are events that occur in a subset of the cell population that provided DNA for the sequenced sample. Mosaicism can be a result of somatic mutation (such as in cancer) or in errors in early germline cell division. For example, if a whole chromosome deletion occurs in only 50% of sequenced cells, heterozygous SNPs from the deleted chromosome will have an expected 25% allele balance in addition to a 25% depletion in read coverage. Thus, allele balance can also be used to distinguish mosaic events.

Not all abnormal karyotypes result in a different number of chromosomes. Uniparental disomy (UPD), for example, occurs when a chromosome has two copies that come from the same parent, and no copies from the other parent. These events will not be detected in read coverage deviations, but can be identified from the heterozygous allele balance (if the event is mosaic) or from runs-of-homozygosity (if the event is not mosaic).

Anomalies in chromosomal coverage can also occur without causing an anomaly in allele balance. For example, if a chromosome is duplicated into four copies (tetrasomy), the resulting karyotype may have two chromosomes of each parental origin, yielding a normal allele balance of ~50%. This would have the same effect in both mosaic and non-mosaic events.

Figure 11:
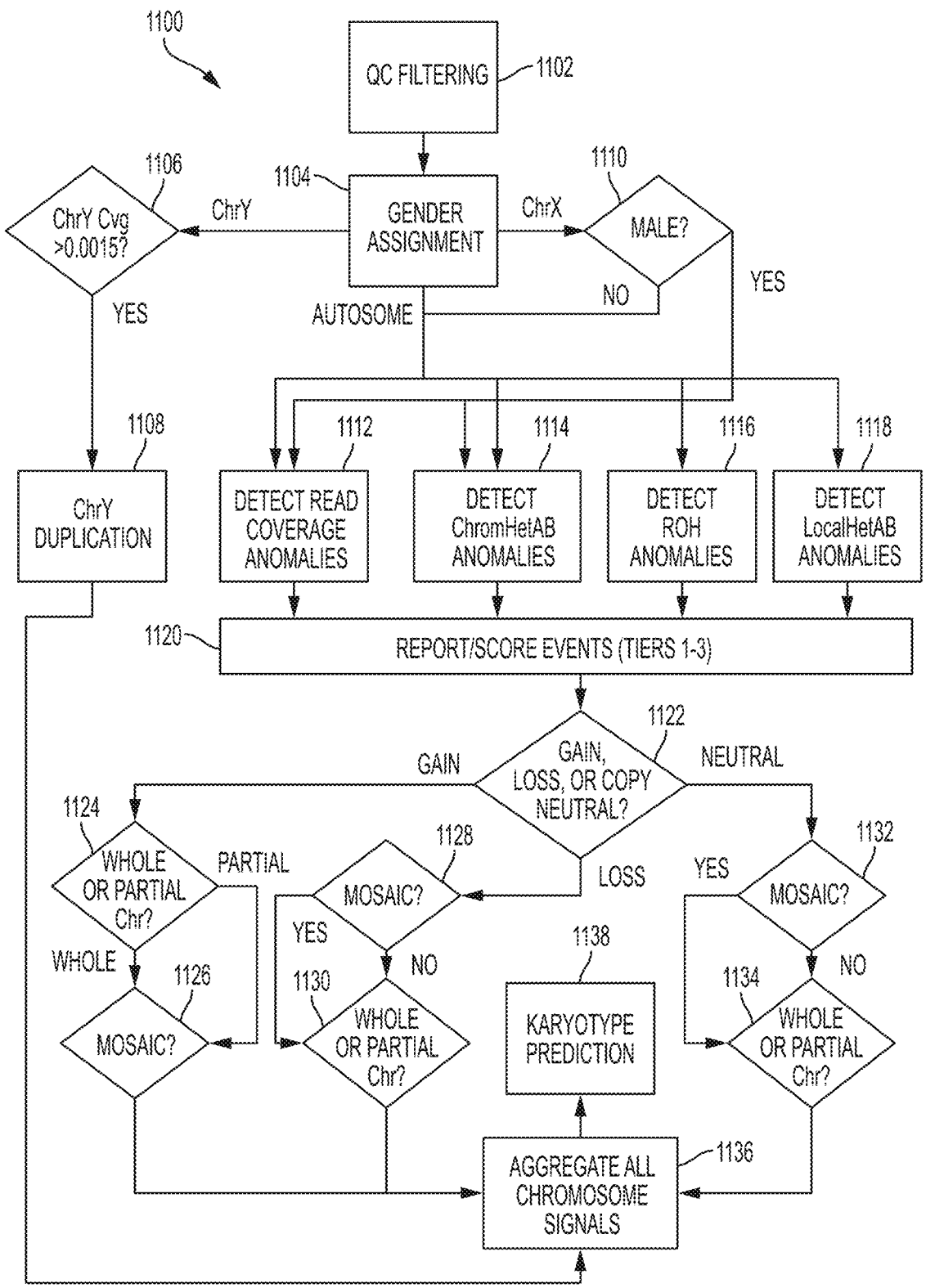
FIG. 11 is flowchart illustrating an example abnormal karyotype detection method.

FIG. 11 is a flowchart illustrating an example method 1100 for detecting abnormal karyotypes incorporating read coverage and allele balance analysis. The method 1100 can determine one or more metrics which are described here for convenience and referred to in the description of the method flow. The method 1100 can determine a variant allele balance which can be a variant-specific metric determined by calculating a minimum (# of alternate allele reads, # of reference allele reads)/total # reads. In one aspect, the method 1100 can utilize "AD" (allele depth) and "DP" (read depth) tags from one or more VCF files to determine the variant allele balance.

The method 1100 can determine a callable chromosome length which can be a chromosome-specific metric determined by calculating a # of base pairs between the first and last unfiltered exons on the chromosome−# of overlapping centromeric bases. The adjustment for centromeric bases accounts for seemingly large events that span the centromere, where no read coverage is present. In practice, genomic centromere boundaries can be adjusted to the nearest exonic boundaries. Similarly, restricting to the first and last unfiltered exons accounts for long telomeric regions without exon coverage, as well as for chromosomes having entire arms lacking exon coverage (e.g., many acrocentric chromosomes).

The method 1100 can determine a chromosome-wide heterozygous allele balance (referred to as ChromHetAB) which is a chromosome-specific metric that enables filtering for putative heterozygous SNPs whereby variant allele balance >0.02 (threshold can be adjusted closer to or further from 0 depending on sequencing depth). ChromHetAB can be a summary statistic (e.g., median) representing the chromosome-wide heterozygous SNP allele balance among all unfiltered variants within a chromosome. For example, ChromHetAB can be determined by calculating a median (variant allele balance) for all unfiltered variants within a chromosome. References to ChromHetAB with respect to a specific SNP, LocalHetAB Event, or ROH Event can refer to the ChromHetAB value for the chromosome on which the SNP or event occurs. ChromHetAB can be a summary statistic (e.g., median) representing the chromosome-wide heterozygous SNP allele balance among all unfiltered variants within a chromosome.

The method 1100 can determine a local median heterozygous allele balance (referred to as LocalHetAB) which is a variant-specific metric that enables filtering for possible heterozygous SNPs whereby variant allele balance >0.02

(threshold can be adjusted closer to or further from 0 depending on sequencing depth). LocalHetAB can be determined by calculating a running median of variant allele balance over an entire chromosome, using a 20 SNP window and constant ends. In an aspect, determining the LocalHetAB can comprises determining a smoothed, sub-chromosome scale (e.g., local) summary statistic (e.g., running median) of a sample's heterozygous SNP allele balance across all unfiltered variants on a chromosome.

The method 1100 can determine a contiguous region of two or more SNPs, all having LocalHetAB<ChromHetAB (referred to as a LocalHetAB Event). The method 1100 can define coordinates (start and end chromosomal position) by first and last SNP within the LocalHetAB Event. There can be zero to a plurality of LocalHetAB Events per chromosome. The method 1100 can determine a LocalHetAB Event Area by calculating a normalized "area under the curve" for LocalHetAB Events. For example, for a pair of neighboring SNPs within a LocalHetAB Event, determine a PairwiseArea=[ChromHetAB−Average(LocalHetAB(SNP1), LocalHetAB(SNP2))]*(SNP2 position−SNP1 position−# of overlapping centromeric base pairs). In the smallest form, a LocalHetAB Event can have exactly two neighboring SNPs. LocalHetAB events with more than two SNPs can be viewed as a chain of N−1 neighboring SNP pairs, where N=the # of SNPs in the event. LocalHetAB events with two or more SNPs can be determined by calculating a sum(PairwiseArea for all N−1 neighboring SNP pairs in the LocalHetAB Event)/(callable chromosome length*ChromHetAB).

The method 1100 can determine a summary allele balance (AB) statistic for a LocalHetAB Event (referred to as a LocalHetAB Event AB) by determining a minimum(LocalHetAB, for all SNPs in the LocalHetAB Event). Because LocalHetAB is a smoothed (running median) estimate of the allele balance, the minimum is a good estimate for the entire event. However, alternative metrics (e.g. mean, median, $1^{st}$ quartile, etc.) may be better suited in other applications (e.g. larger SNP window size, deeper sequencing, whole-genome sequencing, etc.).

The method 1100 can determine Runs-of-Homozygosity (referred to as ROH) which is a variant-specific metric for chromosomal regions where little-to-no heterozygosity is observed. ROH is a binary (yes/no) flag at every variant, but may have supporting metrics (e.g., confidence score). In an aspect, determining ROH can include use of the BCFtools/RoH method described by Narasimhan, V., et al. (2016) *Bioinformatics*, 32(11), 1749-1751), incorporated by reference herein in its entirety. Example options for ROH determination include, but are not limited to, Autozygous-to-Hardy Weinberg transition probability (−a option)=6.6e−09, Hardy Weinberg-to-Autozygous transition probability (−H option)=5.0e−10, Ignore indels (−I option), Restrict to SNPs within exons (i.e. no flanking region SNPs), and Utilize internal RGC (EVE) variant frequencies. In an aspect, one or more alternative method could be used. For example, Plink as described by Purcell S, Neale B, Todd-Brown K, et al. PLINK: A Tool Set for Whole-Genome Association and Population-Based Linkage Analyses. *American Journal of Human Genetics*. 2007; 81(3):559-575, incorporated by reference herein in its entirety.

The method 1100 can determine a contiguous region of one or more SNPs predicted as ROH (referred to as a ROH Event). Event coordinates can be defined as the chromosomal positions of the first and last SNP within the ROH Event.

Returning to FIG. 11, data for all samples can be subjected to quality control (QC) filtering at block 1102. The data can comprise, for example, VCF files (e.g., one VCF file per sample), depth of coverage files, and/or external quality control metrics (e.g., Picard metrics computed from a BAM read-mapping file). The VCF files can comprise marker and genotype data for gene sequence variations. The depth of coverage files can comprise indications of a number of reads that include a given nucleotide or sequence of nucleotides. QC filtering can comprise application of one or more sample filtering criteria to the depth of coverage files, VCF files, and/or external quality control metrics. The one or more sample filtering criteria can comprise, for example, standard contamination filters (such as high heterozygous to homozygous SNP call ratios), filtering based on low sequence coverage (<75% of bases at 20× coverage or higher), and/or filtering based on low DNA quality, combinations thereof, and the like. In an aspect, the QC filtering can comprise application of one or more variant filtering criteria to the VCF files. The one or more variant filtering criteria can comprise, for example, analyzing bi-allelic SNPs only (remove multi-allelic sites and indels), filtering based on minimum variant quality (QD>5, GT>30, pass VQSR filter [variant quality score recalibration]), filtering based on minimum read-depth (DP>=20), and/or filtering based on locus quality (1. only exons with >90% mappability, 2. exclude exons where >2 copies is common (e.g. multi-copy CNV loci), 3. exclude other regions with mappability issues (e.g. HLA genes)), combinations thereof, and the like.

At block 1104, gender assignment can be performed on data associated with samples that pass through the QC filtering at block 1102. Gender assignment can comprise determining a minimum chromosome Y read coverage ratio (relative to a chromosome X read coverage ratio) to determine if a sample is male (above the threshold) or female (below the threshold). FIG. 13A is a plot of chromosome X versus chromosome Y coverage ratios for all samples and a threshold for determining male (1302) and female (1304) samples indicated by the solid line 1306. Additionally, male samples having chromosome Y duplications can be identified using a chromosome Y coverage ratio threshold (dashed line 1308). If sample genders are already known or reported for samples, the existing assignments can be used to help determine appropriate thresholds. After gender assignment at block 1104, each chromosome from the sample(s) can be processed via one or more of the remaining blocks of the method 1100.

If the sample is deemed male, the method 1100 will proceed to block 1106. At block 1106, the method 1100 can determine if coverage of the Y chromosome is greater than a threshold, for example, 0.0015. If the coverage of the Y chromosome is greater than the threshold, the method 1100 can determine at block 1108 that there has been a duplication of the Y chromosome and proceed to block 1138 as the Y chromosome can be treated independently of other chromosomes. If the coverage of the Y chromosome is less than the threshold, the method 1100 can determine at block 1108 that the sample has a normal dosage of Y chromosome reads for a male sample and therefore no detectable anomaly occurs on the Y chromosome.

Returning to block 1104, gender assignment can comprise determining whether the sample is expected to have one or two X chromosomes (male or female), in which case the method 1100 will proceed to block 1110 to process chromosome X for the sample. At block 1110, the method 1100 can determine whether the data is derived from a male. If at block 1110, it is determined that the data is derived from a male, the method 1100 will proceed to blocks 1112 and 1114. If at block 1110, it is determined that the data is not derived from a male, the method 1100 will proceed to blocks 1112, 1114, 1116, and 1118. Returning to block 1104, gender assignment can comprise determining that the data comprises an autosome, in which case the method 1100 will proceed to blocks 1112, 1114, 1116, and 1118.

At block 1112, the method 1100 can detect read coverage anomalies. Block 1112 can be performed as described herein with reference to one or more portions of FIG. 1 and/or FIG. 4. At block 1114, the method 1100 can detect ChromHetAB anomalies. At block 1116, the method 1100 can detect ROH anomalies. At block 1118, the method 1100 can detect LocalHetAB anomalies.

Figure 12:
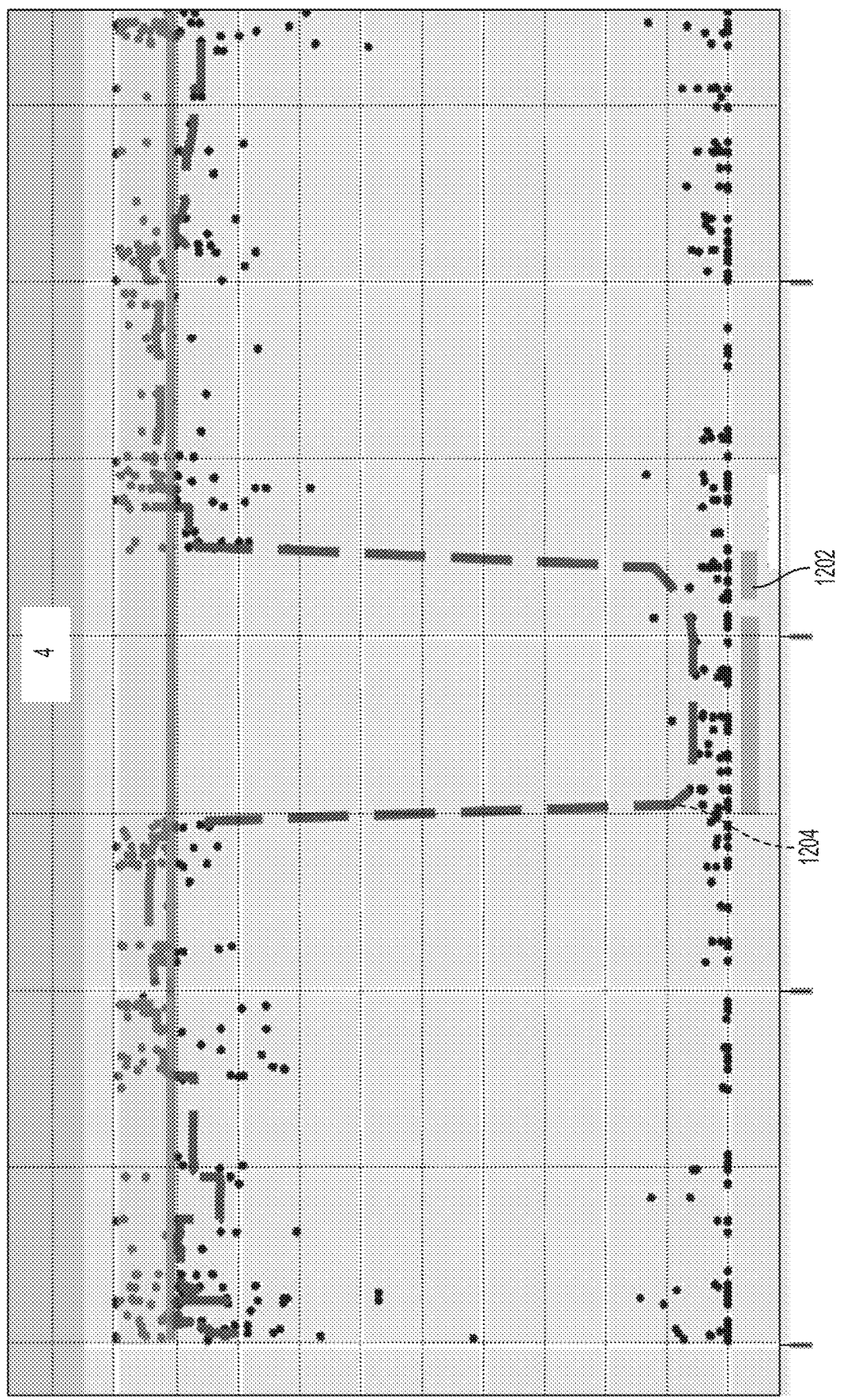
FIG. 12 is an example allele balance plot of a sample on chromosome 4, in which a large run-of-homozygosity is detected (1202) that has an overlapping LocalHetAB Event (1204) due to small amounts of non-zero allele balance among homozygous SNPs in the anomalous region.

Blocks 1114, 1116, and 1118 related to determination of three allele-balance metrics (ChromHetAB, ROH, and LocalHetAB, respectively). These three allele-balance metrics can be used for detecting different types of anomalies, but can result in overlapping evidence. For example, ROH can be used for identifying constitutional chromosomal deletions (whole or partial chromosome), as heterozygosity should not be observed in these regions. Similarly, ROH can identify large uniparental disomy (UPD) events (copy neutral, whole or partial chromosome), but is not useful for identifying duplications. However, the LocalHetAB and ChromHetAB metrics may also produce anomalous signals within an ROH event by identifying small amounts of noise (due to technical artifacts, such as sequencing errors) resembling putative heterozygosity, having variant allele balance values close to 0; these signals can be ignored in lieu of the ROH anomaly (see FIG. 12, representing an ROH event with an overlapping LocalHetAB event). FIG. 12 is an example allele balance plot of a sample on chromosome 4, in which a large run-of-homozygosity is detected (1202) that has an overlapping LocalHetAB Event (1204) due to small amounts of non-zero allele balance among homozygous SNPs in the anomalous region. In the case of a whole chromosome duplication or other mosaic whole chromosome event, ChromHetAB can be the most relevant metric; it should equal roughly ⅓ for a trisomy, or a fraction representative of the copy number and cellular fraction of a mosaic event. For a partial chromosome event, LocalHetAB can be the most relevant metric as it will detect event start and end coordinates. However, a large, partial chromosome event can also influence the chromosome-wide ChromHetAB metric, creating an anomalous signal that is better captured by the LocalHetAB event.

Thus, balancing the evidence provided by each metric (and interpreting each relative to read coverage anomaly signals) can be a component of automating the detection and characterization of a chromosomal anomaly. To handle integrating these signals that have differences in sensitivity, specificity, scale, and context, three Tiers of putatively anomalous signals can be defined for each metric, where Tier 1 signals are the most significant and Tier 3 are the least. Tier ratings are used to standardize and integrate these heterogeneous metrics, enabling simple decisions as to which signals are most relevant. Other numbers of Tiers can be used and defined.

Returning to block 1112, detection of read coverage anomalies can utilize the following Tier definitions. Tier 1 can comprise read coverage p-value<a threshold, such as 0.05/(# of chromosome/sample pairs tested). Bonferroni-correction can be applied with a family-wise error rate=5%. Tier 2 can comprise not passing Tier 1 and chromosome-specific FDR-corrected p-value (q-value)<a threshold, such as 0.05. Benjamini-Hochberg FDR correction can be applied with a false discovery rate=5% per chromosome. Tier 3 can comprise not passing Tier 1 or Tier 2 and read coverage p-value<a threshold, such as 0.05. One or more exceptions can apply to X Chromosome analysis. For example, Tier 3 signals on chrX can be promoted to Tier 2 if the absolute value (magnitude) of the estimated chromosomal dosage fraction is >5%.

Figure 13B:
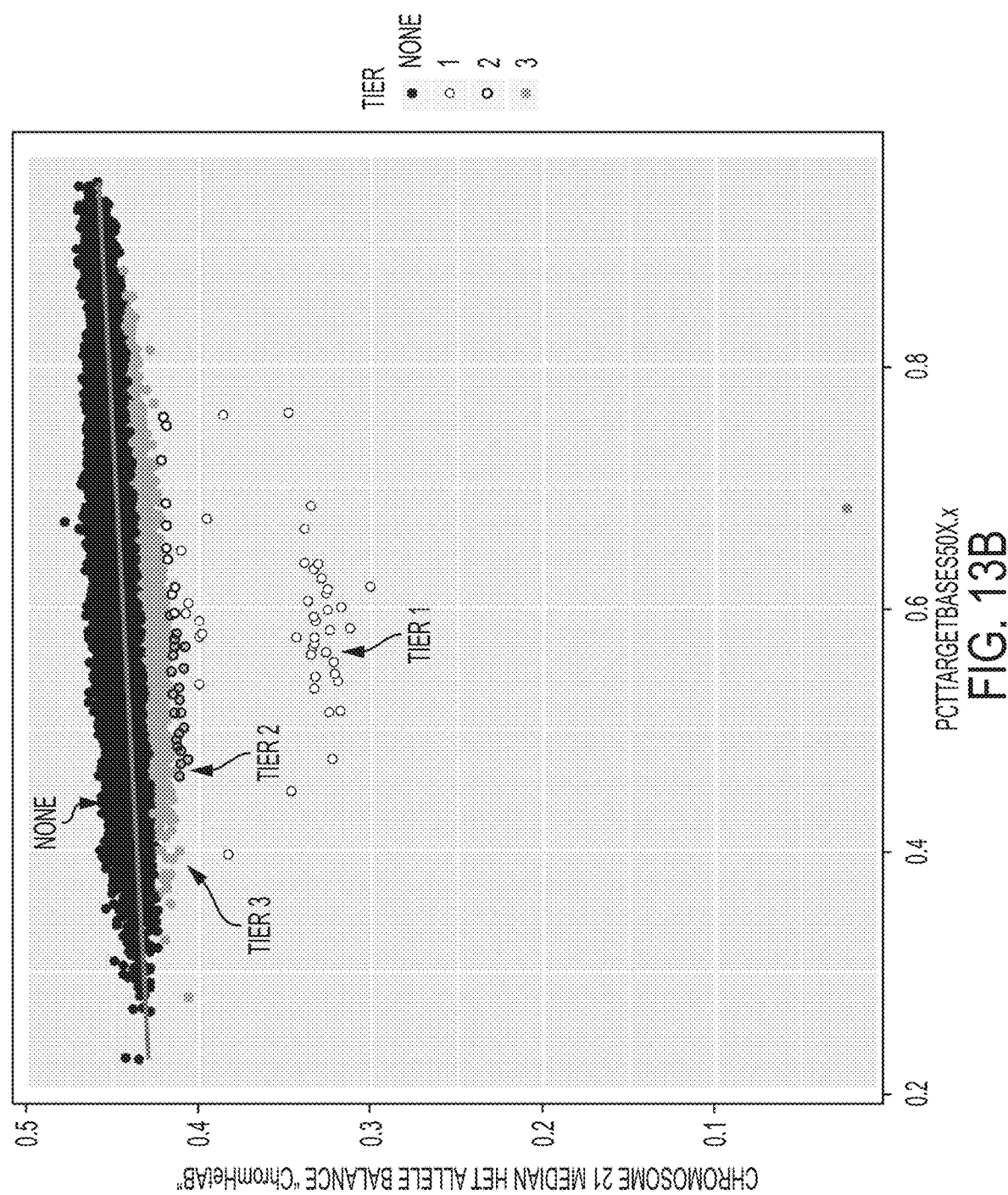
FIG. 13B is an example plot for chromosome 21 demonstrating that the expected chromosome-wide median heterozygous SNP allele balance (ChromHetAB) increases relative to the fraction of bases covered at or above a specific read depth threshold (e.g., 50× coverage, "PCTTARGET- BASES50×" QC metric); "tier" ratings can be assigned based on the significance of the deviation in the observed versus expected ChromHetAB based on the coverage metric.

Returning to block 1114, because the variant allele balance metric always reflects the fraction of reads from the allele of a bi-allelic SNP with fewer reads, the expected ChromHetAB value for a karyotypically normal, diploid sample on a given chromosome is unlikely to be exactly 50%, but approaches 50% as sequencing depth increases. Therefore, a linear regression can be fit on the ChromHetAB values for all samples on a given chromosome (females only for chromosome X) relative to the PCTTARGETBASES50× quality control metric (calculated per sample using Picard) (FIG. 13B, showing an increasing ChromHetAB value among karyotypically normal samples relative to increasing PCTTARGETBASES50× values, and the identification of anomalous signals [colored dots] at different significance tiers). Once the linear regression model has been fit, a Z-score can be calculated for the residual of every sample's ChromHetAB value (observed ChromHetAB−expected ChromHetAB as defined by the regression). The Z-score can be calculated as Z=(sample residual)/(residual standard deviation of the regression model). The Z-score can be transformed into a p-value.

Figure 14:
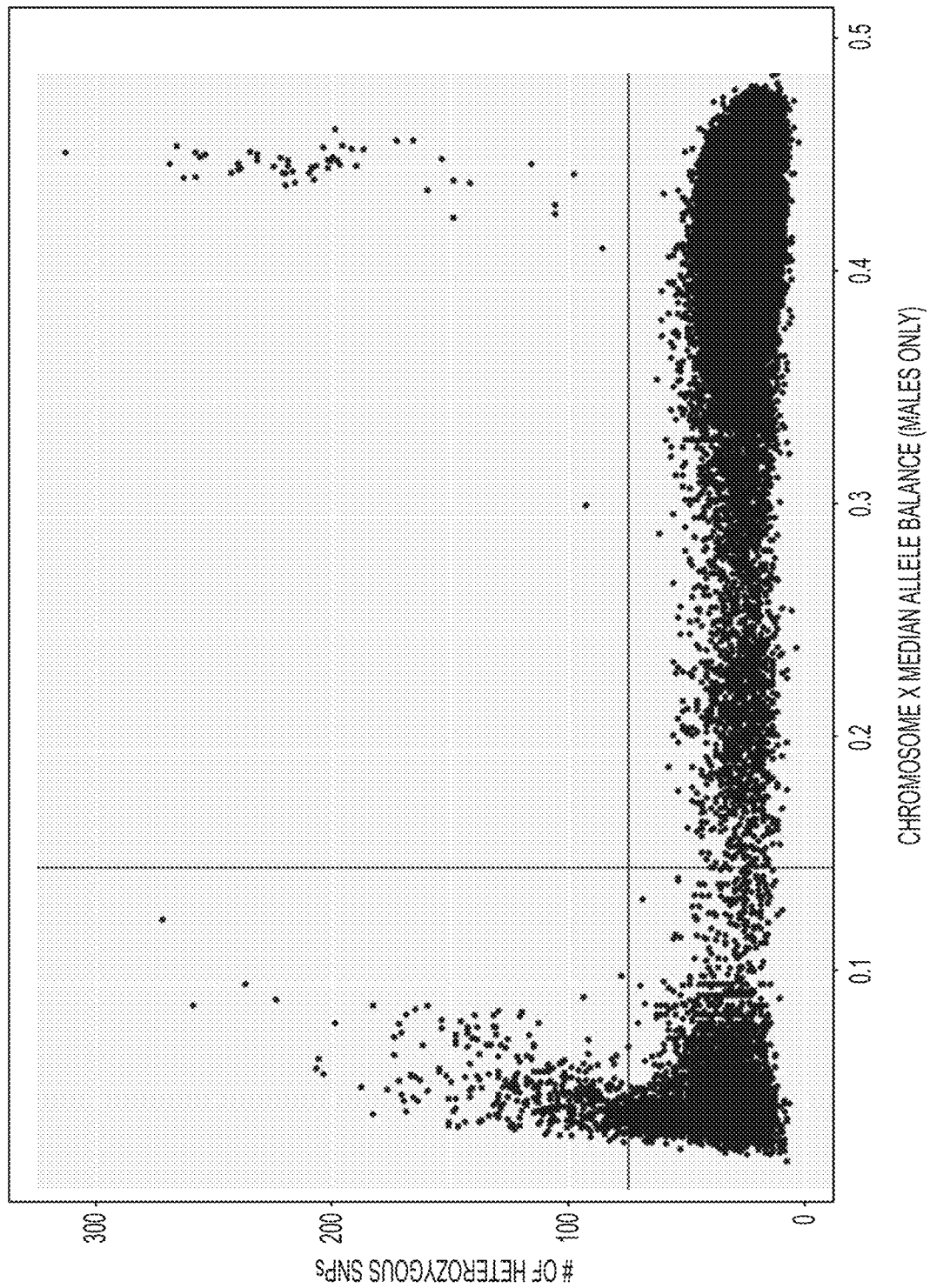
FIG. 14 is a plot of the ChromHetAB value (x-axis) for all male samples on chromosome X relative to the number of SNPs included in the ChromHetAB value's calculation (putative heterozygous SNPs; y-axis). Lines indicate thresholds to distinguish male samples having duplications on chromosome X based on high, non-zero ChromHetAB values supported by a large number of SNPs.

At block 1114, detection of ChromHetAB anomalies can utilize the following Tier definitions. Tier 1 can comprise ChromHetAB residual p-value<a threshold, such as 0.05/(# of chromosome/sample pairs tested). Bonferroni-correction can be applied with a family-wise error rate=5%. Tier 2 can comprise not passing Tier 1 and passing a chromosome-specific FDR-corrected p-value (q-value)<a threshold, such as 0.05. Benjamini-Hochberg can be applied with a FDR correction False discovery rate=5% per chromosome. Tier 3 can comprise not passing Tier 1 or Tier 2 and ChromHetAB residual p-value<a threshold, such as 0.05. One or more exceptions can apply to X Chromosome analysis. If a sample is male, ChromHetAB can be ignored and not tested unless >75 SNPs are included in the metric's calculation and the ChromHetAB >0.15. These filters allow for chrX duplications in males to be included if they have a ChromHetAB value much larger than expected (i.e., zero for a single X chromosome) and having a sufficient number of SNPs used to call the ChromHetAB value confidently, while removing noise from karyotypically normal male samples (FIG. 14, showing the ChromHetAB value and number of putatively heterozygous SNPs tested on chromosome X for male samples, with minimum thresholds indicated by solid lines). In this context, defining a male sample can refer to the assignment (based on X and Y read coverage) to have an expectation of one X and one Y chromosome, assuming a karyotypically normal state. Any male ChromHetAB signal from chrX passing these filters can be assigned to Tier 1 (regardless of p-value). In an aspect, detecting a ChromHetAB anomaly can comprise identifying a sample with a ChromHetAB value that is significantly smaller than the ChromHetAB value (or range of values) expected for a karyotypically normal sample Returning to block 1116, ROH anomalies can be detected. Small ROH events are relatively common in karyotypically normal samples, and can be particularly frequent among consanguineous samples, for example. Therefore minimum size thresholds for ROH events can be defined to capture only large, chromosome-scale events. ROH event detection can be challenging when truly homozygous variants have non-zero variant allele balance due to technical artifacts. As a result, some large ROH events get fragmented into two or more ROH events (FIG. 12). Thus independent ROH events within a chromosome are considered in combination. Detection of ROH Anomalies can utilize the following Tier definitions. ROH events having length (excluding overlapping centromeric bases)<5,000,000 bp can be filtered. Tier 1 can comprise the total (genome-wide) number of non-centromeric ROH bases from unfiltered ROH events>=20,000,000. Tier 2 can comprise unfiltered ROH events not passing Tier 1. One or more exceptions can apply to X Chromosome analysis. All ROH signals for male samples on chrX can be ignored. In this context, defining a male sample refers to the assignment (based on X and Y read coverage) to have an expectation of one X and one Y chromosome, assuming a karyotypically normal state.

Figure 15:
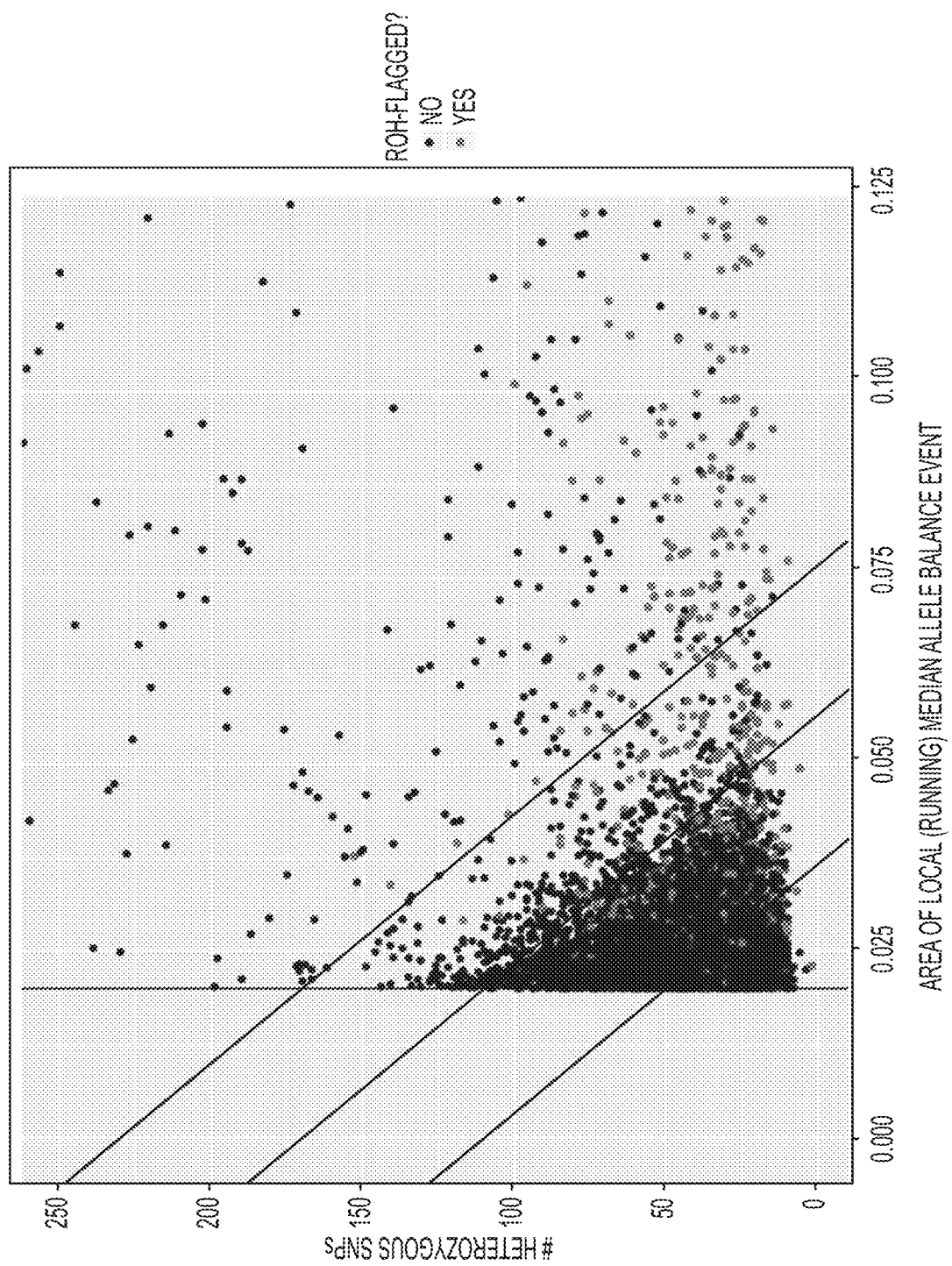
FIG. 15 is a plot of all LocalHetAB Events, black and grey dots, (with area greater than an example threshold, vertical line) relative to the number of heterozygous SNPs included in the event (y-axis), with diagonal lines demonstrating example tier rating thresholds. Grey dots indicate events having overlapping ROH events.

Returning to block 1118, LocalHetAB anomalies can be detected. Qualitatively, significant LocalHetAB Event anomalies should have large LocalHetAB Event Area metrics and be supported by a large number of included SNPs. A linear function can be defined to empirically fit to the exome data set relating LocalHetAB Event Area and # of SNPs included in the LocalHetAB Event ("# of SNPs"), with tier definitions defined using different intercepts on the same slope coefficient (e.g., minimum # of SNPs required for an event having a particular LocalHetAB Event Area). See FIG. 15 showing all LocalHetAB events (dots) with area >0.02 (vertical line) and their separation into tiers based on the regions between diagonal lines (red points indicate an overlapping ROH event exists, providing supporting evidence that the LocalHetAB event is detecting an anomaly). Detection of LocalHetAB anomalies can utilize the following Tier definitions. Events where LocalHetAB Event Area <0.02 can be filtered. Tier 1 can comprise # of SNPs+(LocalHetAB Event Area*a first amount such as 3000)>=a second amount such as 230. Tier 2 can comprise # of SNPs+(LocalHetAB Event Area*a first amount such as 3000)>=a second amount such as 170. Tier 3 can comprise # of SNPs+(LocalHetAB Event Area*a first amount such as 3000)>=a second amount such as 110. One or more exceptions can apply to X Chromosome analysis. All LocalHetAB signals for male samples on chrX are ignored. In this context, defining a male sample refers to the assignment (based on X and Y read coverage) to have an expectation of one X and one Y chromosome, assuming a karyotypically normal state. In an aspect, detecting a LocalHetAB anomaly can comprise where the LocalHetAB value falls below (e.g., significantly below) the corresponding ChromHetAB value over a chromosomal region, indicating a possible partial chromosome anomaly.

The analysis performed at blocks 1112, 1114, 1116, and 1118 for the disclosed metrics contribute to a chromosomal anomaly prediction. However, the metrics can be annotated with tier ratings, filtered to remove non-anomalous metrics, and aggregated at block 1136 prior to karyotype prediction at block 1138. At block 1120, the method 1100 can report anomalous events identified by each metric from blocks 1112, 1114, 1116, and 1118, and score each event into Tiers (e.g., Tier 1, Tier 2, Tier 3, etc. . . . ) that standardize the scaling between metrics and simplify their aggregation for abnormal karyotype (chromosomal anomaly) assessment. In an aspect, the method 1100 can report and/or score events for each of the one or more Tiers (e.g., Tier 1, Tier 2, Tier 3, etc. . . . ) used. At block 1112 the read coverage anomaly metric can be used for assessing chromosomal dosage and the remaining three can be used to assess allele balance and zygosity (ChromMedAB, ROH, and LocalHetAB events).

At block 1122, the method 1100 can determine whether the event reflects a copy gain, a copy loss, or is copy neutral. This assessment can be made primarily based on the presence or absence of a read coverage anomaly, but supplementary information from allele balance-related metrics can also be considered. For example, all Tier 1 read coverage anomalies may be predicted as gains or losses independently, but Tier 2 and/or Tier 3 read coverage anomalies may only be deemed gains or losses if a supporting allele balance anomaly is also detected on the same chromosome. If no read coverage anomaly is detected to call a gain or loss, the event is assumed to be copy neutral, and may additionally be flagged as uncertain if a low-quality read coverage anomaly is detected but filtered.

If at block 1122, it is determined that the event reflects a copy gain, the method 1100 can proceed to block 1124 to determine if the underlying chromosome is a whole or a partial chromosome, based on comparison of anomalous LocalHetAB and ChromHetAB events on the chromosome. For example, if a LocalHetAB event has a lower tier rating (e.g. more significant) than an overlapping ChromHetAB event (or if no ChromHetAB event is reported), the event may be predicted as partial chromosome given that the LocalHetAB event is more significant. Conversely, a lower tier ChromHetAB event would suggest a whole chromosome event is more likely the case. If both events occur at the same tier rating, the method may report the anomaly as uncertain and/or favor one event as more heavily weighted (e.g. favor LocalHetAB and call a partial chromosome event). Furthermore, the method may also compare estimates of the chromosomal fraction gain computed from the read coverage 11 to similar estimates from each allele balance anomaly, and weight the allele balance events by how closely their estimates match the estimate from read coverage. Whether the underlying chromosomal anomaly is predicted to be whole (ChromHetAB) or partial (LocalHetAB) chromosome, the method 1100 can proceed to block 1126 and utilize the respective allele balance metric to determine if the copy gain is a mosaic event by determining how close the heterozygous allele balance estimate is to 1/N, where N is the number of chromosomal copies predicted (e.g. ⅓ for a single copy autosomal gain). One may apply an error threshold around this expected rate (e.g. ⅓±0.02) to make a binary (yes or no) classification for mosaicism. If no overlapping LocalHetAB nor ChromHetAB event is reported, one may assign the chromosomal and mosaic fraction estimates to uncertain and/or set a default value.

If at block 1122, it is determined that the event reflects a copy loss, the method 1100 can proceed to block 1128 to determine if the copy loss is a mosaic event by utilizing ROH. If the copy loss is not mosaic (e.g., an ROH event is detected), the method 1100 can utilize ROH to determine if the underlying chromosomal anomaly is whole or partial by assessing what proportion of the callable chromosome is covered by ROH events. If a copy loss is mosaic (e.g., no ROH event reported) the method 1100 can utilize and compare tier ratings from reported ChromHetAB and LocalHetAB events to determine if the underlying chromosome is whole or partial. This assessment is similar to that of copy gains (block 1124), where a more significant LocalHetAB event may indicate a partial chromosome event and a more significant ChromHetAB event may indicate a whole chromosome event, and an allele balance-based estimate of chromosomal fraction can be compared to the read coverage event's chromosomal fraction estimate.

If at block 1122, it is determined that the event is copy neutral, the method 1100 can proceed to block 1128 to determine if the copy neutral event is a mosaic utilizing ROH. If the copy neutral event is not mosaic (e.g., an ROH event is reported), the method 1100 can utilize ROH to determine if the underlying chromosome is whole or partial. If the copy neutral event is a mosaic the method 1100 can utilize ChromHetAB and LocalHetAB to determine if the underlying chromosome is whole or partial.

The output of blocks 1126, 1130, and 1134 flow to block 1136 where every anomaly can be reported with one or more of: 1) prediction of copy neutral, copy gain, or copy loss; 2) prediction of a whole or partial chromosome event; 3) prediction of mosaic or not mosaic; 4) a final tier rating, which can be equal to the minimum (most significant) tier rating for all events reported on the chromosome, or can be additionally modified to up- or down-weight anomalies if they have multiple mid-tier events (e.g., a tier 2 read coverage event with a supporting tier 2 LocalHetAB event may be deemed tier 1); and 5) a summary of some or all events reported for the chromosome, their tier ratings, and whether they were chosen as a primary or supporting event (e.g., for a non-mosaic, whole chromosome loss with tier 1 read coverage, ROH, and ChromHetAB events, read coverage and ROH are primary events, but ChromHetAB is a supporting event despite being tier 1, given that it was trumped by the overlapping ROH event). Block 1136 receives anomalies from zero or a plurality of chromosomes and aggregates them for a sample, then proceeds to block 1138 to make a final karyotype prediction.

The output of block 1138 represents a karyotype prediction, where some or all chromosomal anomalies have been aggregated for a sample and interpreted relative to the expected karyotype (given the gender assignment from block 1104). This may be represented as a traditional karyotype coding (e.g., "47,XXY") and/or a list of anomalies and their supporting information. Given the uncertainty of an automated karyotype prediction and the fact that certain complex karyotypes (e.g. isochromosomes) have unique patterns not easily interpreted automatically, supporting read coverage and allele balance diagnostic plots can be computed by block 1138 for every sample, enabling manual inspection of predicted chromosomal anomalies and their supporting evidence. In an aspect, final anomalous karyotype calls can comprise one or more of: Sample; Chromosome; Start/End coordinates; Dosage change vs. copy neutral prediction (gain, loss, neutral, uncertain); Whole vs. partial chromosome event prediction (whole, partial, uncertain); Predicted mosaic event (yes, no, uncertain); Fraction estimate from read coverage, (i.e. chromosomal fraction*mosaic fraction, where a single copy, non-mosaic chromosomal gain=1, or loss=−1); Fraction estimate from allele balance (based on the anomalous allele balance metric deemed most relevant if more than one exists); Summary of all Tier 3 or greater anomalous signals for this sample/chromosome pair; Final, integrated tier rating; Supporting read coverage and allele balance diagnostic plots (such as the type illustrated in FIG. 2, FIG. 3, FIG. 5, FIG. 6, FIG. 7, FIG. 8, FIG. 9, and/or FIG. 10), allowing manual inspection and classification of the karyotype; combinations thereof, and the like.

Figure 16:
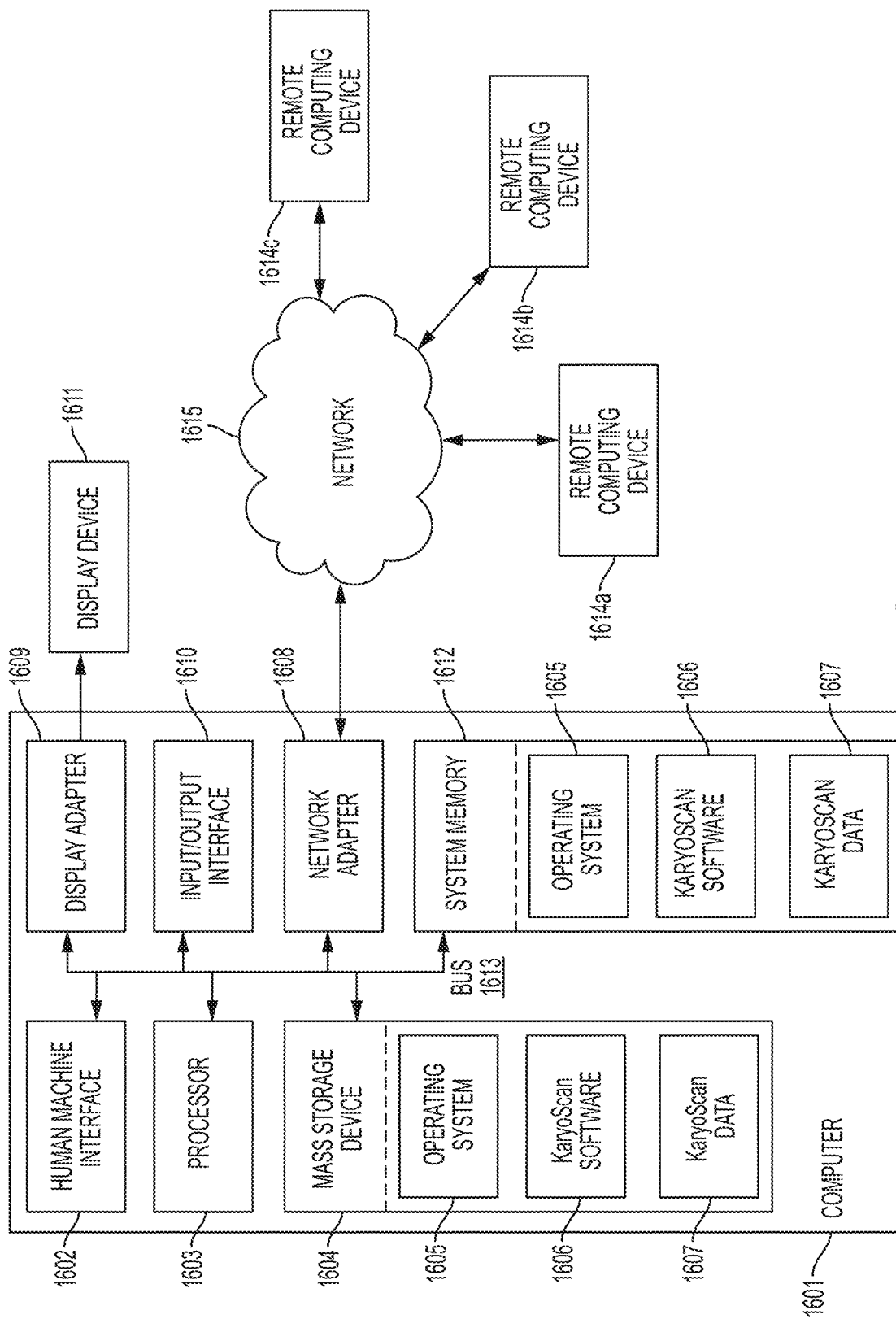
FIG. 16 is a block diagram illustrating an exemplary operating environment for performing the disclosed methods.

In an exemplary aspect, the methods and systems can be implemented on a computer 1601 as illustrated in FIG. 16 and described below. Similarly, the methods and systems disclosed can utilize one or more computers to perform one or more functions in one or more locations. FIG. 16 is a block diagram illustrating an exemplary operating environment for performing the disclosed methods. This exemplary operating environment is only an example of an operating environment and is not intended to suggest any limitation as to the scope of use or functionality of operating environment architecture. Neither should the operating environment be interpreted as having any dependency or requirement relating to any one or combination of components illustrated in the exemplary operating environment.

The present methods and systems can be operational with numerous other general purpose or special purpose computing system environments or configurations. Examples of well-known computing systems, environments, and/or configurations that can be suitable for use with the systems and methods comprise, but are not limited to, personal computers, server computers, laptop devices, and multiprocessor systems. Additional examples comprise set top boxes, programmable consumer electronics, network PCs, minicomputers, mainframe computers, distributed computing environments that comprise any of the above systems or devices, and the like.

The processing of the disclosed methods and systems can be performed by software components. The disclosed systems and methods can be described in the general context of computer-executable instructions, such as program modules, being executed by one or more computers or other devices. Generally, program modules comprise computer code, routines, programs, objects, components, data structures, etc. that perform particular tasks or implement particular abstract data types. The disclosed methods can also be practiced in grid-based and distributed computing environments where tasks are performed by remote processing devices that are linked through a communications network. In a distributed computing environment, program modules can be located in both local and remote computer storage media including memory storage devices.

Further, one skilled in the art will appreciate that the systems and methods disclosed herein can be implemented via a general-purpose computing device in the form of a computer 1601. The components of the computer 1601 can comprise, but are not limited to, one or more processors 1603, a system memory 1612, and a system bus 1613 that couples various system components including the one or more processors 1603 to the system memory 1612. The system can utilize parallel computing.

The system bus 1613 represents one or more of several possible types of bus structures, including a memory bus or memory controller, a peripheral bus, an accelerated graphics port, or local bus using any of a variety of bus architectures. The bus 1613, and all buses specified in this description can also be implemented over a wired or wireless network connection and each of the subsystems, including the one or more processors 1603, a mass storage device 1604, an operating system 1605, KaryoScan software 1606, KaryoScan data 1607, a network adapter 1608, the system memory 1612, an Input/Output Interface 1610, a display adapter 1609, a display device 1611, and a human machine interface 1602, can be contained within one or more remote computing devices 1614a,b,c at physically separate locations, connected through buses of this form, in effect implementing a fully distributed system.

The computer 1601 typically comprises a variety of computer readable media. Exemplary readable media can be any available media that is accessible by the computer 1601 and comprises, for example and not meant to be limiting, both volatile and non-volatile media, removable and non-removable media. The system memory 1612 comprises computer readable media in the form of volatile memory, such as random access memory (RAM), and/or non-volatile memory, such as read only memory (ROM). The system memory 1612 typically contains data such as the KaryoScan data 1607 and/or program modules such as the operating system 1605 and the KaryoScan software 1606 that are immediately accessible to and/or are presently operated on by the one or more processors 1603. The KaryoScan data 1607 can comprise read coverage data and/or expected read coverage data.

In another aspect, the computer 1601 can also comprise other removable/non-removable, volatile/non-volatile computer storage media. By way of example, FIG. 16 illustrates the mass storage device 1604 which can provide non-volatile storage of computer code, computer readable instructions, data structures, program modules, and other data for the computer 1601. For example and not meant to be limiting, the mass storage device 1604 can be a hard disk, a removable magnetic disk, a removable optical disk, magnetic cassettes or other magnetic storage devices, flash memory cards, CD-ROM, digital versatile disks (DVD) or other optical storage, random access memories (RAM), read only memories (ROM), electrically erasable programmable read-only memory (EEPROM), and the like.

Optionally, any number of program modules can be stored on the mass storage device 1604, including by way of example, the operating system 1605 and the KaryoScan software 1606. Each of the operating system 1605 and the KaryoScan software 1606 (or some combination thereof) can comprise elements of the programming and the KaryoScan software 1606. The KaryoScan data 1607 can also be stored on the mass storage device 1604. The KaryoScan data 1607 can be stored in any of one or more databases known in the art. Examples of such databases comprise, DB2®, Microsoft® Access, Microsoft® SQL Server, Oracle®, mySQL, PostgreSQL, and the like. The databases can be centralized or distributed across multiple systems.

In another aspect, the user can enter commands and information into the computer 1601 via an input device (not shown). Examples of such input devices comprise, but are not limited to, a keyboard, pointing device (e.g., a "mouse"), a microphone, a joystick, a scanner, tactile input devices such as gloves, and other body coverings, and the like. These and other input devices can be connected to the one or more processors 1603 via the human machine interface 1602 that is coupled to the system bus 1613, but can be connected by other interface and bus structures, such as a parallel port, game port, an IEEE 1394 Port (also known as a Firewire port), a serial port, or a universal serial bus (USB).

In yet another aspect, the display device 1611 can also be connected to the system bus 1613 via an interface, such as the display adapter 1609. It is contemplated that the computer 1601 can have more than one display adapter 1609 and the computer 1601 can have more than one display device 1611. For example, a display device can be a monitor, an LCD (Liquid Crystal Display), or a projector. In addition to the display device 1611, other output peripheral devices can comprise components such as speakers (not shown) and a printer (not shown) which can be connected to the computer 1601 via the Input/Output Interface 1610. Any step and/or result of the methods can be output in any form to an output device. Such output can be any form of visual representation, including, but not limited to, textual, graphical, animation, audio, tactile, and the like. The display 1611 and computer 1601 can be part of one device, or separate devices.

The computer 1601 can operate in a networked environment using logical connections to one or more remote computing devices 1614*a,b,c*. By way of example, a remote computing device can be a personal computer, portable computer, smartphone, a server, a router, a network computer, a peer device or other common network node, and so on. Logical connections between the computer 1601 and a remote computing device 1614*a,b,c* can be made via a network 1615, such as a local area network (LAN) and/or a general wide area network (WAN). Such network connections can be through the network adapter 1608. The network adapter 1608 can be implemented in both wired and wireless environments. Such networking environments are conventional and commonplace in dwellings, offices, enterprise-wide computer networks, intranets, and the Internet.

For purposes of illustration, application programs and other executable program components such as the operating system 1605 are illustrated herein as discrete blocks, although it is recognized that such programs and components reside at various times in different storage components of the computing device 1601, and are executed by the one or more processors 1603 of the computer. In an aspect, at least a portion of the KaryoScan software 1606 and/or the KaryoScan data 1607 can be stored on and/or executed on one or more of the computing device 1601, the remote computing devices 1614*a,b,c*, and/or combinations thereof. Thus the KaryoScan software 1606 and/or the KaryoScan data 1607 can be operational within a cloud computing environment whereby access to the KaryoScan software 1606 and/or the KaryoScan data 1607 can be performed over the network 1615 (e.g., the Internet). Moreover, in an aspect the KaryoScan data 1607 can be synchronized across one or more of the computing device 1601, the remote computing devices 1614*a,b,c*, and/or combinations thereof.

An implementation of the KaryoScan software 1606 can be stored on or transmitted across some form of computer readable media. Any of the disclosed methods can be performed by computer readable instructions embodied on computer readable media. Computer readable media can be any available media that can be accessed by a computer. By way of example and not meant to be limiting, computer readable media can comprise "computer storage media" and "communications media." "Computer storage media" comprise volatile and non-volatile, removable and non-removable media implemented in any methods or technology for storage of information such as computer readable instructions, data structures, program modules, or other data. Exemplary computer storage media comprises, but is not limited to, RAM, ROM, EEPROM, flash memory or other memory technology, CD-ROM, digital versatile disks (DVD) or other optical storage, magnetic cassettes, magnetic tape, magnetic disk storage or other magnetic storage devices, or any other medium which can be used to store the desired information and which can be accessed by a computer.

The methods and systems can employ Artificial Intelligence techniques such as machine learning and iterative learning. Examples of such techniques include, but are not limited to, expert systems, case based reasoning, Bayesian networks, behavior based AI, neural networks, fuzzy systems, evolutionary computation (e.g. genetic algorithms), swarm intelligence (e.g. ant algorithms), and hybrid intelligent systems (e.g. Expert inference rules generated through a neural network or production rules from statistical learning).

The KaryoScan method herein uses a novel co-normalization technique that assesses chromosomes in the context of their GC content and sequencing performance so that more accurate coverage normalization can be achieved. This is distinct from methods targeting the detection of smaller genomic changes as they are dependent entirely on the local GC-content biases. While methodologies targeting smaller changes can at times detect pieces of larger events, the smoothing functions (hidden Markov models for example) routinely used to understand high-resolution copy number changes in the context of larger events break down at the chromosome-arm scale. Furthermore, the integration of allele frequency data into KaryoScan calls provides for unique features including the detection of balanced genomic changes that do not present any signal in coverage space, but which may represent significant impact due to the loss of genetic variation.

In contrast to methods that force or provide an integer value call for a fractional CNV, such as a somatic cancer mutation or a mosaic event (i.e., in only a subset of cells in the body), the KaryoScan method herein provides an estimate of the fraction.

The following examples are put forth so as to provide those of ordinary skill in the art with a complete disclosure and description of how the compounds, compositions, articles, devices and/or methods claimed herein are made and evaluated, and are intended to be purely exemplary and are not intended to limit the scope of the methods and systems. Efforts have been made to ensure accuracy with respect to numbers (e.g., amounts, etc.), but some errors and deviations should be accounted for.

The disclosed methods were applied to 100,000 samples from the Regeneron Genetics Center's human exome variant database. In total, 3,150 samples were flagged as karyotypically abnormal at the highest stringency level on at least one tested chromosome, with 472 being gains or losses (not copy neutral). Over 200 samples were flagged as having sex chromosomal anomalies (chromosome X or chromosome Y), including extremely rare karyotypes (48, XXXX) and (48, XXXY).

While the methods and systems have been described in connection with preferred embodiments and specific examples, it is not intended that the scope be limited to the particular embodiments set forth, as the embodiments herein are intended in all respects to be illustrative rather than restrictive.

Unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is in no way intended that an order be inferred, in any respect. This holds for any possible non-express basis for interpretation, including: matters of logic with respect to arrangement of steps or operational flow; plain meaning derived from grammatical organization or punctuation; the number or type of embodiments described in the specification.

It will be apparent to those skilled in the art that various modifications and variations can be made without departing from the scope or spirit. Other embodiments will be apparent to those skilled in the art from consideration of the specification and practice disclosed herein. It is intended that the specification and examples be considered as exemplary only, with a true scope and spirit being indicated by the following claims.

What is claimed is:

1. A method comprising:
sequencing, using a sequencer, a plurality of samples;
generating, based on the sequencing, a plurality of sequencing quality control (SQC) metrics indicative of a quality of the sequencing of the plurality of samples performed by the sequencer;
generating, by a computing device, based on the sequencing, population-scale whole-exome sequencing data;
determining, based on the population-scale whole-exome sequencing data, a read coverage data profile for each sample in the plurality of samples relative to each chromosome, wherein each chromosome comprises a plurality of genomic regions;
filtering the read coverage data profiles based on a level of guanine-cytosine (GC) content in one or more genomic regions of the plurality of genomic regions;
determining, based on the filtered read coverage data profiles, an exome-wide ratio of read coverage data for each chromosome relative to other autosomes;
determining, based on application of a linear regression model to the filtered read coverage data profiles, an expected exome-wide ratio of read coverage data for each chromosome in the plurality of samples, wherein the linear regression model utilizes the plurality of SQC metrics as covariates, and wherein, for each chromosome, the covariates are restricted to covariates associated with two autosomes with minimal D-statistics relative to a GC content distribution for the chromosome;
determining, for at least one chromosome in a sample of the plurality of samples, a deviation between the exome-wide ratio of read coverage data and the expected exome-wide ratio of read coverage data; and
reporting, based on the deviation, an abnormal karyotype in the sample of the plurality of samples.

2. The method of claim 1, wherein determining read coverage data for each chromosome in a plurality of samples, wherein each chromosome comprises a plurality of genomic regions comprises determining a sum of read depths over exomic regions with GC content within a range and a mappability score above a threshold.

3. The method of claim 1, wherein filtering the read coverage data based on a level of guanine-cytosine (GC) content in one or more genomic regions of the plurality of genomic regions comprises:
determining a level of GC content for each of the plurality of genomic regions; and
excluding one or more genomic regions of the plurality of genomic regions having a level of GC content outside a range.

4. The method of claim 1, wherein filtering the read coverage data comprises filtering one or more genomic regions of the plurality of genomic regions based on a mappability score of the one or more genomic regions of the plurality of genomic regions.

5. The method of claim 4, wherein filtering one or more genomic regions of the plurality of genomic regions based on a mappability score of the one or more genomic regions of the plurality of genomic regions comprises:
determining a mappability score for each genomic region of the plurality of genomic regions; and
excluding one or more genomic regions of the plurality of genomic if the mappability score of the one or more genomic regions of the plurality of genomic regions is below a predetermined threshold.

6. The method of claim 1, wherein the exome-wide ratio is determined for each chromosome (i) by:

$$\gamma_i = \frac{r_i}{\sum_{\forall j \in (A-i)} r_j}$$

wherein A is the set of autosomes and r is read coverage.

7. The method of claim 1, wherein the expected exome-wide ratio ($\hat{\gamma}$) is determined for each chromosome (i) by:

$$\hat{\gamma}_i = f(QC\ metrics, \gamma_j, \gamma_k)$$

wherein chromosomes j,k are defined as two autosomes with minimal D statistics relative to the GC content distribution of chromosome i.

8. The method of claim 1, wherein determining a deviation between the read coverage data and the expected read coverage data for at least one chromosome in the plurality of samples comprises:
   determining, for each chromosome in the plurality of samples, a difference between the read coverage data and the expected read coverage data to generate a plurality of residuals; and
   Z-score normalizing the plurality of residuals relative to a standard error of the mean estimate, $S(\hat{\gamma}_i)$, for an individual sample of the plurality of samples with covariates x:

$$S(\hat{\gamma}_i) = S_e \sqrt{\frac{1}{n} + \frac{(x - \bar{x})^2}{\sum_{j=1\ \ldots\ n} (x_j - \bar{x})^2}}$$

where $S_e$ is the residual standard error, and:

$$Z_i = \frac{(\gamma_i - \hat{\gamma}_i)}{S(\hat{\gamma}_i)\sqrt{n}}.$$

9. The method of claim 8, further comprising determining a p-value based on the Z-score for each chromosome to identify significantly large residuals, representing abnormal karyotypes for chromosome i.

10. The method of claim 9, wherein significantly large residuals comprise residuals having a p-value less than 0.05.

11. The method of claim 9, further comprising:
    detecting one or more outliers; and
    removing the one or more outliers from consideration for identification as an abnormal karyotype.

12. The method of claim 11, wherein detecting one or more outliers comprises flagging one or more of the plurality of samples having leverage ($h_i$, where $1/n < h_i < 1$) above a threshold on the linear regression model for each chromosome, wherein leverage is determined as a function of n and p:

$$h_i(n, p) = \left[\frac{1}{n} + \frac{(x - \bar{x})^2}{\sum_{j=1\ \ldots\ n} (x_j - \bar{x})^2}\right] \cdot \frac{n}{p+1}$$

where p is the number of covariates in the model, n is the number of samples modeled, $x_i$ represents a vector of covariates for sample i, and $\bar{x}$ is the vector of covariate means across the sample population.

13. The method of claim 12, wherein the threshold is from about 3 to about 5.

14. The method of claim 1, further comprising: assigning, based on a significance of the deviation, a tier rating to the reported abnormal karyotype.

\* \* \* \* \*